(12) United States Patent
Subasinghe et al.

(10) Patent No.: US 7,482,376 B2
(45) Date of Patent: Jan. 27, 2009

(54) CONJUGATED COMPLEMENT CASCADE INHIBITORS

(75) Inventors: Nalin Subasinghe, West Chester, PA (US); Ehab Khalil, West Chester, PA (US); Farah Ali, Exton, PA (US); Heather Rae Hufnagel, Glenmoore, PA (US); Shelley Ballentine, Lansdale, PA (US); Jeremy M. Travins, Newtown Square, PA (US); Kristi A. Leonard, West Chester, PA (US); Roger F. Bone, Bridgewater, NJ (US)

(73) Assignee: 3-Dimensional Pharmaceuticals, Inc., Exton, PA (US)

( * ) Notice: Subject to any disclaimer, the term of this patent is extended or adjusted under 35 U.S.C. 154(b) by 559 days.

(21) Appl. No.: 10/869,430

(22) Filed: Jun. 16, 2004

(65) Prior Publication Data

US 2005/0004031 A1 Jan. 6, 2005

Related U.S. Application Data

(60) Provisional application No. 60/484,854, filed on Jul. 3, 2003, provisional application No. 60/571,374, filed on May 14, 2004.

(51) Int. Cl.
*A61K 31/381* (2006.01)
*C07D 333/10* (2006.01)

(52) U.S. Cl. ............... 514/445; 549/29; 549/59; 549/62; 549/65; 514/438; 514/444

(58) Field of Classification Search ............ 549/29, 549/59, 62, 65; 514/438, 444, 445
See application file for complete search history.

(56) References Cited

U.S. PATENT DOCUMENTS

| 5,962,535 | A | * | 10/1999 | Miyamoto et al. | ......... 514/724 |
| 6,063,764 | A | | 5/2000 | Creasey et al. | |
| 6,492,403 | B1 | | 12/2002 | Illig et al. | |
| 7,109,354 | B2 | * | 9/2006 | Subasinghe et al. | ........... 549/29 |
| 7,138,530 | B2 | * | 11/2006 | Subasinghe et al. | ........... 549/65 |
| 2002/0102256 | A1 | | 8/2002 | West et al. | |
| 2003/0105275 | A1 | | 6/2003 | Bentley et al. | |
| 2003/0171292 | A1 | | 9/2003 | Creasey et al. | |
| 2005/0004031 | A1 | * | 1/2005 | Subasinghe et al. | ........... 514/12 |

FOREIGN PATENT DOCUMENTS

| EP | 0 839 849 A1 | 5/1998 |
| EP | 1 283 233 A1 | 2/2003 |
| JP | 08 268912 A | 10/1996 |
| WO | WO 92/12095 A1 | 8/1992 |
| WO | WO 92/13095 A1 | 8/1992 |
| WO | WO 92/16221 A1 | 10/1992 |
| WO | WO 95/34326 A1 | 12/1995 |
| WO | WO 97/23637 A1 | 7/1997 |
| WO | WO 99/40088 A1 | 8/1999 |
| WO | WO 00/47578 A1 | 8/2000 |
| WO | WO 01/62299 A2 | 8/2001 |
| WO | WO 02/092008 A2 | 11/2002 |
| WO | WO 03/000777 A2 | 1/2003 |
| WO | WO 03/032990 A2 | 4/2003 |
| WO | WO 03/037384 A2 | 5/2003 |
| WO | WO 03/037385 A1 | 5/2003 |

OTHER PUBLICATIONS

International Search Report dated Jun. 3, 2005, for corresponding international application PCT/US2004/019457.
Greenwald R B et al: "Poly(Ethylene Glycol) Conjugated Drugs and ProDrugs: A Comprehensive Review", Critical Reviews in Therapeutic Drug Carrier Systems, vol. 17, No. 2, 2000, pp. 101-161 (XP001020454) ISSN: 0743-4863.
Nagasaka T et al: "Alpha-Galactosyl Oligosaccharides Conjugated with Polyethylene Glycol as Potential Inhibitors of Hyperacute Rejection Upon Xenotransplantation", Biochemical and Biophysical Research Communication, vol. 232, Mar. 1997, pp. 731-736 (XP002919605) ISSN: 0006-291X.

* cited by examiner

*Primary Examiner*—Golam M Shameem

(57) ABSTRACT

The present invention is directed to conjugated complement cascade inhibitors, and a method of treating a patient using a conjugated complement cascade inhibitor.

11 Claims, 11 Drawing Sheets

CONJUGATED COMPLEMENT CASCADE INHIBITORS

CROSS-REFERENCE TO RELATED APPLICATIONS

This application claims the benefit of U.S. Provisional Application Ser. No. 60/484,854, filed Jul. 3, 2003, and U.S. Provisional Application Ser. No. 60/571,374, filed May 14, 2004, the disclosures of which are hereby incorporated by reference in their entireties.

FIELD OF THE INVENTION

The present invention relates to novel compounds and their use in treating certain disorders in a patient. More specifically, the invention relates to conjugated complement cascade inhibitors.

BACKGROUND OF THE INVENTION

The complement cascade has a well studied purpose and effect, including its role in desirable immunological response. However, the undesirable initiation of the complement cascade has been implicated in certain well known disorders characterized by inflammation and tissue damage. Thus, complement cascade inhibitors have been developed that can be used to treat such disorders, including hereditary angioedema, septic shock, post pump syndrome in cardiopulmonary bypass, paroxysmal nocturnal hemoglobinurea, organ rejection, wounds, brain trauma, asthma, Hashimoto's thyroiditis, glomerulonephritis and cutaneous lesions of systemic lupus erythematosus, other glomerulonephritides, bullous pemphigoid, dermatitis herpetiformis, Goodpasture's syndrome, Graves' disease, myasthenia gravis, insulin resistance, autoimmune hemolyic anemia, autoimmune thrombocytopenic purpura, rheumatoid arthritis, multiple sclerosis, the neuropathies Guillain-Barre syndrome, Miller-Fisher syndrome, and Alzheimer's disease. See, e.g., U.S. Pat. Nos. 6,492,403 and 6,515,002.

The undesirable initiation of the complement cascade has been implicated in complications associated with cell transplantations and grafts as well. It is known that cell transplantations and grafts are desirable for treating diseases such as heart failure, diabetes, stroke, Parkinson's disease, Alzheimer's disease, dementia, liver disease, kidney disease, burns, and wounds. However, this treatment has often not been efficacious in practice due to the immunogenic nature of the cell transplantations and grafts, leading to activation of the complement cascade and eventually, to rejection. Thus, complement cascade inhibitors are desirable for ameliorating rejection.

However, it is always desirable to impart improved pharmacokinetic properties to compounds that are used to treat patients. Covalent attachment of polyethylene glycols (PEG) to protein drugs have been used to increase the in vivo circulatory time, water solubility and to decrease antigenicity of these drugs. See, for example, U.S. Pat. No. 5,711,944. It is possible to conjugate several polymer molecules to a large protein, such as, for example, insulin and hemoglobin, without interfering with the active residues that interact with its biological target. Retaining activity following conjugation of small proteins and peptides to a polymer has been more difficult because these bioactive materials often have few attachment sites not associated with biological activity. Polymer conjugation to non-peptidic small molecule drugs has been primarily limited to prodrug strategies. See, for example, U.S. Pat. No. 5,614,549, U.S. Pat. No. 5,622,986 and U.S. Pat. No. 6,127,355. In these approaches, a small molecule is linked to a non-antigenic polymer via a metabolically-labile covalent moiety, such as an ester. The drug must be released from the non-antigenic polymer by enzymatic hydrolysis of the ester to enable the small molecules to be transported across cell membranes into the cells.

Because complement cascade inhibitors bind with receptors on cell surfaces it is not necessary for them to cross cell membranes. Thus, small molecule prodrug approaches using metabolically-labile covalent linkages would be unnecessarily limiting. However, as in the case of protein drugs and small molecule prodrugs, it is nonetheless equally important to have techniques to modulate the pharmacokinetic properties of small molecule complement cascade inhibitors that do not cross cell membranes. Accordingly, there is an unfulfilled need for means to modulate the pharmacokinetic properties of small molecule complement cascade inhibitors.

The present invention is directed to these, as well as other important ends.

SUMMARY OF THE INVENTION

The present invention is directed, in part, to compounds comprising a conjugated complement cascade inhibitor. The compounds may advantageously bind to a receptor in a component of the complement cascade, and may thereby inhibit the complement cascade or inhibit the effects of the proteins which are formed from the cascade (for example C3a and C5a).

In one embodiment, the present invention provides a pharmaceutical for treating a patient, comprising a conjugated complement inhibitor.

In another embodiment, the present invention provides a method of treating a patient to suppress activation of the complement cascade, comprising administering a conjugated complement inhibitor to the patient.

These and other aspects of the invention will become more apparent from the present description and claims.

DETAILED DESCRIPTION OF ILLUSTRATIVE EMBODIMENTS

Figure 1:
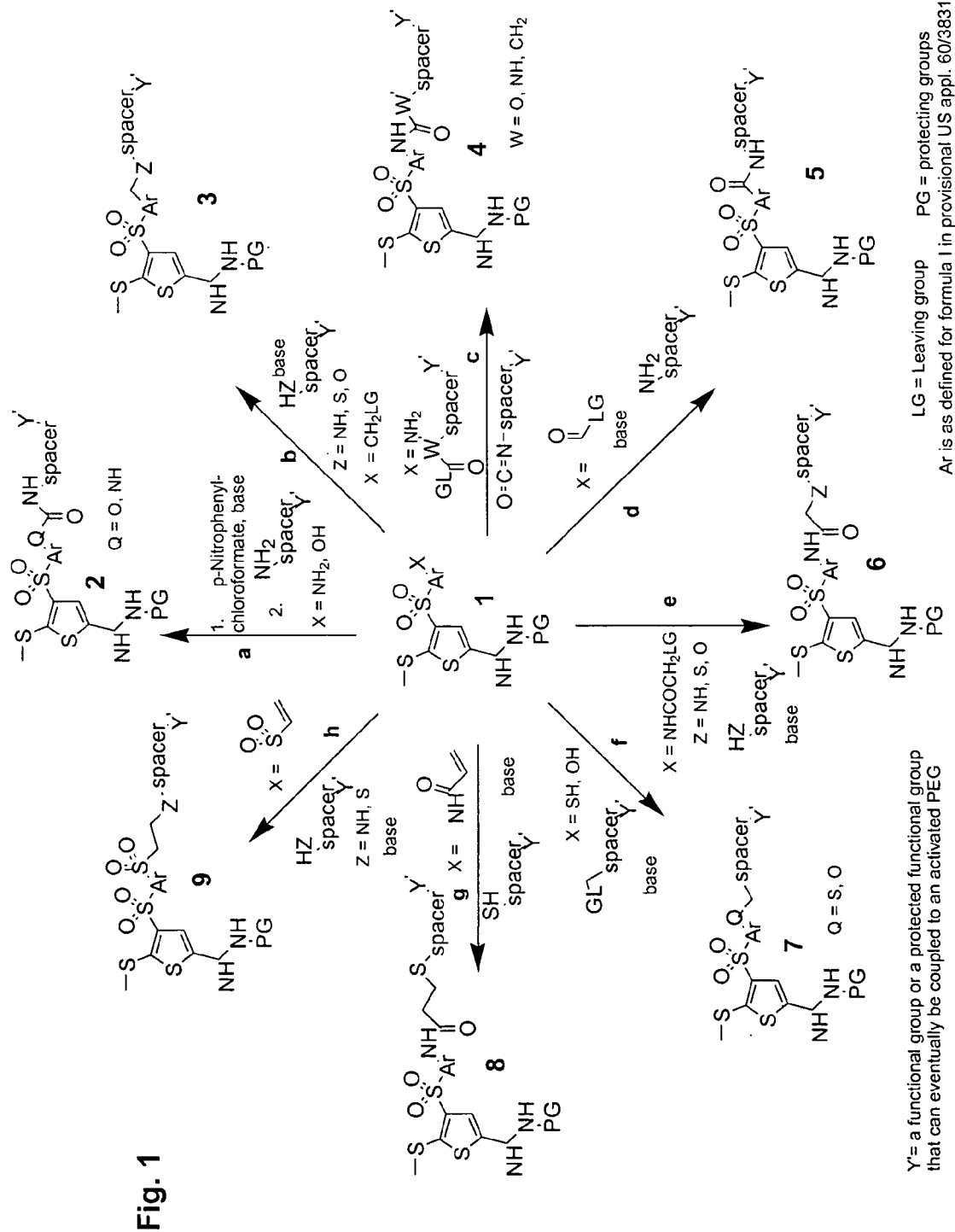
FIG. 1 is a schematic of potential reaction paths to form a drug-linker conjugate from a drug.

The present invention is directed, in part, to compounds comprising a conjugated complement cascade inhibitor. The compounds may advantageously bind to a receptor in a component of the complement cascade, and may thereby inhibit the complement cascade or inhibit the effects of the proteins which are formed from the cascade (for example C3a and C5a).

It is understood that "conjugated," as used in the present disclosure, means that a polymer moiety has been covalently attached to the moiety immediately following the term. Thus, for purposes of this disclosure, a conjugated complement cascade inhibitor is a complement cascade inhibitor with a covalently attached polymer moiety. The polymer may be selected from the group consisting of polyalkylene oxides, dextrans, polyvinyl pyrrolidones, polyacrylamides, polyvinyl alcohols, carbohydrate-based polymers, and "activated" polymers, as defined below.

The complement cascade inhibitor may be any compound that inhibits the complement cascade. Examples of such compounds include those disclosed in U.S. Pat. Nos. 6,492,403 and 6,515,002, and U.S. Ser. Nos. 60/383,130 and 10/445,817 filed May 28, 2003 (under client reference 1420001), the disclosures of which are hereby incorporated by reference in their entireties.

In one embodiment of the present invention, there is provided compounds of the formula (I):

(D-L)$_n$-P    (I)

wherein:
D is independently selected at each occurrence from compounds which are complement cascade inhibitors;
L is an optional (at each occurrence) linking group independently selected at each occurrence;
n is 1, 2, 3, 4, 5 or 6; and
P is a compound that enhances the pharmacokinetic properties of D.

In a preferred embodiment, D is connected to P (including via optional L) by a bond that is substantially non-hydrolyzable under physiological conditions.

In a preferred embodiment, n is 1.

In another preferred embodiment, n is 2.

In another preferred embodiment, n is 4.

It is understood that the formula (I) covers all possible combinations, for example, (D)n-P, (D-L)n-P, including D-L-D-L-P and D-L-P-L-D, and (D)n-P-(D-L)n.

Complement Cascade Inhibitors

A number of small molecule complement cascade inhibitors are known in the art and may be employed as components of the conjugated compounds of the invention, including, but not limited to compounds that bind to the C1s subcomponent, C1r subcomponent, C1q subcomponent, C5a receptor, C3, Factor D, Factor B, C3a receptor, and MASP-2. Suitable complement cascade inhibitors include the compounds that bind to the C1s subcomponent, such as, for example, the compounds disclosed in U.S. Pat. Nos. 6,492,403 and 6,515,002, and U.S. Ser. Nos. 60/383,130 and 10/445,817 filed May 28, 2003 (under client reference 1420001), the disclosures of which are hereby incorporated by reference in their entireties.

Suitable complement cascade inhibitors also include compounds that bind to the C1r subcomponent, such as, for example, the compounds disclosed in U.S. Pat. No. 5,652,237, the disclosure of which is hereby incorporated by reference in its entirety, and those disclosed in WO 00/61608.

Suitable complement cascade inhibitors also include compounds that bind to the C5a receptor, such as, for example, the compounds disclosed in WO 02/14265, the disclosure of which is hereby incorporated by reference in its entirety.

The foregoing examples are not intended to limit the scope of the disclosure, as it is understood that D can be any compound that inhibits the complement cascade. A suitable point for attaching D to L, or directly to P, can be determined by considering steric interactions regarding the specific binding mechanism, producing several D-L-P or D-P compounds using different respective attachment points, and screening the compounds for biological activity using known methods, such as, for example P. Giclas, *Therapeutic Interventions in the Complement System*, pp 225-236. Editors Lambris J. D.; Holers M. V. Generally, D will have, or can be substituted with, a suitable group for forming a bond with a complementary group, for example, amino, carboxy, hydroxyl, thiol, halogen, olefin, hydrazine, hydroxyl amine, aminoalkyl, carboxyalkyl, haloalkyl, hydroxyalkyl, and mercaptoalkyl.

In one embodiment, D is a C5a receptor antagonist.

In one embodiment, D is a compound that binds to the C1r subcomponent.

In one embodiment, D is a compound that binds to the C1q subcomponent.

In a preferred embodiment, D is a compound that binds to the MASP-2 subcomponent.

In a preferred embodiment, D is a compound that binds to the C1s subcomponent.

In a preferred embodiment, D is a compound that binds to both the C1s subcomponent and the MASP-2 subcomponent.

In a preferred embodiment, D is a non-peptide.

In a preferred embodiment, D is a small molecule, having a molecular weight in a range from about 100 molecular weight units to about 2000 molecular weight units (and all combinations and subcombinations of ranges and specific molecular weights therein), preferably about 400 molecular weight units to about 1200 molecular weight units, and alternatively about 400 molecular weight units to about 2000 molecular weight units.

In one embodiment, D is a non-aromatic compound.

In one embodiment, D is an aromatic compound.

In one embodiment, D is an aromatic guanidine.

In a preferred embodiment, D is an aromatic and/or heteroaromatic amidine.

In a preferred embodiment, D is a compound of the formula (II):

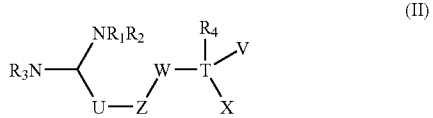

wherein:
R$_1$, R$_2$, and R$_3$ are independently selected from H, C$_{1-4}$ alkyl, amino, C$_{1-4}$ alkoxy, or hydroxy;
U is thiophenyl-R$_5$, benzylene, phenylene, NH or a bond;
R$_5$ is SO$_2$, NH, or a bond;
Z is arylene, heteroarylene, aralkylene, cycloalkylene, cycloheteroene;
W is C(=O)—O, HC(CH3)-NH—C(=O), O, NH, S, CH$_2$, C(=O), or a bond;
T is arylene, heteroarylene, aralkylene, cycloalkylene, cycloheteroene, C$_{1-4}$ alkyl, O, S, C$_{1-4}$ alkoxy, C$_{1-4}$ alkenyloxy, phenoxy, benzyloxy, halo, amino, or nitro;
X is amino, carboxy, hydroxyl, thiol, halogen, olefin, hydrazine, hydroxyl amine, aminoalkyl, carboxyalkyl, haloalkyl, hydroxyalkyl, mercaptoalkyl, or a bond to L or P;
V is methyl, ethyl, or Cl; and $R_4$ is H, $C_{1-4}$ alkyl, $C_{1-4}$ alkoxy, amidinyl, aminomethyl, $NH_2$, urea, or guanidinyl.

It is understood that D, L, and P will have slightly different formulas between their original "parent" compounds and their individual identities as part of the $(D-L)_n-P$ compound. However, one of skill in the art will not consider it necessary to delineate between the two formulas, for example, a D—NH—C(=O)-L bond ("connected" compound) is understandably the result of a D-$NH_2$ parent combined with an HOOC-L parent. Likewise, it will be readily appreciated that an $NH_2$—$CH_2$—$NH_2$ parent linker would be HN—$CH_2$—NH when part of the compound. Thus, unless specified, this specification will use the parent and connected forms interchangeably for the sake of simplicity.

In one embodiment, D is:

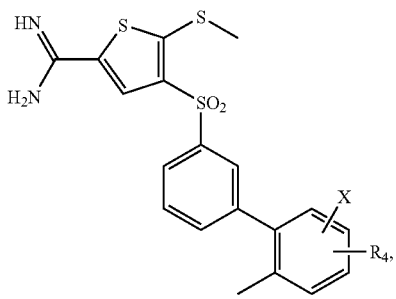

wherein:
$R_4$ is H, $C_{1-4}$ alkyl, $C_{1-4}$ alkoxy, amidinyl, aminomethyl, $NH_2$, urea, or guanidinyl, and
X is NH or C(=O) when D is connected to L or P.

In one embodiment, D is:

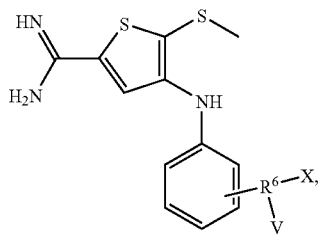

wherein:
X is NH or C(=O) when D is connected to L or P;
$R_6$ is $C_{1-4}$ alkyl, O, S, $C_{1-4}$ alkoxy, $C_{1-4}$ alkenyloxy, phenoxy, benzyloxy, halo, amino, or nitro;
and V is methyl or ethyl.

In one embodiment, D is:

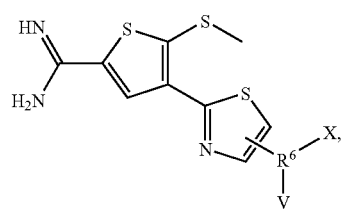

wherein:
X is NH or C(=O) when D is connected to L or P;
$R_6$ is $C_{1-4}$ alkyl, O, S, $C_{1-4}$ alkoxy, $C_{1-4}$ alkenyloxy, phenoxy, benzyloxy, halo, amino, phenyl, pyrazolyl, or nitro; and
V is methyl or ethyl.

Optional Linking Groups

When present, L may be a compound that acts to connect D to P, while providing space between the moieties. It is understood that this specification uses the term "spacer" as an abbreviation a portion of the "linker," for example, in a discussion where the terminal ends of a linker are disclosed, a group of linkers may be represented as $NH_2$ (or other terminal end)-spacer-SH (or other terminal end).

L is optional at each occurrence, and is independently selected at each occurrence. Thus, for example, where n is 3, a conjugated complement inhibitor of the present invention may have as few as no linking groups or as many as three different linking groups.

In a preferred embodiment, L is selected from the group:

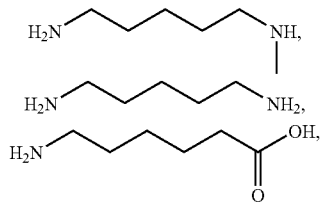

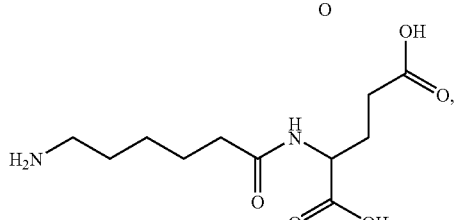

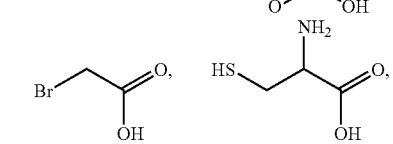

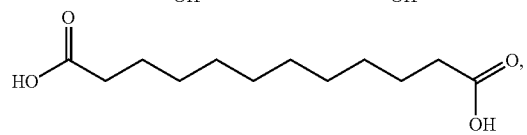

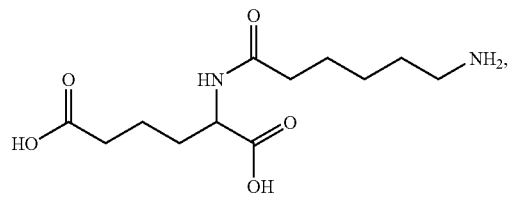

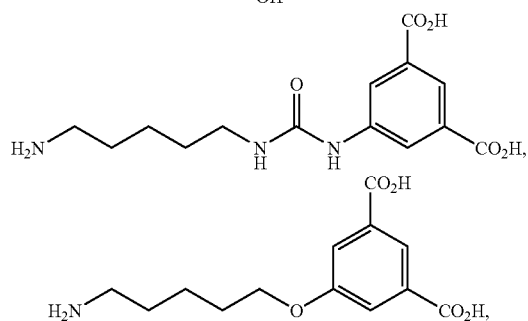

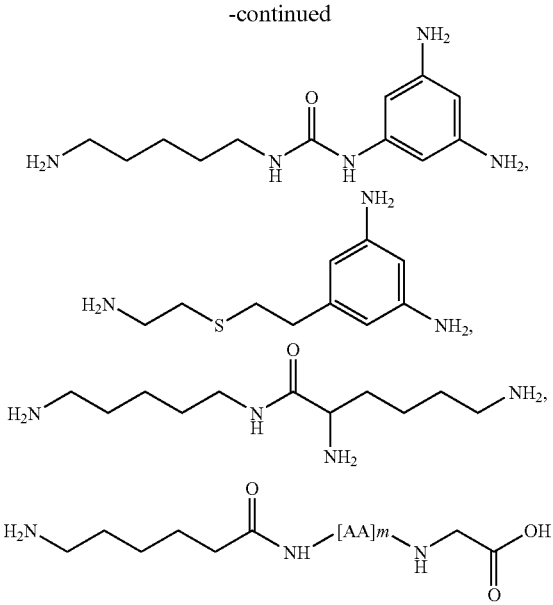

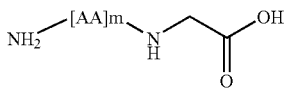

wherein AA is an amino acid, and m is 1-12,

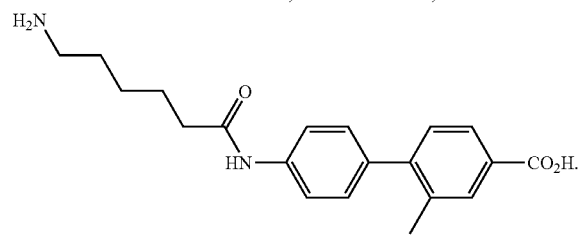

wherein AA is an amino acid, and m is 1-12, and

Pharmacokinetic Modifiers

In one embodiment, the pharmacokinetic modifier (P in formula (I)) may be a polymer selected from the group consisting of polyalkylene oxides (including polyethylene oxide, polypropylene oxide, and poly(ethylene-propylene) oxide), dextrans, polyvinyl pyrrolidones, polyacrylamides, polyvinyl alcohols, carbohydrate-based polymers, and "activated" polymers.

In a preferred embodiment, the pharmacokinetic modifier is a monomethyl-terminated polyethylene glycol having a molecular weight from about 750 formula weight units to about 60,000 formula weight units (and all combinations and subcombinations of ranges and specific molecular weights therein), preferably about 20,000 molecular weight units to about 40,000 molecular weight units.

Also in a preferred embodiment, the pharmacokinetic modifier is an activated polymer of formula (III):

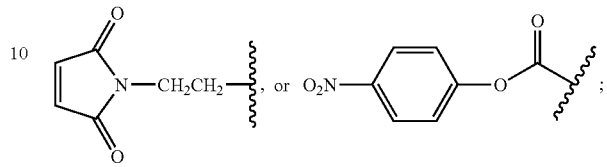                                                    (III)

wherein:

M is $CH_3$, $HC=CH-C(=O)$, $O=CH-CH_2$, $H_2N-CH_2-CH_2$, $Cl^-H_3N^+-HN-C(=O)-CH_2$, $O=C=N-CH_2CH_2$, $HS-CH_2CH_2$, $H_2C=CH-S(=O)_2-CH_2CH_2$,

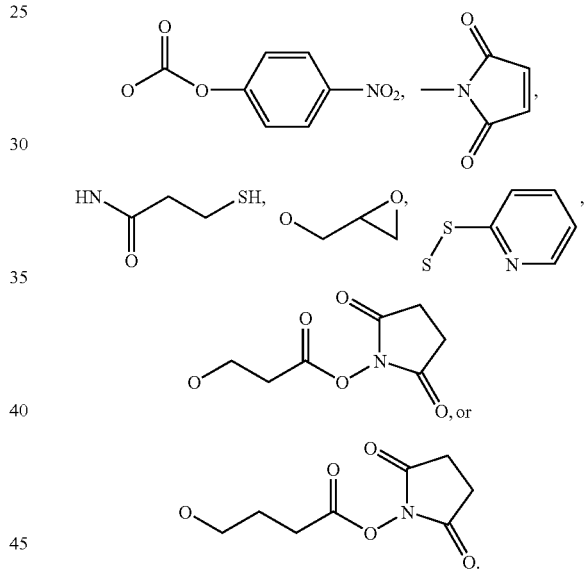

j is from about 17 to about 1400 (and all combinations and subcombinations of ranges and specific numerals therein); and A is $O-CH_2-CH(=O)$, $O-C(=O)-CH_2=CH_2$, $O-CH_2-CH_2-NH_2$, $NH_2$, $O-CH_2-C(=O)-NH-NH_3^+Cl^-$, $SH$, $N=C=O$, $S(=O)_2-CH=CH_2$,

In an alternative embodiment of the present invention, there is provided a compound of formula (IV):

$$D-L_n-P_{n'}$$ (IV)

wherein:

D is independently selected at each occurrence from compounds which are complement cascade inhibitors;

L is an optional (at each occurrence) linking group independently selected at each occurrence;

n is 1 or 2;

n' is 1, 2, 3, or 4; and

P is independently selected at each occurrence from compounds that enhance the pharmacokinetic properties of D.

It is understood that the formula (IV) covers all possible combinations, for example, (D)n-Pn', (D-L)n-Pn', including for example, D-L(-P)—P', P-D-P, D-L-P-L-P, D-L-P-L-D, P-D-L-D-L-P, and D-L-P-P-L-D, and (D)n-Pn'-(D-L)n.

In an alternative embodiment, D is a compound of formula (V):

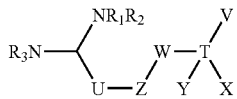

wherein:
$R_1$, $R_2$, and $R_3$ are independently selected from H, $C_{1-4}$ alkyl, amino, $C_{1-4}$ alkoxy, or hydroxy;
U is thiophenyl-$R_5$, benzylene, phenylene, NH or a bond;
$R_5$ is $SO_2$, NH, or a bond;
Z is arylene, heteroarylene, aralkylene, cycloalkylene, cycloheteroene;
W is C(=O)—O, HC(CH$_3$)—NH—C(=O), O, NH, S, CH$_2$, C(=O), or a bond;
T is arylene, heteroarylene, aralkylene, cycloalkylene, cycloheteroene, $C_{1-4}$ alkyl, O, S, $C_{1-4}$ alkoxy, $C_{1-4}$ alkenyloxy, phenoxy, benzyloxy, halo, amino, or nitro;
X is amino, carboxy, hydroxyl, thiol, halogen, olefin, hydrazine, hydroxyl amine, aminoalkyl, carboxyalkyl, haloalkyl, hydroxyalkyl, mercaptoalkyl, or a bond to L or P;
when present, Y is amino, carboxy, hydroxyl, thiol, halogen, olefin, hydrazine, hydroxyl amine, aminoalkyl, carboxyalkyl, haloalkyl, hydroxyalkyl, mercaptoalkyl, urea, guanidinyl, or a bond to L or P; and
V is methyl, ethyl, or Cl.
In a preferred embodiment, D is selected from the group:

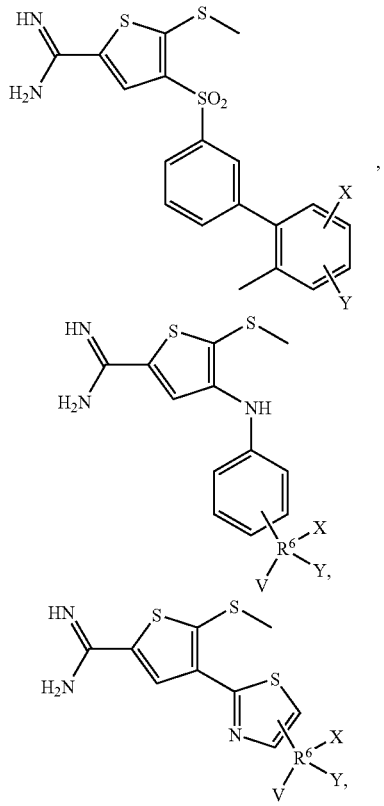

wherein:
X is NH or C(=O) when D is connected to L or P,
when present, Y is NH, C(=O), urea, or guanidinyl when D is connected to L or P, V is methyl or ethyl, and
$R_6$ is H, $C_{1-4}$ alkyl, OH, $C_{1-4}$ alkoxy, $C_{1-4}$ alkenyloxy, phenoxy, benzyloxy, halo, amino, phenyl, pyrazolyl, or nitro.

Optional Linking Groups
When present, L may be a compound that acts to connect D to P, while providing space between the moieties, and is substantially as described above.

Pharmacokinetic Modifiers
In this embodiment, the pharmacokinetic modifier is substantially as described above.
One example of a compound of formula (IV) where n=1 and n'=2 is:

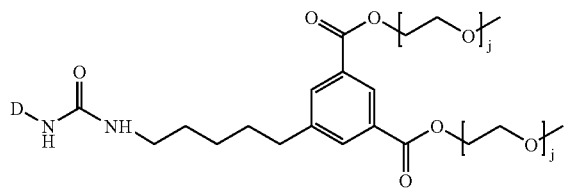

wherein:
D is a compound of formula (V), and
j is from about 17 to about 1400 (and all combinations and subcombinations of ranges and specific numerals therein).

Excipients
In one embodiment, excipients are selected from the known group of compounds that are used as a vehicle for active compounds in a pharmaceutical composition. The excipient is typically selected based on the chosen route of administration and standard pharmaceutical practice as described, for example, in *Remington's Pharmaceutical Sciences* (Mack Publishing Co., Easton, Pa., 1980), the disclosure of which is hereby incorporated herein by reference, in its entirety.
In an alternative embodiment, the active compounds are dissolved in phosphate buffered saline.

Methods of Using
In another embodiment, the present invention provides a method of treating a patient to suppress activation of the complement cascade, comprising administering a conjugated complement inhibitor to the patient.
The compounds may advantageously bind to a receptor in a component of the complement cascade, and may thereby inhibit the complement cascade or inhibit the effects of the proteins which are formed from the cascade (for example C3a and C5a). The need to suppress the complement cascade can be a result of certain disorders where activation of the complement cascade occurs with detrimental effects, or in certain clinical procedures (transplants, grafts, and the like) where the results of activation of the complement cascade are undesirable. This specification uses the term "disorders" to cover both of the foregoing scenarios and any time where one skilled in the art would recognize that the complement cascade should be suppressed.
Compounds of the present invention may be used to treat many disorders, including hereditary angioedema, septic shock, post pump syndrome in cardiopulmonary bypass, paroxysmal nocturnal hemoglobinurea, organ rejection, wounds, brain trauma, asthma, Hashimoto's thyroiditis, glomerulonephritis and cutaneous lesions of systemic lupus erythematosus, other glomerulonephritides, bullous pemphigoid, dermatitis herpetiformis, Goodpasture's syndrome, Graves' disease, myasthenia gravis, insulin resistance, autoimmune hemolyic anemia, autoimmune thrombocytopenic purpura, rheumatoid arthritis, multiple sclerosis, the neuropathies Guillain-Barre syndrome, Miller-Fisher syndrome, and Alzheimer's disease. Other disorders contemplated are disclosed in U.S. Pat. No. 6,515,002 and Ser. No. 60/383,130, the entire disclosures of which are incorporated herein by reference in their entireties.

In one embodiment, the present invention comprises methods of ameliorating rejection of a cell transplantation or a graft in an individual, comprising suppressing activation of the complement cascade.

Grafts refer to transference of tissue within an individual, between individuals of the same species, or between individuals of different species ("xenograft").

Cell transplantations refer to transference of cells within an individual, between individuals of the same species, or between individuals of different species. Cells that are transplanted include stem cells, primary cells from one or more donor animals, cells derived from tissue culture, pancreatic islet cells, cells expressing insulin, cells expressing glucose-modulating hormones, or cells expressing factors for the treatment of diabetes.

It is known that cell transplantations and grafts are desirable for treating diseases such as heart failure, diabetes, stroke, Parkinson's disease, Alzheimer's disease, dementia, liver disease, kidney disease, bums, and wounds. However, this treatment has often not been efficacious in practice due to the immunogenic nature of the cell transplantations and grafts, leading to activation of the complement cascade and eventually, to rejection. Thus, complement cascade inhibition is desirable for ameliorating rejection. See R J Armstrong, et al., Porcine Neural Xenografts In The Immunocompetent Rat: Immune Response Following Grafting Of Expanded Neural Precursor Cells, *Neuroscience*, 2001, 106(1):201-16; W Bennet, et al., Expression Of Complement Regulatory Proteins On Islets Of Langerhans: A Comparison Between Human Islets And Islets Isolated From Normal And hDAF Transgenic Pigs, *Transplantation*, Jul. 27, 2001, 72(2):312-9; R P Robertson, et al., Islet Transplantation As A Treatment For Diabetes—A Work In Progress, *N Engl J Med.*, Feb. 12, 2004, 350(7):694-705; T Lundgren, et al., Soluble Complement Receptor 1 (TP10) Preserves Adult Porcine Islet Morphology After Intraportal Transplantation Into Cynomolgus Monkeys, *Transplant Proc.* Feb.-Mar. 2001, 33(1-2):725; W Bennet, et al., Damage To Porcine Islets Of Langerhans After Exposure To Human Blood In Vitro, Or After Intraportal Transplantation To Cynomologus Monkeys: Protective Effects Of Scr1 And Heparin, *Transplantation*, Mar 15, 2000, 69(5):711-9; R Reca, et al., Functional Receptor For C3a Anaphylatoxin Is Expressed By Normal Hematopoietic Stem/Progenitor Cells, And C3a Enhances Their Homing-Related Responses To SDF-1, *Blood*, May 15, 2003, 101(10): 3784-93 (Epub Jan 2, 2003); K Teranishi, et al., Depletion Of Anti-Gal Antibodies By The Intravenous Infusion Of Gal Type 2 And 6 Glycoconjugates In Baboons, *Xenotransplantation*, Jul. 2003, 10(4):357-67; K Teranishi, et al., Depletion Of Anti-Gal Antibodies In Baboons By Intravenous Therapy With Bovine Serum Albumin Conjugated To Gal Oligosaccharides, *Transplantation*, Jan. 15, 2002, 73(1):129-39; J Z Appel, et al., Modulation Of Platelet Aggregation In Baboons: Implications For Mixed Chimerism In Xenotransplantation. I. The Roles Of Individual Components Of A Transplantation Conditioning Regimen And Of Pig Peripheral Blood Progenitor Cells, Transplantation, Oct. 15, 2001, 72(7):1299-305; M Basker, et al., Clearance Of Mobilized Porcine Peripheral Blood Progenitor Cells Is Delayed By Depletion Of The Phagocytic Reticuloendothelial System In Baboons, *Transplantation*, Oct. 15, 2001, 72(7):1278-85; L Buhler, et al., High-Dose Porcine Hematopoietic Cell Transplantation Combined With CD40 Ligand Blockade In Baboons Prevents An Induced Anti-Pig Humoral Response, *Transplantation*, Jun. 15, 2000, 69(11):2296-304.

In one embodiment, the present invention comprises a method of ameliorating rejection of a cell transplantation or a graft in an individual, comprising suppressing activation of the complement cascade by administering a conjugated complement inhibitor to the individual. The individual may be any animal having at least a portion of a complement cascade, and in one embodiment, the individual is a mammal.

It has been found that the tissue injury associated with organ preservation due to undesirable complement-mediated inflammatory reactions can be overcome by adding complement inhibitors to the organ preservation solution. See Bergamaschini L, et al., C1 inhibitor potentiates the protective effect of organ preservation solution on endothelial cells during cold storage, *Transplant Proc.* Feb.-Mar. 2001, 33(1-2): 939-41.

In one embodiment, the present invention comprises a method for preventing complement activation in an organ in an organ preservation solution, comprising contacting the organ with a conjugated complement inhibitor.

The transplants can be within an individual, between individuals of the same species, or between individuals of different species.

In one embodiment, the present invention comprises a method for preventing complement activation in response to insertion of a foreign object into an individual, comprising contacting the object with a conjugated complement inhibitor. The individual may be any animal having at least a portion of a complement cascade, and in one embodiment, the individual is a mammal. In one embodiment, the object is a surgical implant, an artificial organ, or an artificial joint, or similar object whereupon complement activation would be undesirable.

In one embodiment, the conjugated complement inhibitor is a compound having formula (I) or formula (IV):

$$(D-L)_n-P \quad (I)$$

$$D-L_n-P_{n'} \quad (IV)$$

wherein:
D is independently selected at each occurrence from compounds which are complement cascade inhibitors;
L is an optional (at each occurrence) linking group independently selected at each occurrence;
n is 1, 2, 3, 4, 5, or 6;
n' is 1, 2, 3, or 4; and
P is a compound that enhances the pharmacokinetic properties of D.

In one embodiment, D is a compound of the formula (VI):

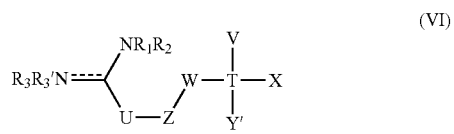

wherein:

$R_1, R_2, R_3$, and optionally $R_3$ are independently selected from H, $C_{1-4}$ alkyl, amino, $C_{1-4}$ alkoxy, or hydroxyl, wherein $R_3$ is not present when the dotted line represents a double bond;

U is thiophenyl-$R_5$, benzylene, phenylene, NH or a bond;

$R_5$ is $SO_2$, NH, or a bond;

Z is arylene, heteroarylene, aralkylene, cycloalkylene, cycloheteroene;

W is C(=O)—O, HC(CH$_3$)—NH—C(=O), O, NH, S, CH$_2$, C(=O), or a bond;

T is arylene, heteroarylene, aralkylene, cycloalkylene, cycloheteroene, $C_{1-4}$ alkyl, O, S, $C_{1-4}$ alkoxy, $C_{1-4}$ alkenyloxy, phenoxy, benzyloxy, halo, amino, or nitro;

X is amino, carboxy, hydroxyl, thiol, halogen, olefin, hydrazine, hydroxyl amine, aminoalkyl, carboxyalkyl, haloalkyl, hydroxyalkyl, mercaptoalkyl, or a bond to L or P;

when present, Y' is amino, carboxy, hydroxyl, thiol, halogen, olefin, hydrazine, hydroxyl amine, aminoalkyl, carboxyalkyl, haloalkyl, hydroxyalkyl, mercaptoalkyl, urea, guanidinyl, H, $C_{1-4}$ alkyl, $C_{1-4}$ alkoxy, amidinyl, aminomethyl, $NH_2$, or a bond to L or P; and V is methyl, ethyl, or Cl.

In one embodiment, L is present, and is selected from the group:

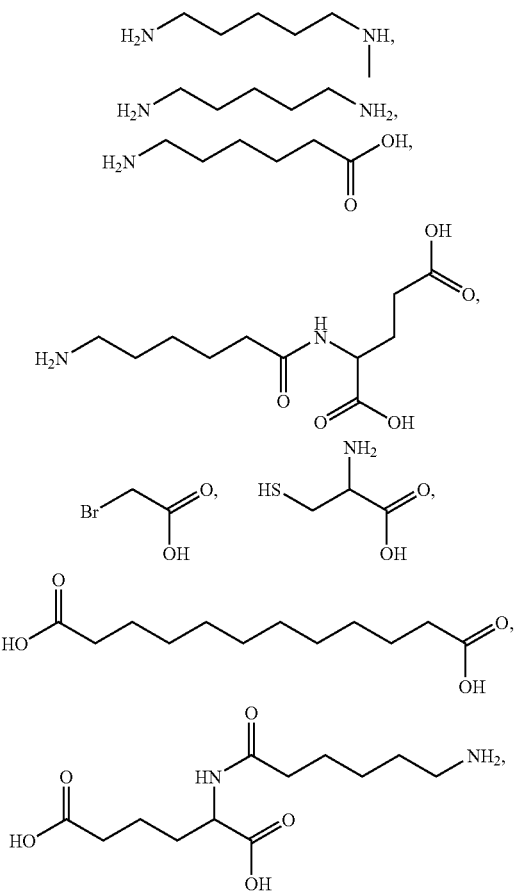

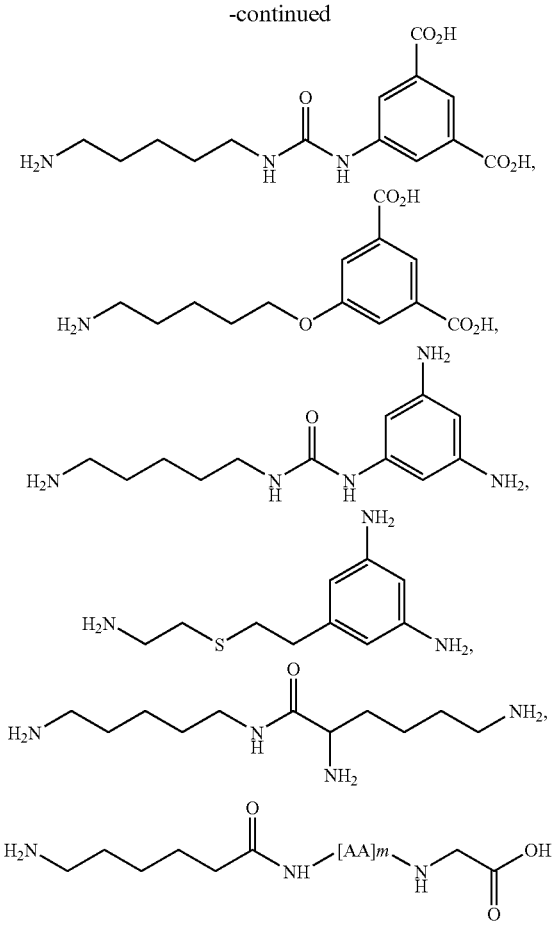

wherein AA is an amino acid, and m is 1-12,

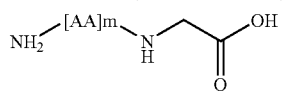

wherein AA is an amino acid, and m is 1-12, and

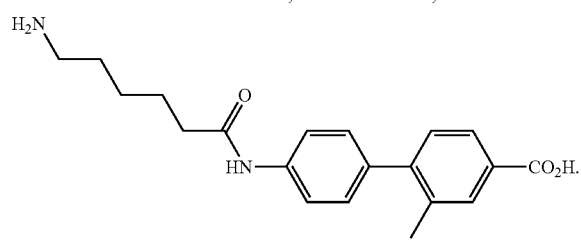

In one embodiment, P is an activated polymer having a formula (III):

wherein:
M is $CH_3$, HC=CH—C(=O), O=CH—CH$_2$, $H_2N$—CH$_2$—CH$_2$, Cl$^-$H$_3$N$^+$—HN—C(=O)—CH$_2$, O=C=N—CH$_2$CH$_2$, HS—CH$_2$CH$_2$, $H_2$C=CH—S(=O)$_2$—CH$_2$CH$_2$,

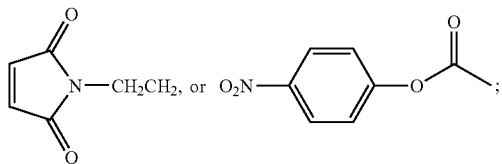

j is from 17 to 1400; and

A is O—CH$_2$—CH(=O), O—C(=O)—CH$_2$=CH$_2$, O—CH$_2$—CH$_2$—NH$_2$, NH$_2$, O—CH$_2$—C(=O)—NH—NH$_3^+$Cl$^-$, SH, N=C=O, S(=O)$_2$—CH=CH$_2$,

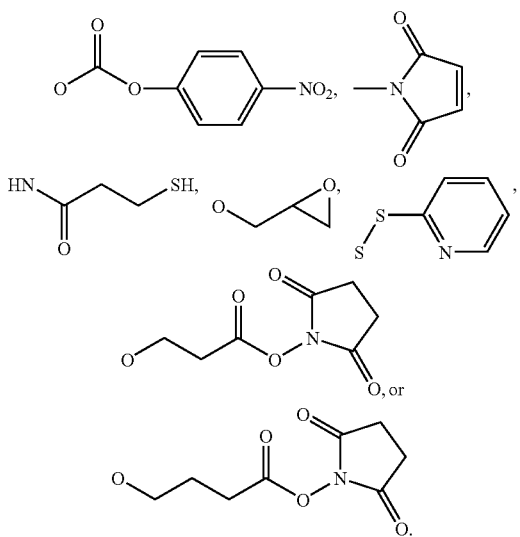

The useful dosage to be administered and the particular mode of administration will vary depending upon such factors as age, weight, and particular region to be treated, as well as the particular make-up and form of the pharmaceutical, as will be readily apparent to those skilled in the art. Typically, dosage is administered at lower levels and increased until the desirable therapeutic effect is achieved. The relative proportions of active ingredient and carrier may be determined, for example, by the solubility and chemical nature of the compound, chosen route of administration and standard pharmaceutical practice.

The dosage of the compounds of the present invention that will be most suitable for prophylaxis or treatment will vary with the form of administration, the particular compound chosen and the physiological characteristics of the particular patient under treatment. Generally, small dosages may be used initially and, if necessary, increased by small increments until the desired effect under the circumstances is reached. The therapeutic human dosage, based on physiological studies using rats, may generally range from about 0.01 mg to about 600 mg/kg of body weight per day, and all combinations and subcombinations of ranges therein. Alternatively, the therapeutic human dosage may be from about 0.4 mg to about 10 g or higher, and may be administered in several different dosage units from once to several times a day. Generally speaking, oral administration may require higher dosages.

Compounds employed in the methods of the present invention may be administered by any means that results in the contact of the active agent with the agent's site of action in the body of a patient, for example, orally or parenterally.

Parenteral administration includes administration by the following routes: intravenous, intramuscular, subcutaneous, rectal, intraocular, intrasynovial, transepithelial including transdermal, ophthalmic, sublingual and buccal; topically including ophthalmic, dermal, ocular, rectal, and nasal inhalation via insufflation aerosol.

Solutions of the active compound as a free base or a pharmacologically acceptable salt can be prepared in water suitably mixed with a surfactant, such as hydroxypropylcellulose. A dispersion can also be prepared in glycerol, liquid polyethylene glycols and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the active compound in the required amount, in the appropriate solvent, with various of the other ingredients enumerated above, as required, followed by filtered sterilization. Generally, dispersions may be prepared by incorporating the sterilized active ingredient into a sterile vehicle that contains the basic dispersion medium and the required other ingredients from those enumerated above. In the case of sterile powders for the preparation of sterile injectable solutions, the preferred methods of preparation may include vacuum drying and the freeze drying technique which yield a powder of the active ingredient, plus any additional desired ingredient from the previously sterile-filtered solution thereof.

The compounds may be administered by any conventional means available for use in conjunction with pharmaceuticals, either as individual therapeutic agents or in a combination with other therapeutic agents. Other therapeutic ingredients include, but are not limited to, antibiotics, antivirals, antifungals, anti-inflammatories, including steroidal and non-steroidal anti-inflammatories, anesthetics, antiemetics, immunosuppressants, and mixtures thereof.

Such additional ingredients include any of the following:
a. Antibacterial agents—Aminoglycosides, such as Amikacin, Apramycin, Arbekacin, Bambermycins, Butirosin, Dibekacin, Dihydrostreptomycin, Fortimicin(s), Fradiomycin, Gentamicin, Ispamicin, Kanamycin, Micronomicin, Neomycin, Neomycin Undecylenate, Netilmicin, Paromomycin, Ribostamycin, Sisomicin, Spectinomycin, Streptomycin, Streptonicozid and Tobramycin; Amphenicols, such as Azidamfenicol, Chloramphenicol, Chloramphenicol Palmirate, Chloramphenicol Pantothenate, Florfenicol, Thiamphenicol; Ansamycins, such as Rifamide, Rifampin, Rifamycin and Rifaximin; β-Lactams; Carbapenems, such as Imipenem; Cephalosporins, such as 1-Carba (dethia) Cephalosporin, Cefactor, Cefadroxil, Cefamandole, Cefatrizine, Cefazedone, Cefazolin, Cefixime, Cefmenoxime, Cefodizime, Cefonicid, Cefoperazone, Ceforanide, Cefotaxime, Cefotiam, Cefpimizole, Cefpirimide, Cefpodoxime Proxetil, Cefroxadine, Cefsulodin, Ceftazidime, Cefteram, Ceftezole, Ceftibuten, Ceftizoxime, Ceftriaxone, Cefuroxime, Cefuzonam, Cephacetrile Sodium, Cephalexin, Cephaloglycin, Cephaloridine, Cephalosporin, Cephalothin, Cephapirin Sodium, Cephradine and Pivcefalexin; Cephamycins such as Cefbuperazone, Cefinetazole, Cefininox, Cefetan and Cefoxitin; Monobactams such as Aztreonam, Carumonam and Tigemonan; Oxacephems such as Flomoxef and Moxolactam; Penicillins such as Amidinocillin, Amdinocillin, Pivoxil, Amoxicillin, Ampicillan, Apalcillin, Aspoxicillin, Azidocillan, Azlocillan, Bacampicillin, Benzylpenicillinic Acid, Benzylpenicillin, Carbenicillin, Carfecillin, Carindacillin, Clometocillin, Cloxacillin, Cyclacillin, Dicloxacillin, Diphenicillin, Epicillin, Fenbenicillin, Floxicillin, Hetacillin, Lenampicillin, Metampicillin, Methicillin, Mezlocillin, Nafcillin, Oxacillin, Penamecillin, Penethamate Hydriodide, Penicillin G Benethamine, Penicillin G Benzathine, Penicillin G Benzhydrylamine, Penicillin G Calcium, Penicillin G Hydragamine, Penicillin G Potassium, Penicillin G. Procaine, Penicillin N, Penicillin O, Penicillin V, Penicillin V Benzathine, Penicillin V Hydrabamine, Penimepicycline, Phenethicillin, Piperacillin, Pivapicillin, Propicillin, Quinacillin, Sulbenicillin, Talampicillin, Temocillin and Ticarcillin; Lincosumides such as Clindamycin and Lincomycin; Macrolides such as Azithromycin, Carbomycin, Clarithromycin, Erythromycin(s) and Derivatives, Josamycin, Leucomycins, Midecamycins, Miokamycin, Oleandomycin, Primycin, Rokitamycin, Rosaramicin, Roxithromycin, Spiramycin and Troleandomycin; Polypeptides such as Amphomycin, Bacitracin, Capreomycin, Colistin, Enduracidin, Enviomycin, Fusafungine, Gramicidin(s), Gramicidin S, Mikamycin, Polymyxin, Polymyxin β-Methanesulfonic Acid, Pristinamycin, Ristocetin, Teicoplanin, Thiostrepton, Tuberactinomycin, Tyrocidine, Tyrothricin, Vancomycin, Viomycin(s), Virginiamycin and Zinc Bacitracin; Tetracyclines such as Spicycline, Chlortetracycline, Clomocycline, Demeclocycline, Doxycycline, Guamecycline, Lymecycline, Meclocycline, Methacycline, Minocycline, Oxytetracycline, Penimepicycline, Pipacycline, Rolitetracycline, Sancycline, Senociclin, and Tetracycline; and others such as Cycloserine, Mupirocin, and Tuberin.
b. Synthetic Antibacterials—2,4-Diaminopyrimidines such as Brodimoprim, Tetroxoprim and Trimethoprim; Nitrofurans such as Furaltadone, Furazolium, Nifuradene, Nifuratel, Nifurfoline, Nifurpirinol, Nifurprazine, Nifurtoinol and Nitrofurantoin; Quinolones and analogs thereof, such as Amifloxacin, Cinoxacin, Ciprofloxacin, Difloxacin, Enoxacin, Fleroxacin, Flumequine, Lomefloxacin, Miloxacin, Nalidixic Acid, Norfloxacin, Ofloxacin, Oxolinic Acid, Perfloxacin, Pipemidic Acid, Piromidic Acid, Rosoxacin, Temafloxacin and Tosufloxacin; Sulfonamides such as Acetyl Sulfamethoxypyrazine, Acetyl Sulfisoxazole, Azosulfamide, Benzylsulfamide, Chloramine-β, Chloramine-T, Dichloramine-T, Formosulfathiazole, N.sup.2-Formyl-sulfisomidine, N.sup.4-β-D-Glucosylsulfanilamide, Mafenide, 4'-(Methyl-sulfamoyl)sulfanilanilide, p-Nitrosulfathiazole, Noprylsulfamide, Phthalylsulfacetamide, Phthalylsulfathiazole, Salazosulfadimidine, Succinylsulfathiazole, Sulfabenzamide, Sulfacetamide, Sulfachlorpyridazine, Sulfachrysoidine, Sulfacytine, Sulfadiazine, Sulfadicramide, Sulfadimethoxine, Sulfadoxine, Sulfaethidole, Sulfaguanidine, Sulfaguanol, Sulfalene, Sulfaloxic Acid, Sulfamerazine, Sulfameter, Sulfamethazine, Sulfamethizole, Sulfamethomidine, Sulfamethoxazole, Sulfamethoxypyridazine, Sulfametrole, sulfamidochrysoidine, Sulfamoxole, Sulfanilamide, Sulfanilamidomethanesulfonic Acid Triethanolamine Salt, 4-Sulfanilamidosalicyclic Acid, N.sup.4-Sulfanilylsulfanilamide, Sulfanilylurea, N-Sulfanilyl-3,4-xylamide, Sulfanitran, Sulfaperine, Sulfaphenazole, Sulfaproxyline, Sulfapyrazine, Sulfapyridine, Sulfasomizole, Sulfasymazine, Sulfathiazole, Sulfathiourea, Sulfatolamide, Sulfisomidine and Sulfisoxazole; Sulfones, such as Acedapsone, Acediasulfone, Acetosulfone, Dapsone, Diathymosulfone, Glucosulfone, Solasulfone, Succisulfone, Sulfanilic Acid, p-Sulfanilylbenzylamine, p,p'-sulfonyldianiline-N,N'digalactoside, Sulfoxone and Thiazolsulfone; and others such as Clofoctol, Hexedine, Magainins, Methenamine, Methenamine Anhydromethylene-citrate, Methenamine Hippurate, Methenamine Mandelate, Methenamine Sulfosalicylate, Nitroxoline, Squalamine, and Xibomol.
c. Antifungal (antibiotics)—Polyenes such as Amphotericin-B, Candicidin, Dermostatin, Filipin, Fungichromin, Hachimycin, Hamycin, Lucensomycin, Mepartricin, Natamycin, Nystatin, Pecilocin, Perimycin; and others, such as Azaserine, Griseofulvin, Oligomycins, Pyrrolnitrin, Siccanin, Tubercidin, and Viridin.
d. Antifungal (synthetic)—Allylamines such as Naftifine and terbinafine; Imidazoles such as Bifonazole, Butoconazole, Chlordantoin, Chlormidazole, Cloconazole, Clotrimazole, Econazole, Enilconazole, Finticonazole, Isoconazole, Ketoconazole, Miconazole, Omoconazole, Oxiconazole Nitrate, Sulconazole and Tioconazole; Triazoles such as Fluconazole, Itraconazole, Terconazole; and others such as Acrisorcin, Amorolfine, Biphenamine, Bromosalicylchloranilide, Buclosamide, Chlophenesin, Ciclopirox, Cloxyquin, Coparaffinate, Diamthazole, Dihydrochloride, Exalamide, Flucytosine, Halethazole, Hexetidine, Loflucarban, Nifuratel, Potassium Iodide, Propionic Acid, Pyrithione, Salicylanilide, Sulbentine, Tenonitrozole, Tolciclate, Tolindate, Tolnaftate, Tricetin, Ujothion, and Undecylenic Acid.
e. Antiglaucoma agents—Antiglaucoma agents, such as Dapiprazoke, Dichlorphenamide, Dipivefrin, and Pilocarpine.
f. Anti-inflammatory agents—Corticosteroids, aminoarylcarboxylic Acid Derivatives such as Etofenamate, Meclofenamic Acid, Mefanamic Acid, Niflumic Acid; Arylacetic Acid Derivatives such as Acemetacin, Amfenac Cinmetacin, Clopirac, Diclofenac, Fenclofenac, Fenclorac, Fenclozic Acid, Fentiazac, Glucametacin, Isozepac, Lonazolac, Metiazinic Acid, Oxametacine, Proglumetacin, Sulindac, Tiaramide and Tolmetin; Arylbutyric Acid Derivatives such as Butibufen and Fenbufen; Arylcarboxylic Acids such as Clidanac, Ketorolac and Tinoridine; Arylpropionic Acid Derivatives such as Bucloxic Acid, Carprofen, Fenoprofen, Flunoxaprofen, Ibuprofen, Ibuproxam, Oxaprozin, Piketoprofen, Pirprofen, Pranoprofen, Protizinic Acid and Tiaprofenic Acid; Pyrazoles such as Mepirizole; Pyrazolones such as Clofezone, Feprazone, Mofebutazone, Oxyphenbutazone, Phenylbutazone, Phenyl Pyrazolidininones, Suxibuzone and Thiazolinobutazone; Salicylic Acid Derivatives such as Bromosaligenin, Fendosal, Glycol Salicylate, Mesalamine, 1-Naphthyl Salicylate, Olsalazine and Sulfasalazine; Thiazinecarboxamides such as Droxicam, Isoxicam and Piroxicam; and others such as e-Acetamidocaproic Acid, S-Adenosylmethionine, 3-Amino-4-hydroxybutyric Acid, Amixetrine, Bendazac, Bucolome, Carbazones, Difenpiramide, Ditazol, Guaiazulene, Heterocyclic Aminoalkyl Esters of Mycophenolic Acid and Derivatives, Nabumetone, Nimesulide, Orgotein, Oxaceprol, Oxazole Derivatives, Paranyline, Pifoxime, 2-substituted-4,6-di-tertiary-butyl-s-hydroxy-1,3-pyrimidines, Proquazone, and Tenidap.

g. Antiseptics—Guanidines such as Alexidine, Ambazone, Chlorhexidine and Picloxydine; Halogens/Halogen Compounds such as Bornyl Chloride, Calcium Iodate, Iodine, Iodine Monochloride, Iodine Trichloride, lodoform, Povidone-lodine, Sodium Hypochlorite, Sodium Iodate, Symclosene, Thymol Iodide, Triclocarban, Triclosan and Troclosene Potassium; Nitrofurans such as Furazolidone, 2-(Methoxymethyl)-5-Nitrofuran, Nidroxyzone, Nifuroxime, Nifurzide and Nitrofurazone; Phenols such as Acetomeroctol, Chloroxylenol, Hexachlorophene, 1-Naphthyl Salicylate, 2,4,6-Tribromo-m-cresol and 3',4',5-Trichlorosalicylanilide; Quinolines such as Aminoquinuride, Chloroxine, Chlorquinaldol, Cloxyquin, Ethylhydrocupreine, Halquinol, Hydrastine, 8-Hydroxyquinoline and Sulfate; and others, such as Boric Acid, Chloroazodin, m-Cresyl Acetate, Cupric sulfate, and Ichthammol.

h. Antivirals—Purines/Pyrimidinones, such as 2-Acetyl-Pyridine 5-((2-pyridylamino)thiocarbonyl) Thiocarbonohydrazone, Acyclovir, Dideoxyadenosine, dideoxycytidine, Dideoxyinosine, Edoxudine, Floxuridine, Ganciclovir, Idoxuridine, MADU, Pyridinone, Trifluridine, Vidrarbine and Zidovudline; Acetylleucine Monoethanolamine, Acridinamine, Alkylisooxazoles, Amantadine, Amidinomycin, Cuminaldehyde Thiosemicarbzone, Foscamet Sodium, Kethoxal, Lysozyme, Methisazone, Moroxydine, Podophyllotoxin, Ribavirin, Rimantadine, Stallimycin, Statolon, Thymosins, Tromantadine, and Xenazoic Acid.

i. Immunosuppressants—Methylprednisolone, Atgam, Thymoglobulin, OKT3, Basiliximab, Daclizumab, Rapamycin, Prednisone, Cyclosporine, Tacrolimus, Mycophenolate Mofetil, and Azathioprine.

Methods of Preparing

In another embodiment, the present invention provides methods of preparing the complement cascade inhibitors.

FIG. 1 illustrates a schematic summarizing eight methodologies that may be used to introduce a bi-functional linker (linker L in formula I) onto the key scaffold 1 (U.S. provisional application 60/383130) to provide a suitable handle for conjugation on intermediates 2-9. When X=$NH_2$ or OH, scaffold 1 can be pre-activated to the p-nitrophenylcarbamate or p-nitrophenylcarbonate, respectively by treating with p-nitrophenylchloroformate in the presence of a base such as pyridine. This in-situ generated intermediate is immediately reacted with a suitable linker ($NH_2$-spacer-Y') in the presence of a base, preferably triethylamine or diisopropylethylamine to generate the urea or carbamate 2 (path a). When X=NH2, scaffold 1 can be directly reacted with a linker containing a activated-carbamate, or isocyanate to give an urea 4 (W'=NH). When X=NH2, scaffold 1 can also be treated with a linker containing a carbonate or an activated acid functionality (or acid chloride), to give respectively a carbamate 4 (W'=O) or an amide 4 (W'=CH2). In another variation of this route, a nucelophile (X=SH or OH) on scaffold 1 may be alkylated by displacing a good leaving group on the linker in a nucleophilic substitution reaction to produce intermediate 7 (path f). Additionally, a good leaving group (preferably, LG=Cl, Br, I, p-nitrophenol, methylsulfonate, or p-toluenesolfonate) on scaffold 1 may be used to alkylate a suitable bifunctional liker to provide intermediates 3 or 6 (as described in paths b and e, respectively), where Z=NH, S, or O. Alternatively when X is an acid chloride or an activated acid this can be treated with an amine containing linker as shown in path d to give an amide 5. In path d, the activated acid can be generated in situ by treating with a number of standard peptide coupling reagents, preferably DIC/DMAP. Finally, the conjugation of scaffold 1 and the linker may be accomplished by carrying out a conjugative addition with a suitable Michael acceptor incorporated into X. Thus, reaction of a linker bearing a suitable nucleophile (Z=NH or S) with an acrylamide or vinyl sulfone, in the presence of a base, furnishes the desired intermediates 8 or 9 (as described in path g and h, respectively).

Figure 2:
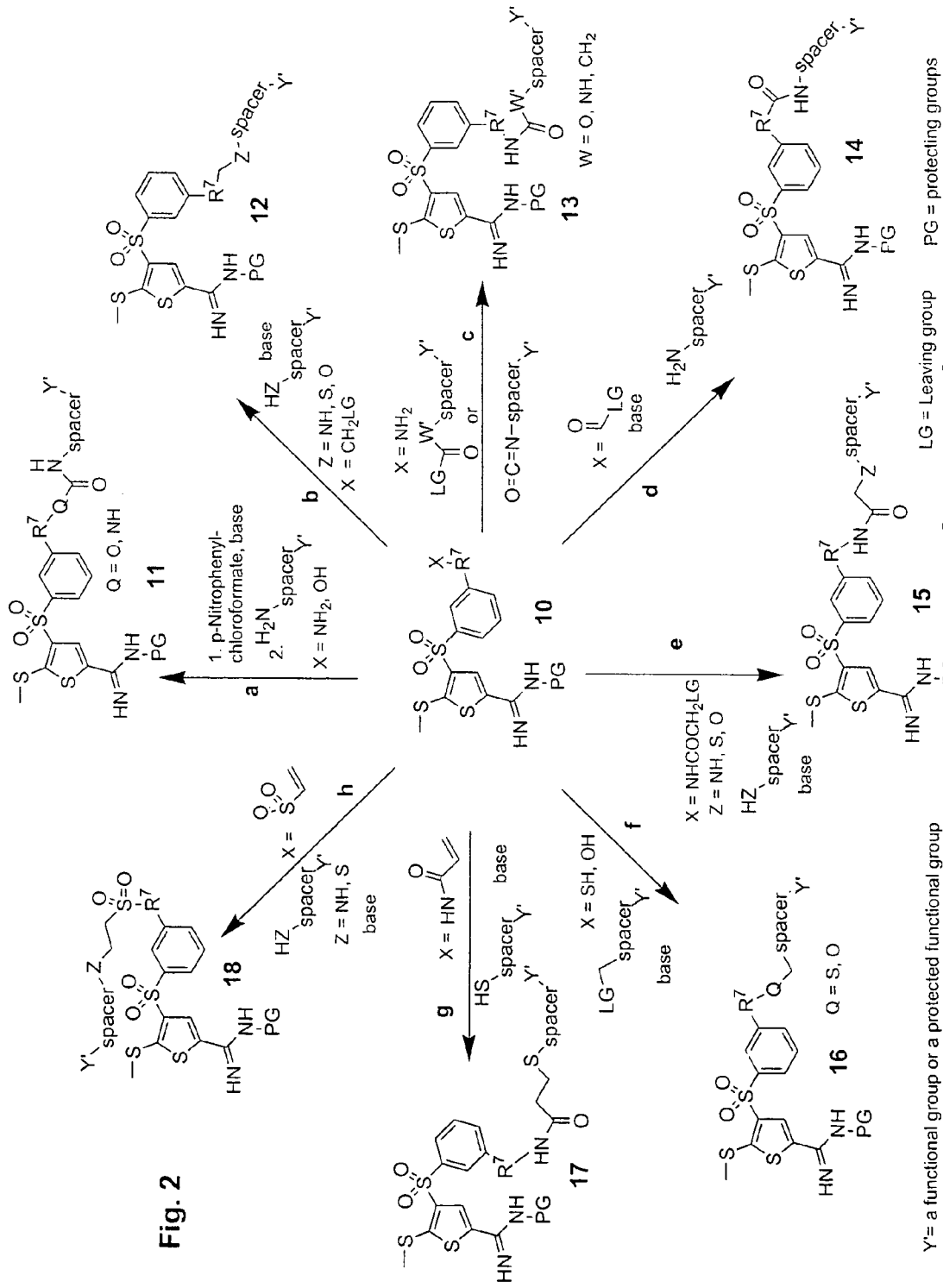
FIG. 2 is a schematic of potential reaction paths to form a drug-linker conjugate from a drug.

FIG. 2 illustrates a schematic summarizing eight methodologies that may be used to introduce a bi-functional linker onto the key scaffold 10 (U.S. provisional application 60/383130) to provide a suitable handle for conjugation on intermediates 11-18. When X=$NH_2$ or OH, scaffold 1 can be preactivated to the p-nitrophenylcarbamate or p-nitrophenylcarbonate, respectively by treating with p-nitrophenylchloroformate in the presence of a base such as pyridine. This in-situ generated intermediate is immediately reacted with a suitable linker ($NH_2$-spacer-Y') in the presence of a base, preferably triethylamine or diisopropylethylamine to generate the urea or carbamate 11 (path a). When X=NH2, scaffold 10 can be directly reacted with a linker containing an activated-carbamate, or isocyanate to give an urea 13 (W'=NH). When X=NH2, scaffold 10 can also be treated with a linker containing a carbonate or an activated acid functionality (or acid chloride), to give respectively a carbamate 13 (W'=O) or an amide 13 (W'=CH2). In another variation of this route, a nucelophile (X=SH or OH) on scaffold 10 may be alkylated by displacing a good leaving group on the linker in a nucleophilic substitution reaction to produce intermediate 16 (path f). Additionally, a good leaving group (preferably, LG=Cl, Br, I, p-nitrophenol, methylsulfonate, or p-toluenesolfonate) on scaffold 10 may be used to alkylate a suitable bifunctional liker to provide intermediates 12 or 15 (as described in paths b and e, respectively), where Z=NH, S, or O. Alternatively when X is an acid chloride or an activated acid this can be treated with an amine containing linker as shown in path d to give an amide 14. In path d, the activated acid can be generated in situ by treating with a number of standard peptide coupling reagents, preferably DIC/DMAP. Finally, the conjugation of scaffold 10 and the linker may be accomplished by carrying out a conjugative addition with a suitable Michael acceptor incorporated into X. Thus, reaction of a linker bearing a suitable nucleophile (Z=NH or S) with an acrylamide or vinyl sulfone, in the presence of a base, furnishes the desired intermediates 17 or 18 (as described in path g and h, respectively).

Figure 3:
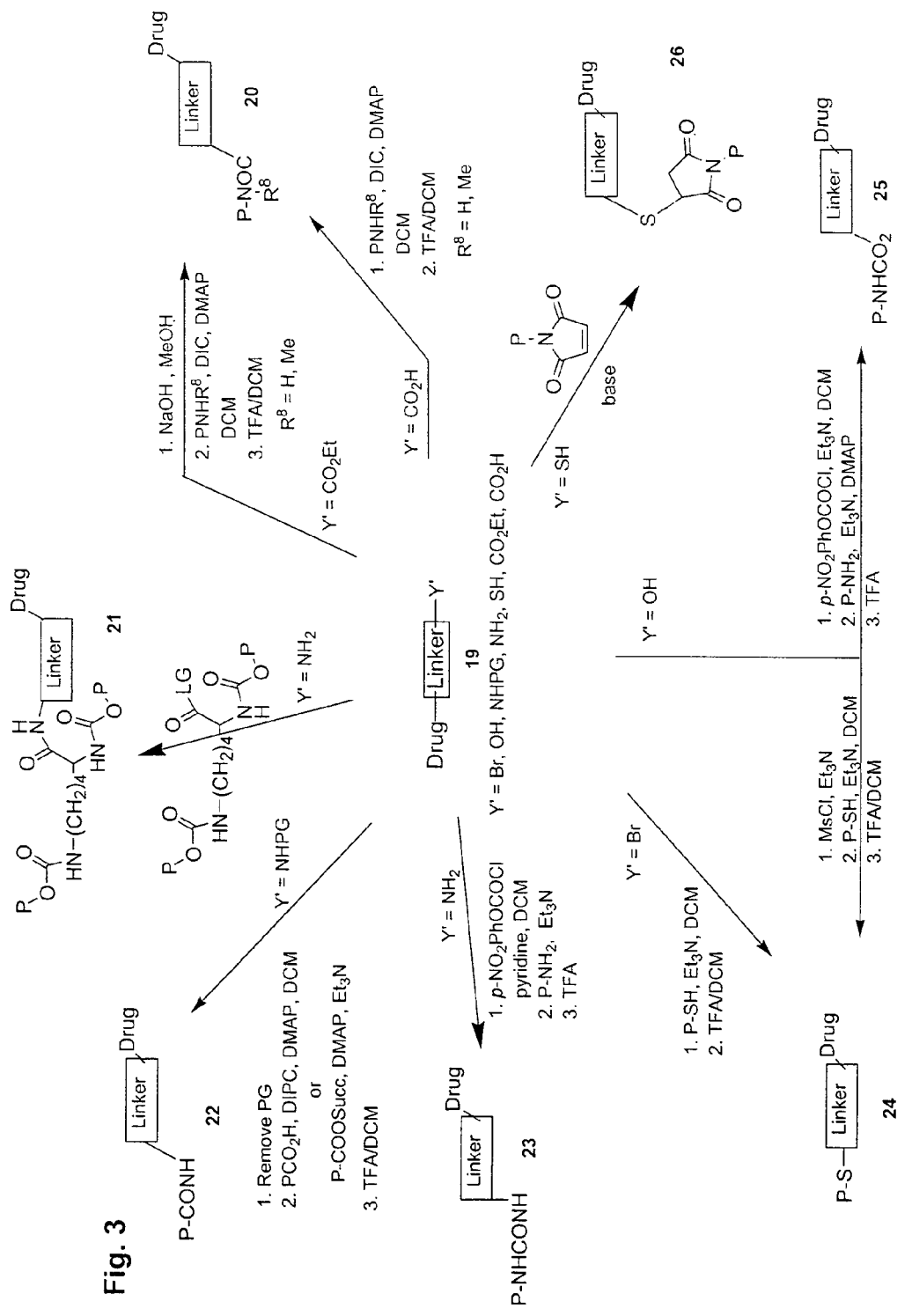
FIG. 3 is a schematic of potential reaction paths to attach a drug-linker conjugate to a polymer.

FIG. 3 illustrates a schematic summarizing nine strategies for PEG attachment to the linker-drug complex, such as those intermediates described above.

One general conjugation strategy involves amide bond formation between the drug-linker 19 and the PEG reactive functional group (—$NH_2$ or —$CO_2H$). For example, when Y'=$CO_2H$, a carbodiimide coupling in the presence of PEG-amine and stochiometric DMAP gives 20 (following deprotection with TFA in DCM). Other coupling reagents such as HBTU, PyBop, or DPPA may be used as well. When Y' is a carboxylic ester, hydrolysis of the ester gives the carboxylic acid which can be coupled to PEG-amine as previously described. Alternatively, a linker containing an amine functionality (Y'=$NH_2$) can be coupled to a PEG-carboxylic acid by similar amidation reagents, giving 22 (monomeric PEG) or 21 (multiple PEG units). Commercially available PEG-activated esters (e.g. PEG-CO-N-hydroxysuccinimidyl ester) may be used for this purpose as well.

A second general strategy for linking PEG to a drug-linker complex involves nucleophilic thiol addition or substitution to an appropriate electrophile, giving a sulfide bond. For example, a thiol-containing PEG can react with a linker containing a halide (Y'=Br) or a mesylate (synthesized from Y'=OH), to give 24. Alternatively, a thiol-containing linker can add to a maleimide group on the PEG to give 26. In each of these cases, the functional groups on the reactive partners could be reversed (linker vs. PEG) as well.

A third general strategy for conjugation involves formation of a urea or carbamate between the PEG and linker. For example, when the drug-linker complex 19 contains an amine functionality (Y'=$NH_2$), an activated carbamate can be formed using a reagent such as p-nitrophenyl chloroformate with an amine base [*J. Med. Chem.* 38, 3236-3245 (1995)]. This activated carbamate can be reacted with PEG-amine, to give 23. Similarly, when Y'=OH, an activated carbonate can be formed using a reagent such as p-nitrophenyl chloroformate. Reaction of this carbonate intermediate with PEG-amine yields 25. Again, in each of these cases, the functional groups on the reactive partners could be reversed (linker vs. PEG).

Figure 4:
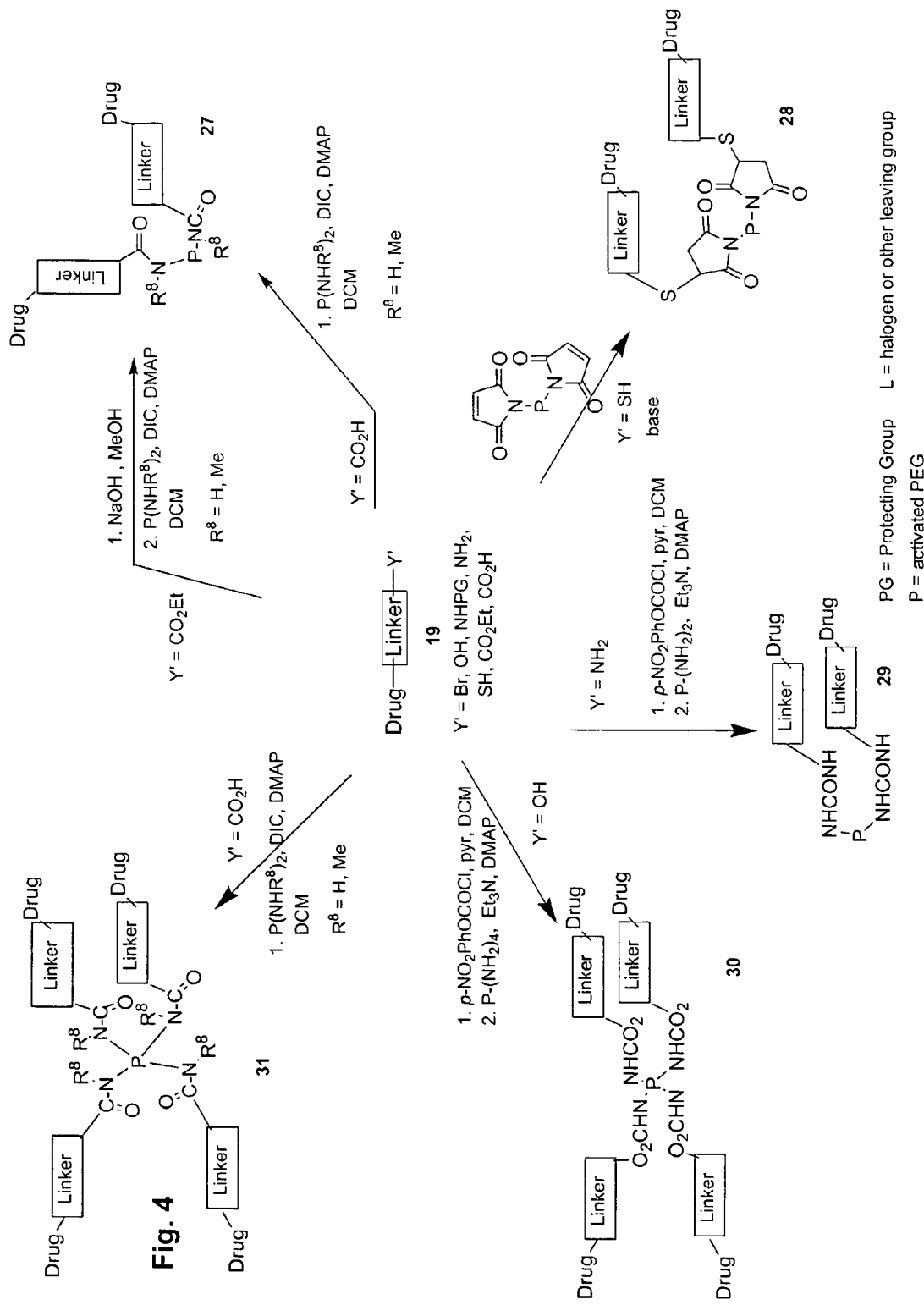
FIG. 4 is a schematic of potential reaction paths to attach multiple drug-linker conjugates to a polymer.

FIG. 4 depicts some representative strategies for synthesizing multiple drug-linker moieties per PEG unit (such as when n=2 or n=4 in formula (I)). In one embodiment, the PEG moiety may simply be functionalized at each end of the PEG ((e.g.: $H_2NCH_2CH_2$—$(OCH_2CH_2)_n$—$CH_2CH_2NH_2$) a bifunctionalized PEG) or may contain various branches to the PEG construct (e.g.: tetrabranched PEG). The linkage chemistries involved are analogous to those described with respect to FIG. 3. For example, bifunctional amine-PEG (PEG-$(NH_2)_2$) can be coupled with excess 19 (Y'=$CO_2H$) to give the bis-functional moiety 27. Similarly, multiply functionalized amine-PEG (PEG-$(NH_2)$n) can be reacted with an activated carbamate (synthesized from 19 Y'=$NH_2$) or carbonate (synthesized from 19 Y'=OH) to give 29 and 30, respectively. Alternatively, PEG functionalized with reactive maleimide moieties can be reacted with 19 (Y'=SH) under basic conditions to give 28. Furthermore branched PEG with multiple carboxylic acid groups can be coupled to 19 (Y'=NHR (R=H, Me) using standard amid-bond forming conditions to give 31.

The methodologies used to carry out the strategies described FIGS. 1-4 are conventional to those trained in the art of organic and peptide chemistry.

For example, forming amides or esters from amines or alcohols, respectively was typically accomplished using a DIC/DMAP combination (where racemization was not a concern) or using a HBTU/HOBT combination where racemization of an α-center of an amino acid was a potential problem. This can also be accomplished using a number of other standard condensing agents (EDC, PyBOP, HATU, TBTU, HOBT/activated ester or DIC/HOBT). (1) Bodanszky, M.; The Practice of Peptide Synthesis: Springer-Verlag: New York, 1984. (2) Bunin, B.; The Combinatorial Index:Academic Press: New York, 1998. (3) *J Org Chem.* 1999, 64(22): 8063-8075. Urea formation was generally accomplished by reaction of an amine with an isocyanate or activation with p-nitrophenyl chloroformate followed by reaction with a second amine (1) *J. Med. Chem.* 1995, 38, 3236-3245. Conjugative addition and thiol addition to maleimides was carried out as previously described (1) *J. Am. Chem. Soc.* 1999, 121, 7967-7968. (2) *Bioconjugate Chemistry.* 2003, 14(2):464-72. (3) Nat Struct Biol. 2000, 7(4):309-11. (4) Mar., J.: Advanced Organic Chemistry: Reactions, Mechanisms, & Structure: Wiley: New York, 1992.

Figure 5:
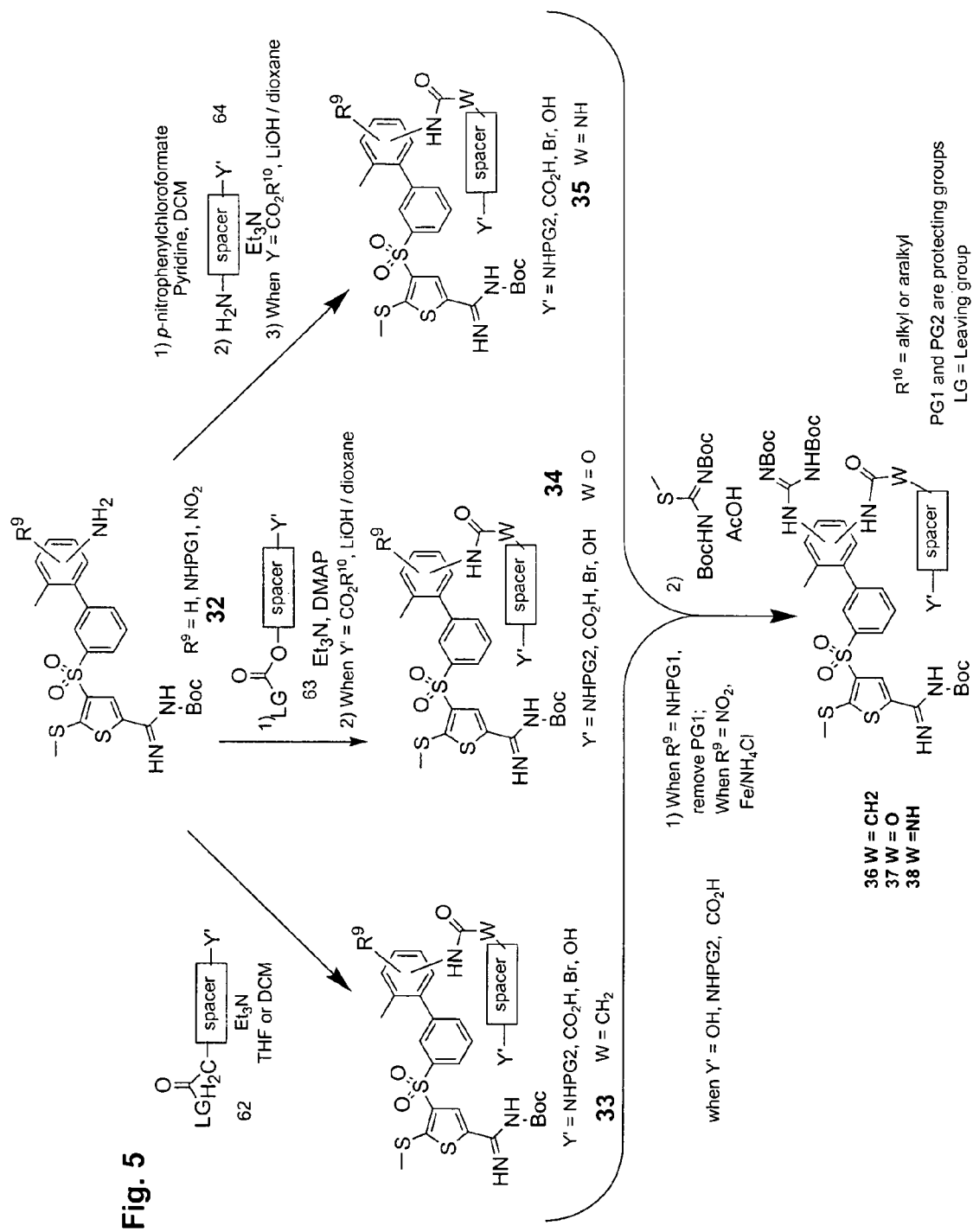
FIG. 5 is a schematic of potential reaction paths to form a drug-linker conjugate from a drug.

Turning now to FIG. 5, an aniline 32 (described in U.S. Ser. No. 60/383,130) can be coupled to a linker 62, 63 or 64 in the manner described in FIG. 2 to give the corresponding amide 33, carbamate 34 and urea 35. When $R_9$ in compounds 33, 34 and 35 is a protected amine and Y' is OH, protected amine or carboxylic acid, protecting group on $R_9$ can be removed and further reacted with bis-Boc protected S-methylisothiourea (Aldrich Chemical Company, Milwaukee, US) to give the guanidines 36, 37 and 38. When $R_9$ is a nitro group, this can be reduced to an amine and treated in a similar manner to give compounds 36, 37 and 38.

Figure 6:
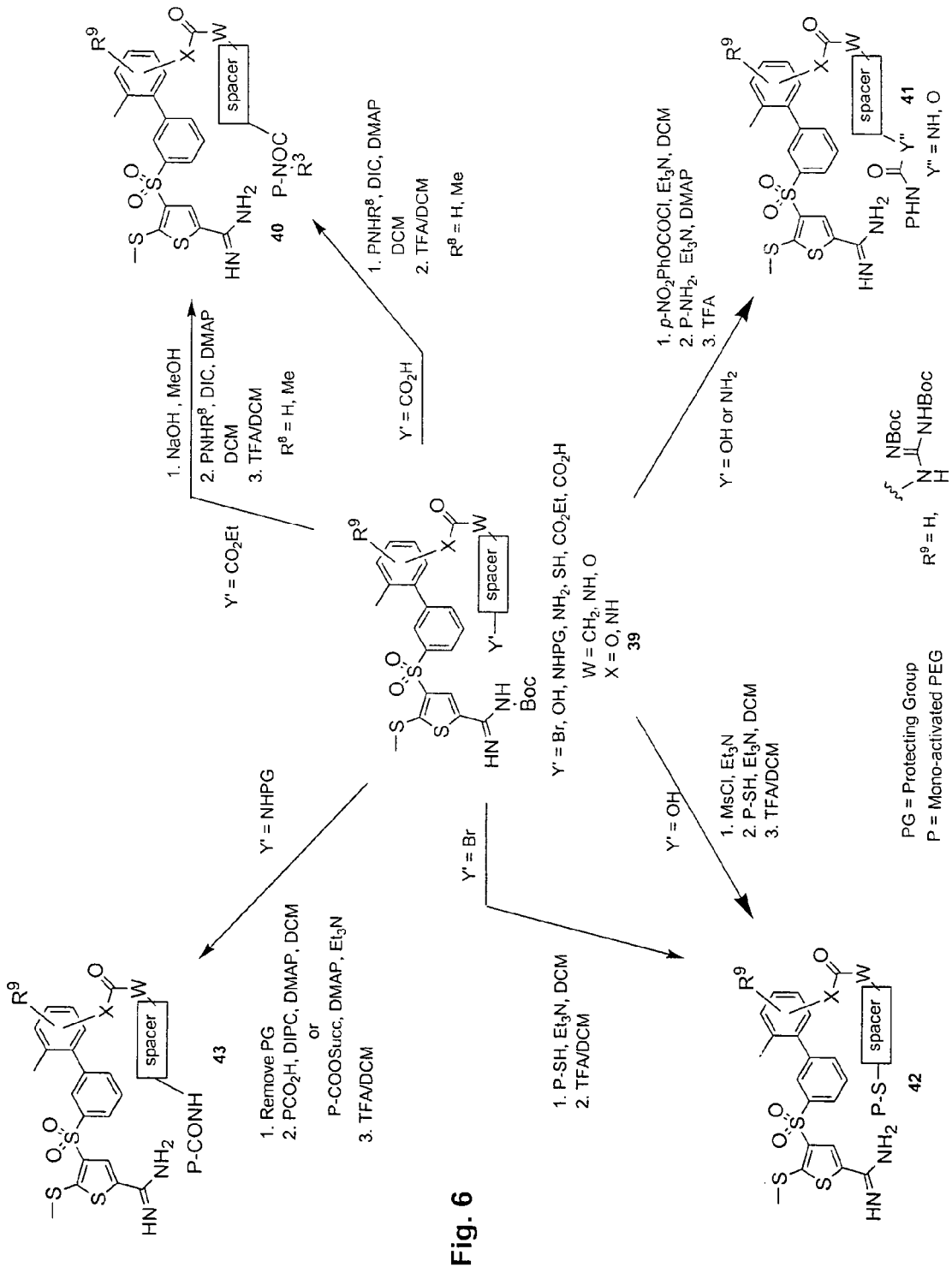
FIG. 6 is a schematic of potential reaction paths to attach a drug-linker conjugate to a polymer.

Turning now to FIG. 6, a biarylthiophene amidine (described in U.S. Ser. No. 60/383,130) coupled to a linker to form compound 39 can be attached to a PEG molecule via several methods. For example, when Y'=$CO_2H$, a carbodiimide coupling in the presence of PEG-amine (PEG-$NH_2$) and stoichiometric DMAP gives 40 (following deprotection with TFA in DCM). Other coupling reagents such as HBTU, PyBop, or DPPA may be used as well. When Y' is a carboxylic ester, hydrolysis of the ester gives the carboxylic acid which can be coupled to PEG-$NH_2$ as previously described. Alternatively, a linker containing an amine functionality (Y'=$NH_2$) can be coupled to a PEG-$CO_2H$ by similar amidation reagents, giving 43. Commercially available PEG-activated esters (e.g. PEG-CO-N-hydroxysuccinimidyl ester) may be used for this purpose as well.

A second general strategy for linking PEG to the drug-linker complex 39, involves nucleophilic thiol addition or substitution to an appropriate electrophile, giving a sulfide bond. For example, a thiol-containing PEG can react with a linker containing a halide (Y'=Br) or a mesylate (synthesized from Y'=OH), to give 42.

A third general strategy for conjugation involves formation of an urea or carbamate between the PEG and linker. For example, when the drug-linker complex 5 contains an amine functionality (Y'=$NH_2$), an activated carbamate can be formed using a reagent such as p-nitrophenyl chloroformate with an amine base [*J. Med. Chem.* 38, 3236-3245 (1995)]. This activated carbamate can be reacted with PEG-$NH_2$, to give 41 (Y"=NH). Similarly, when Y'=OH, an activated carbonate can be formed using a reagent such as p-nitrophenyl chloroformate. Reaction of this carbonate intermediate with PEG-$NH_2$ yields 41 (Y"=O).

Figure 7:
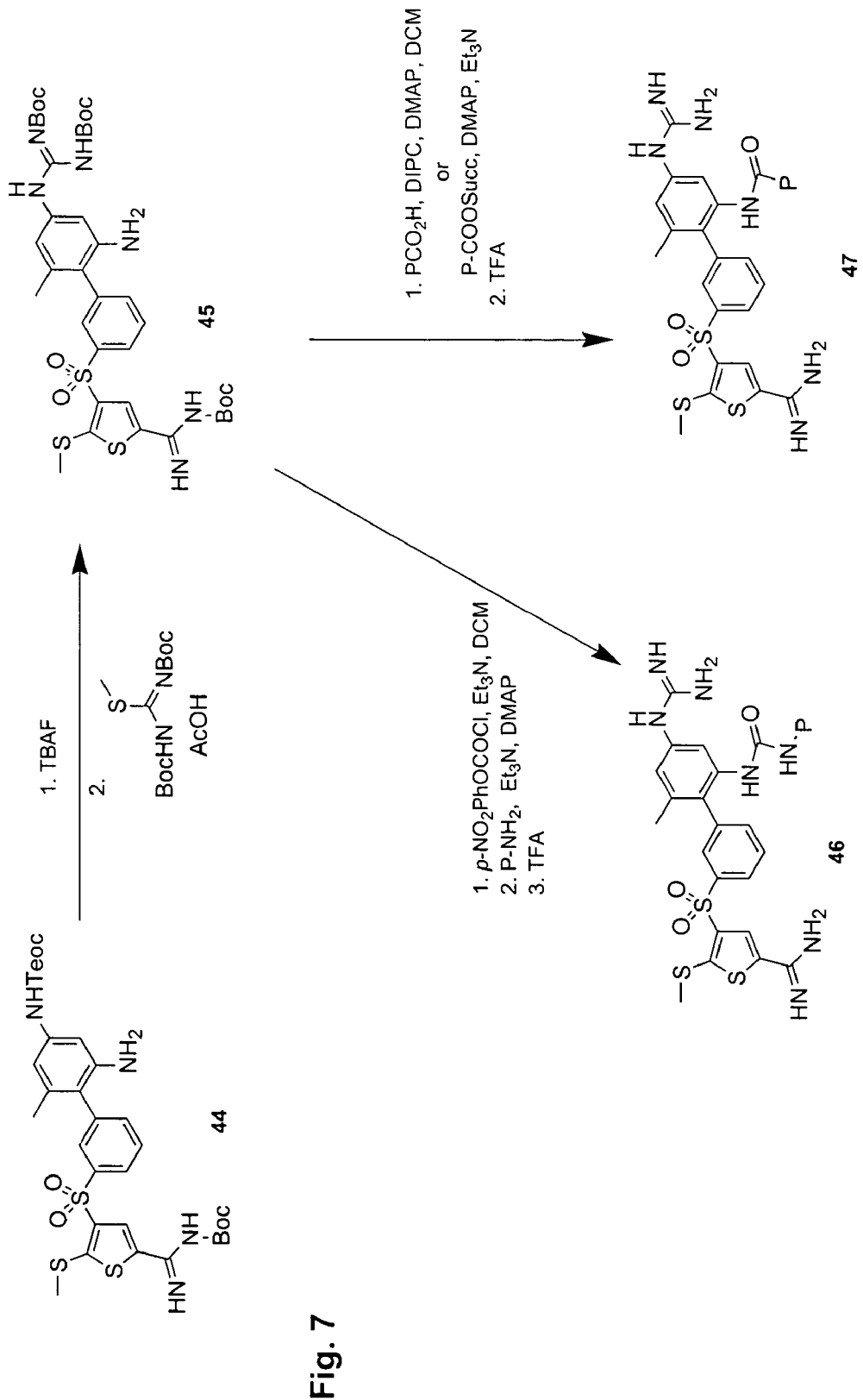
FIG. 7 is a schematic of potential reaction paths to form a drug-polymer conjugate.

FIG. 7 describes an approach to attach a PEG moiety directly to the drug molecule without a linker. This approach was used in Example 5.

The Teoc protected bis-aniline 44 (described in U.S. Ser. No. 60/383,130) is treated with TBAF and the resulting bis-aniline is treated with bis-BOC protected S-methylisothiourea (Aldrich Chemical Company, Milwaukee, US) which reacts primarily with the less sterically hindered amine to provide compound 45. Compound 45 can be treated with p-nitrophenylchloroformate followed by PEG-amine (PEG-$NH_2$) a s described with respect to FIG. 3 and deprotected with TFA to give compound 46.

Alternatively, 45 can be treated with a PEG-acid (PEG-$CO_2H$) as described with respect to FIG. 3 and deprotected with TFA to give compound 47.

Figure 8:
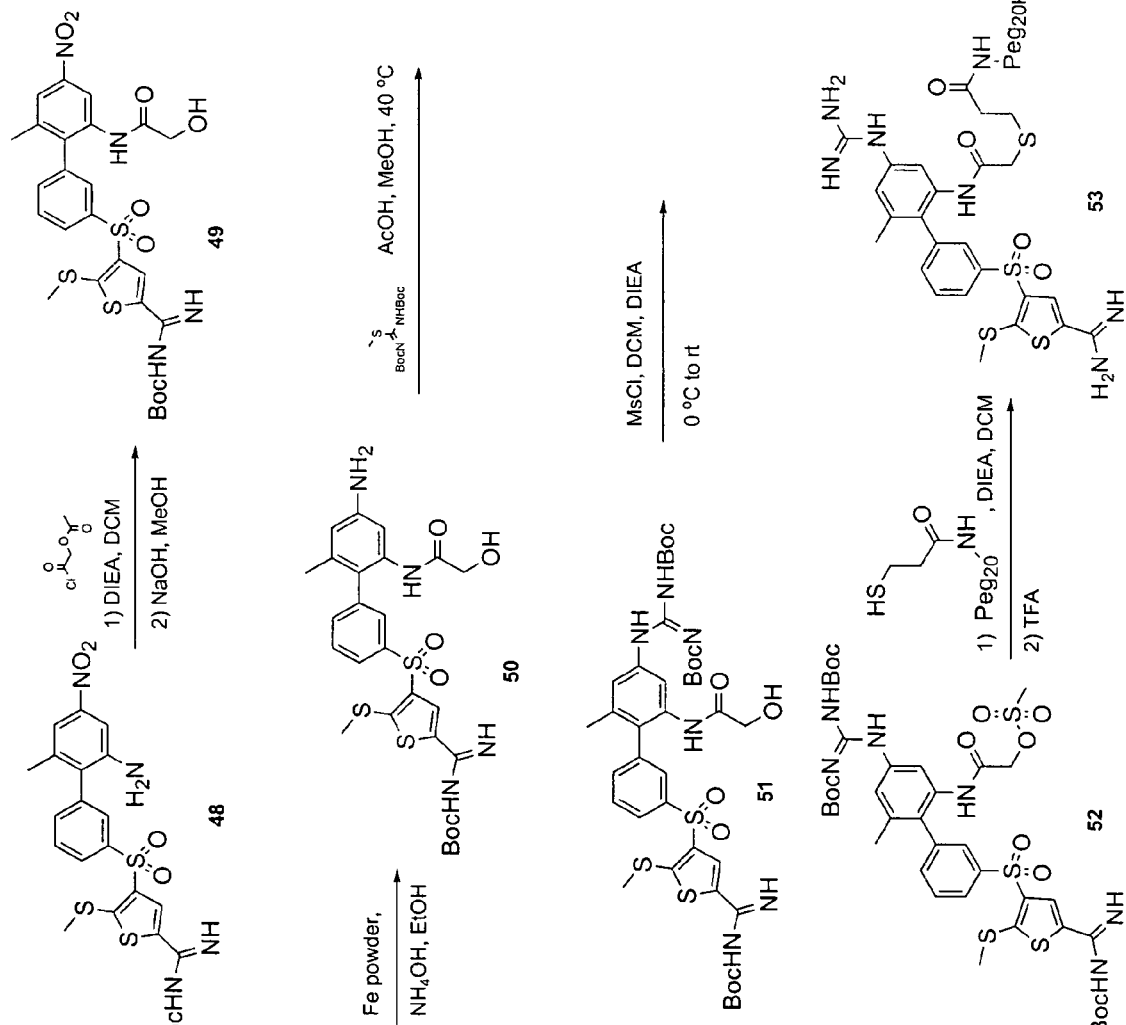
FIG. 8 is a schematic of a synthetic pathway to form a drug-linker-polymer conjugate.

FIG. 8 illustrates an alternate route for the preparation of the compound described in Example 6. Aniline 48 (described in U.S. Ser. No. 60/383,130) was acylated with acetoxyacetyl chloride in the presence of diisopropyl ethylamine followed by saponification of the acetyl group to furnish primary alcohol 49. Reduction of the nitro group of 49 followed by guanidinylation of the resulting aniline with 1,3-bis(tert-butoxycarbonyl)-2-methyl-2-thiopseudourea in acetic acid provided alcohol 51. The primary alcohol was activated with mesyl chloride. The resulting mesylate 52 was conjugated with 3-mercaptopropionamide PEG-20 KDa (Rapp Polymere). Finally, global deprotection with TFA/DCM (1:1) provided PEGylated compound 53 (Example 6, alternate route).

Figure 9:
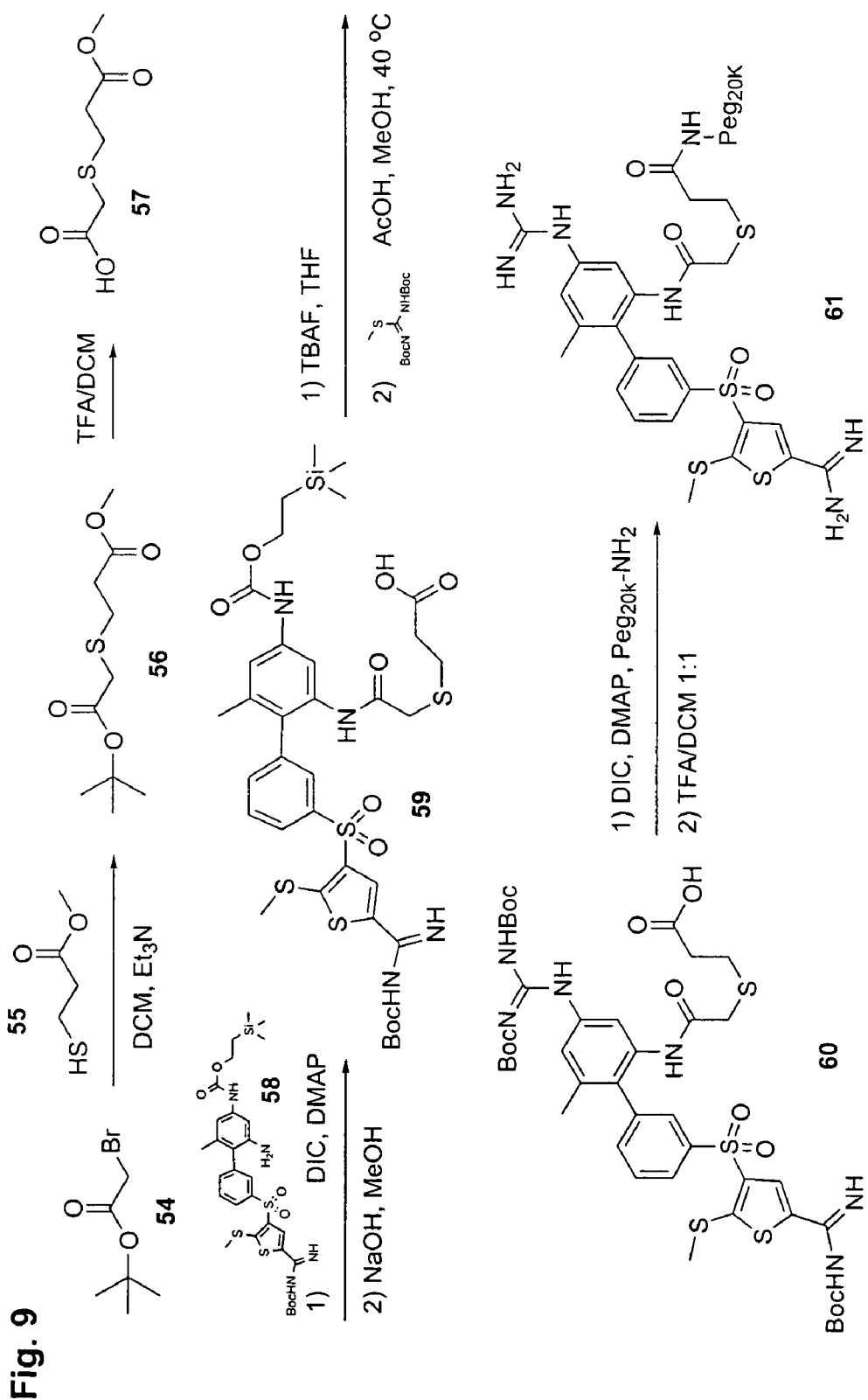
FIG. 9 is a schematic of an alternate synthetic pathway to FIG. 8.

FIG. 9 illustrates an alternate route for the preparation of the compound in Example 6. Linker 57 is prepared in two steps by alkylation of methyl 3-mercaptopropionate with tert-butyl bromoacetate followed by removal of the tert-butyl group with TFA. Linker 57 is then coupled to intermediate 58 (described in U.S. Ser. No. 60/383,130) using DIC/DMAP. Hydrolysis of the methyl ester followed removal of the Teoc protecting group with TBAF and guanidinylation as previously described provides acid 60. Conjugating to a polymer of this intermediate is accomplished using standard conditions (DIC/DMAP in DCM) followed by global deprotection with TFA to provide the desired compound 61 (Example 6).

Figure 10:
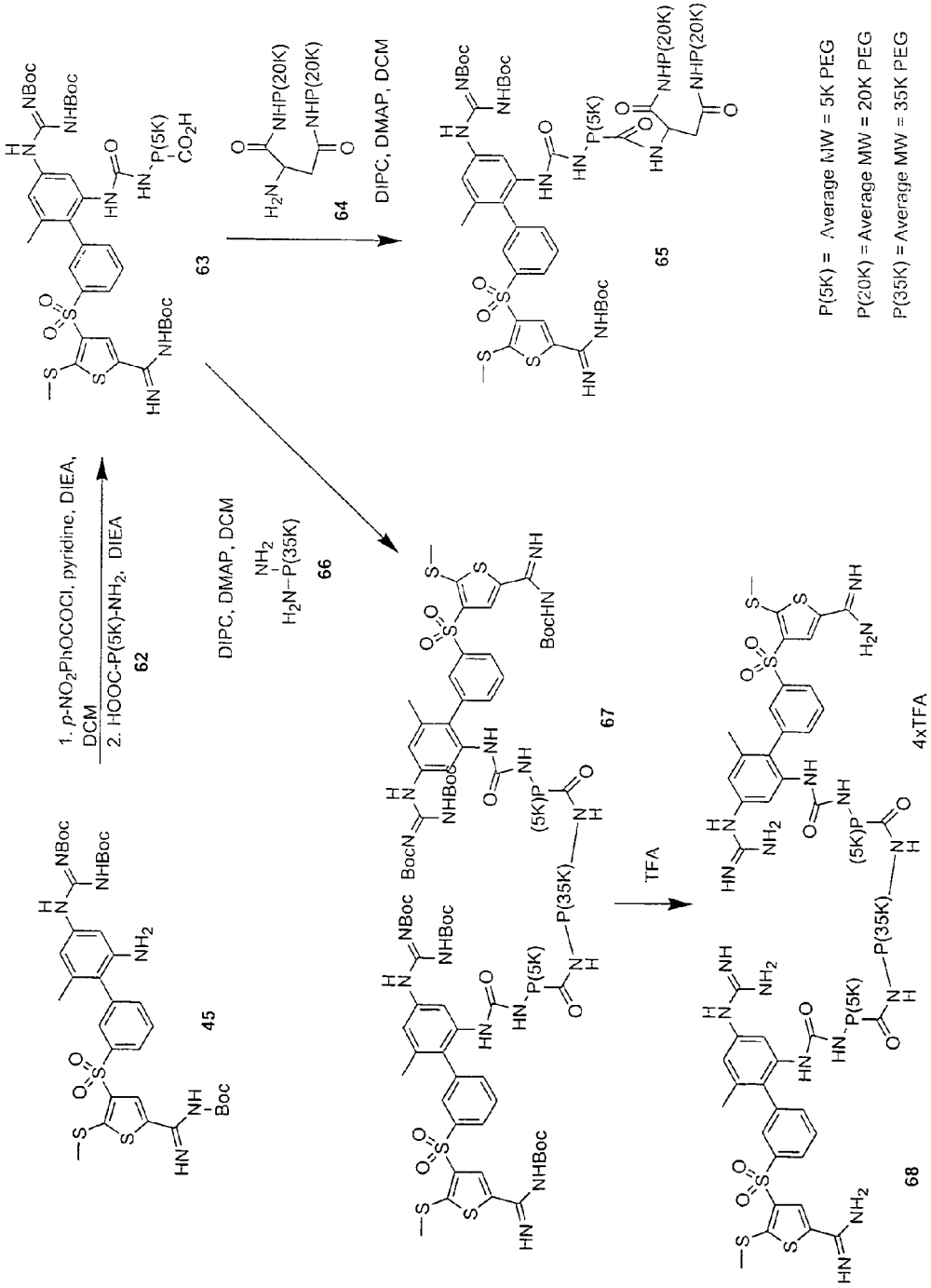
FIG. 10 is a schematic of a synthetic pathway to form mono and multivalent drug-polymer conjugates having increased average molecular weight.

FIG. 10 describes an approach to synthesize PEG-conjugates with increased average molecular weight and in particular multivalent PEG-conjugates with increased average molecular weight (>35K). The intermediate 45 can be converted to an activated carbamate by using a reagent such as p-nitrophenyl chloroformate with an amine base [J. Med. Chem. 38, 3236-3245 (1995)]. This activated carbamate can be reacted with a bis-functionalized PEG such as compound 62 to give a PEG conjugate 63, with a free carboxylic acid terminus. This acid can be activated with diisopropylcarbodiimide in the presence of either a mono-functional PEG such as 64 to give 65 a conjugate with larger molecular weight, or in the presence of a bifunctional PEG such as compound 66 to give a bivalent PEG-conjugate 67. Compound 67 can be treated with TFA to give the active compound 68.

Figure 11:
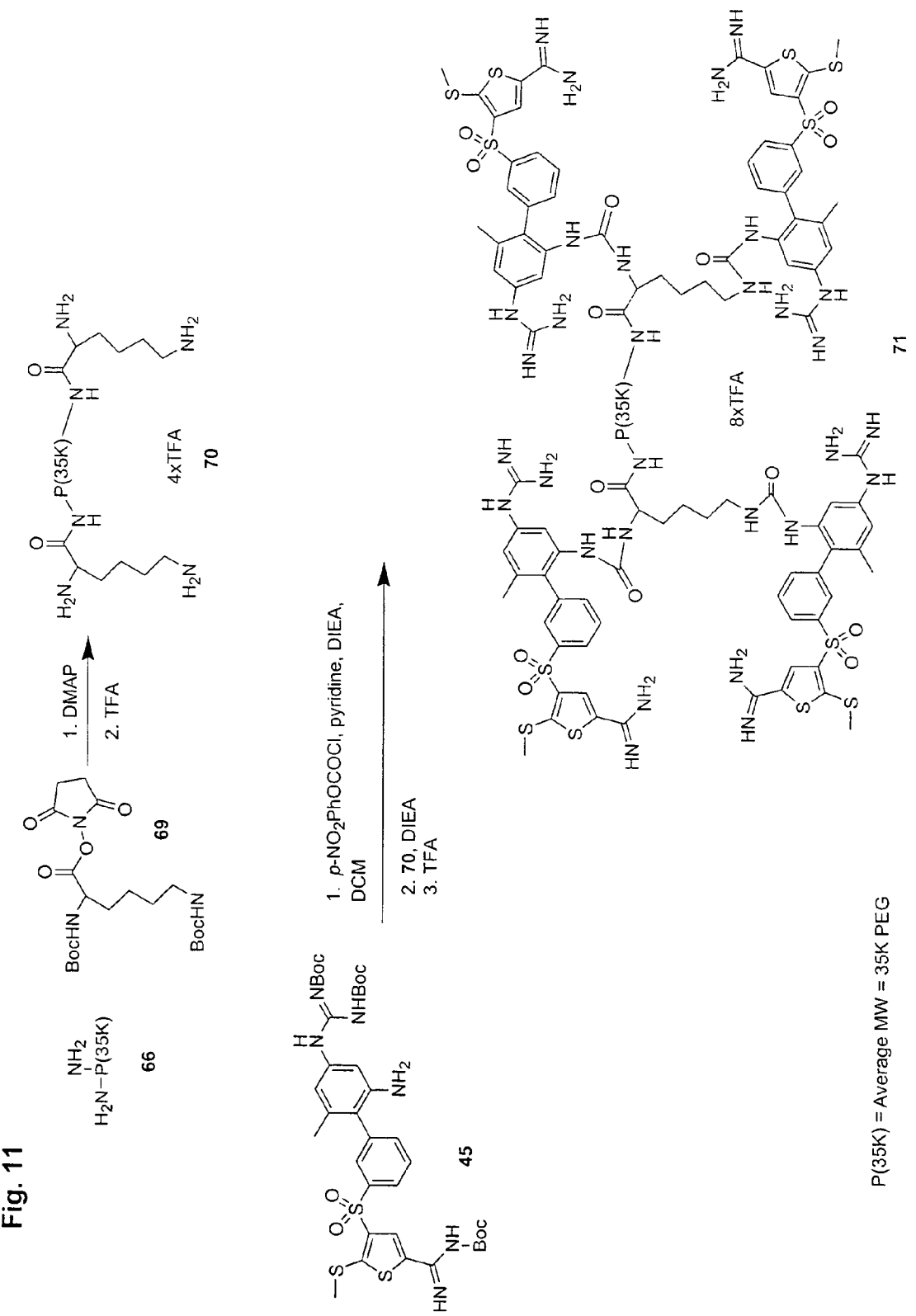
FIG. 11 is a schematic of a synthetic pathway to form a tetravalent drug-polymer conjugate.

Turning now to FIG. 11, an approach is described to synthesize multivalent PEG-conjugates. The hydroxysuccinimide ester of bis-Boc-protected lysine, 69 can be coupled to a bifunctional PEG such as 66, which upon treatment with TFA gives a tetravalent PEG species 70. The intermediate 45 can be converted to an activated carbamate by using a reagent such as p-nitrophenyl chloroformate with an amine base [J. Med. Chem. 38, 3236-3245 (1995)]. This activated carbamate can be reacted with 70 in the presence of DIEA to give a tetravelent PEG-drug conjugate, which upon treatment with TFA gives the active tetravalent PEG-drug conjugate 71.

The compounds and conjugates of the present invention may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

Compounds employed in the present methods may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred protecting groups include the benzyloxycarbonyl group and the tert-butyloxycarbonyl group. Other preferred protecting groups that may be employed in accordance with the present invention may be described in Greene, T. W. and Wuts, P. G. M., *Protective Groups in Organic Synthesis* 2d. Ed., Wiley & Sons, 1991.

Definitions

When any variable occurs more than one time in any substituent or in any formula, its definition in each occurrence is independent of its definition at every other occurrence. Thus, for example, if a group, or plurality of groups, is shown to be substituted with 0-2 Q, then said group(s) may optionally be substituted with up to two Q, and Q at each occurrence in each group is selected independently from the defined list of possible Q. Combinations of substituents and/or variables are permissible only if such combinations result in stable compounds. When a bond to a substituent is shown to cross the bond connecting two atoms in a ring, then such substituent may be bonded to any atom on the ring.

"Substantially non-hydrolyzable under physiological conditions" refers to conditions typically found in vivo in a human. Such bonds include amide, urea, carbon-carbon, carbamate, ether, thioether, thiourea, thioamide, amine, oxime, hydrazide, and ketone.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds modified by making acid or base salts. Lists of suitable salts are found in *Remington's Pharmaceutical Sciences,* 17th ed., Mack Publishing Company, Easton, Pa., 1985, p. 1418, the disclosure of which is hereby incorporated by reference.

Buffers include, for example, phosphate, citrate, sulfosalicylate, and acetate buffers. A more complete list can be found in the United States Pharmacopoeia, the disclosure of which is hereby incorporated herein by reference, in its entirety.

| Abbreviations | |
|---|---|
| PEG | Polyethylene glycol |
| TFA | Trifluoroacetic acid |
| $Et_3N$ | Triethylamine |
| THF | Tetrahydrofuran |
| EtOAc | Ethyl Acetate |

| Abbreviations | |
|---|---|
| rt | Room Temperature |
| NaOH | Sodium Hydroxide |
| $MgSO_4$ | Magnesium Sulfate |
| DCM | Dichloromethane |
| $CH_2Cl_2$ | Methylene Chloride |
| $NaHCO_3$ | Sodium hydrogen carbonate |
| MeOH | Methanol |
| TLC | Thin layer chromatography |
| AcOH | Acetic Acid |
| $H_2O$ | Water |
| $SiO_2$ | Silicon Dioxide |
| ESI-MS | Electrospray ionization mass spectroscopy |
| Boc | tert-butoxy carbonyl |
| DIC | diisopropylcarbodiimide |
| $^1$H NMR | Proton Nuclear Magnetic Resonance |
| $CDCl_3$ | Deuterated Chloroform |
| h | Hour |
| MW | Molecular weight |
| mL | Millilters |
| MeOD | Deuterated Methanol |
| mg | Milligrams |
| g | Grams |
| μL | Microliters |
| min | minute |
| HPLC | High Pressure Liquid Chromatography |
| mmol | millimole |
| mol | mole |
| DIEA | Diisopropylethyl amine |
| EtOAc | Ethyl acetate |
| NH4Cl | Ammonium chloride |
| EtOH | Ethanol |
| $Na_2CO_3$ | Sodium Carbonate |
| PTLC | Preperative Thin Layer Chromotography |
| $Et_2O$ | Diethyl ether |
| RP-HPLC | Reverse Phase High Pressure Liquid Chromatography |
| DMAP | 4-Dimethylaminopyridine |
| HBTU | O-benzotriazol-1-yl-N,N,N',N,'-tetramethyluronium hexafluorophosphate |
| HOBT | 1-Hydroxybenzotriazole hydrate |
| EDC | 1-(3-Dimethlyaminopropyl)-3-ethylcarbodiimide hydrochloride |
| HATU | O-(7-Azabenzotriazol-1-yl)-N,N,N',N,'-tetramethyluronium hexafluorophosphate |
| TBTU | 2-(1H-Benzotriazole-1-yl)-1,1,3,3-tetramethyluronium tetrafluoroborate |
| PyBOP | Benzotriazole-1-yl-oxy-tris-pyrrolidino-phosphonium hexafluorophosphate |
| DPPA | Diphenylphosphoryl azide |
| DIPC | 2-Dimethylaminoisopropyl chloride hydrochloride |
| Ms-Cl | Mesyl chloride |
| NaOH | Sodium hydroxide |
| Teoc | Ttrimethylsilylethoxycarbonyl |
| DMSO | Dimethylsulfoxide |
| $H_2SO_4$ | Sulfuric Acid |
| $HNO_3$ | Nitric Acid |
| HCl | Hydrochloric Acid |
| aq | Aqueous |
| Hex | Hexanes |
| $CH_3CN$ | Acetonitrile |
| $KNO_3$ | Potassium nitrite |
| $Pd(PPh_3)_4$ | Tetrakistriphenylphosphine palladium (0) |
| LCMS | Liquid Chromotography Mass Spectrophometry |
| $K_2CO_3$ | Potassium Carbonate |
| PEG 20K | 20,000 dalton Polyethylene glycol |
| TBAF | Tetrabutylammonium fluoride |
| DTNB | 5,5'-Dithiobis(2-nitrobenzoic acid) |
| $CD_3OD$ | Deuterated Methanol |
| PG | Protecting Group |
| LG, $LG_1$, $LG_2$ | Leaving Group |

The present invention is further described in the following examples.

EXAMPLES

Example 1 mPEG$_{20K}$ Amide of 11-[3'-(5-Carbamimidoyl-2-methylsulfanyl-thiophene-3-sulfonyl)-4-guanidino-6-methyl-biphenyl-2-ylcarbamoyl]-undecanoic acid bis-trifluoroacetate

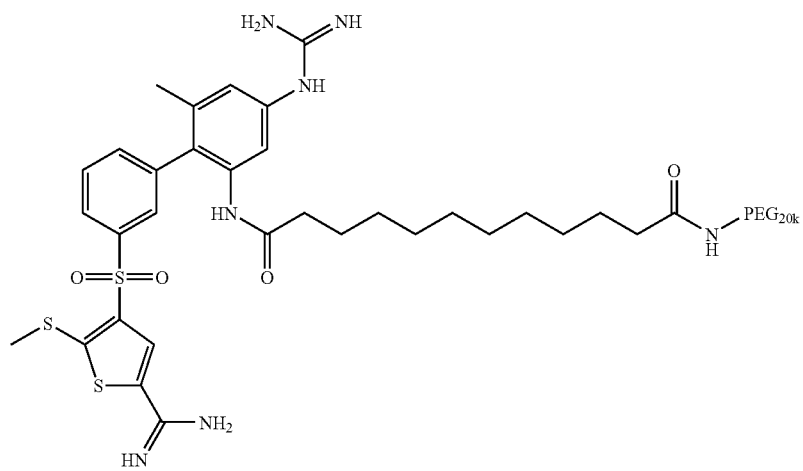

a) 8-Methyl-1H-benzo[d][1,3]oxazine-2,4-dione

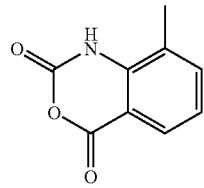

To a solution of 2-amino-3-methylbenzoic acid (9.07 g, 60 mmol) in THF (60 mL) was added simultaneously diisopropylethylamine (20.9 mL) and a solution of triphosgene (5.94 g, 20 mmol) in dichloromethane (60 mL) over 30 minutes period. After the addition was completed, the mixture stirred at ambient temperature for 16 hours. Solid was filtered and washed with ether (2×100 mL) and H$_2$O (3×50 mL), and dried in high vacuum to afford the title compound (10.02 g, 94% yield) as a white solid. $^1$H NMR (DMSO): δ 11.02 (s, 1H), 7.76 (d, 1H, J=7.7 Hz), 7.57 (d, 1H, J=7.5 Hz), 7.17-7.13 (m, 1H), 2.32 (s, 3H).

b) 8-Methyl-6-nitro-1H-benzo[d][1,3]oxazine-2,4-dione

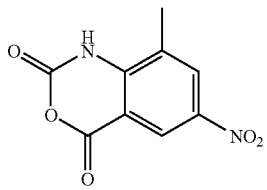

To a flask charged with 8-methyl-1H-benzo[d][1,3]oxazine-2,4-dione ((Example 1: step a) 9.27 g, 52.4 mmol) in an ice-water bath was added concentrated H$_2$SO$_4$ (90 mL) over 5 minutes period. After stirring for 10 minutes, fuming HNO$_3$ (2.9 mL) was added over 15 minutes. The reaction mixture was stirred for further 30 minutes in the ice-water bath, 30 minutes at ambient temperature, then slowly poured into ice with stirring. The solid was collected, washed with H$_2$O (3×50 mL), and dried in high vacuum to give the title compound (10.4 g, 89% yield) as a yellow solid. $^1$H NMR (DMSO-d$_6$): δ 11.65 (br s, 1H), 8.46-8.43 (m, 2H), 2.44 (s, 3H).

c) 2-Amino-3-methyl-5-nitro-benzoic acid methyl ester

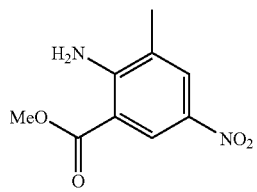

To a suspension of 8-methyl-6-nitro-1H-benzo[d][1,3]oxazine-2,4-dione ((Example 1: step b) 1.04 g, 4.68 mmol) in methanol (30 mL) was added a solution of sodium methoxide (0.5 M, 0.94 mL, 4.7 mmol) in methanol. The mixture was stirred at ambient temperature for 1 hour and neutralized by addition of saturated NH$_4$Cl. Methanol was removed under reduced pressure and the resulting mixture was filtered. The solids were washed with H$_2$O (twice), dried in high vacuum to give the product (0.97 g, 99% yield) as a yellow solid. $^1$H NMR (DMSO d$_6$): δ 8.48 (d, 1H, J=2.7 Hz), 8.02-8.01 (m, 1H), 7.75 (br s, 2H), 3.86 (s, 3H), 2.20 (s, 3H).

d) 2-Bromo-3-methyl-5-nitro-benzoic acid methyl ester

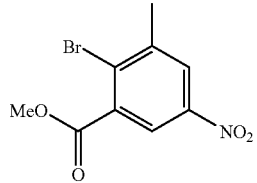

To a flask charged with copper (II) bromide (7.40 g, 33.1 mmol) was added a solution of t-butyl nitrite (4.50 mL, 37.9 mmol) in MeCN (30 mL) at ambient temperature. After stirring for 5 minutes, a suspension of 2-amino-3-methyl-5-nitro-benzoic acid methyl ester ((Example 1: step c) 4.97 g, 23.7 mmol) in MeCN (50 mL) was added. The mixture was stirred at ambient temperature for 15 minutes, 65° C. for 20 minutes, then cooled back to ambient temperature. The reaction was filtered and the filtrate was concentrated to give a dark brown solid. The solid was triturated with hexane, filtered, and washed with hexane (4×50 mL). All hexane layers were combined and concentrated to give the title product (5.7 g, 88% yield) as a pale yellow solid. ¹H NMR (CDCl₃): δ 8.35 (d, 1H, J=2.5 Hz), 8.21 (d, 1H, J=2.9 Hz), 3.99 (s, 3H), 2.59 (s, 3H).

e) 2-Bromo-3-methyl-5-nitro-benzoic acid

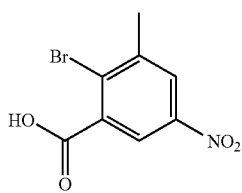

To a solution of 2-bromo-3-methyl-5-nitro-benzoic acid methyl ester ((Example 1: step d) 5.04 g) in ethanol (50 mL) was added a solution of aq NaOH (4M, 10.1 mL, 40.5 mmol) and stirred at ambient temperature for 16 h. The resulting red colored solution was concentrated to dryness, dissolved in a minimum amount of H₂O, and acidified with 1 N HCl to pH 3-4. The solid was filtered, washed with H₂O (3×50 mL) dried under high vacuum to afford the title compound (4.5 g, 94% yield) as a pale yellow solid. ¹H NMR (DMSO): δ 8.36-8.35 (m, 1H), 8.24-8.23 (m, 1H), 2.53 (s, 3H).

f) (2-Bromo-3-methyl-5-nitro-phenyl)-carbamic acid tert-butyl ester

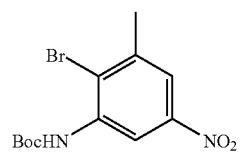

Diphenylphosphorylazide (453 μL, 2.1 mmol)was added to a stirred solution of 2-bromo-3-methyl-5-nitro-benzoic acid ((Example 1: step e) 520 mg, 2 mmol) and triethylamine (1.4 mL, 2.1 mmol)in tert-butanol (25 mL) at rt. After 15 minutes, the reaction was heated to 80° C. for 16 h. EtOAc (100 mL) was added and the solution was extracted with solutions of citric acid (3×30 mL), NaHCO₃ (2×30 mL) and brine (50 mL). Purification by column chromatography yielded the title compound as a white solid. ¹H NMR (CDCl₃): δ 8.93 (d, 1H, J=2.6 Hz), 7.77 (app dd, 1H, J=0.7, 2.8 Hz), 7.26 (br s, 1H), 2.51 (s, 3H), 1.55 (s, 9H).

g) 2-Bromo-3-methyl-5-nitro-phenylamine

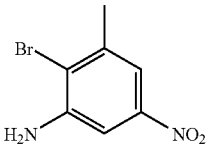

2-Bromo-3-methyl-5-nitro-phenyl)-carbamic acid tert-butyl ester ((Example 1: step f) 435 mg, 1.32 mmol) was dissolved in 10 mL of a 1:1 mixture of trifluoroacetic acid and DCM (10 mL total). After stirring for 1 h, the solvent was removed in vacuo and the yellow solid residue (306 mg) was used without further purification. ¹H NMR (CDCl₃): δ 7.46 (d, 1H, J=2.8 Hz), 7.42 (d, 1H J=2.8Hz), 6.62 (br s, 2H), 2.42 (s, 3H).

h) {[4-(6'-Amino-2'-methyl-4'-nitro-biphenyl-3-sulfonyl)-5methylsulfanyl-thiophen-2-yl]-imino-methyl}-carbamic acid tert-butyl ester A flask with a stirbar was charged with {[4-(3-dihydroxyboranyl-benzenesulfonyl)-5-methylsulfanyl-thiophen-2-yl]-imino-methyl}-carbamic acid tert-butyl ester (U.S. provisional application 60/383130 (752 mg, 1.65 mmol), 2-bromo-3-methyl-5-nitro-phenylamine ((Example 1: step g) 306 mg, 1.32 mmol), aqueous Na₂CO₃ (2M, 4 mL, 8 mmol), ethanol (4 mL) and toluene (8 mL). The solution was sparged with argon for 10 min and Pd(PPh₃)₄ (294 mg, 0.25 mmol) was added. The biphasic solution was vigorously stirred under inert atmosphere at 80° C. for 16 h, then was cooled to rt. EtOAc (40 mL) and water (20 mL) were added and the layers were separated. The organic layer was washed with saturated NaHCO₃ (2×20 mL), brine (20 mL) and was dried over sodium sulfate. Removal of the solvents in vacuo followed by column chromatography (10-40% EtOAc in hexanes) of the residue yielded the title compound (245 mg, 33%) as a yellow solid. $^1$H-NMR (CDCl$_3$): δ 8.03 (ddd, 1H, J=1.2, 2.1, 8.1 Hz), 7.91 (s, 1H), 7.90 (t, 1H, J=1.6 Hz), 7.69 (t, 1H, J=7.9 Hz), 7.53 (app dd, 1H, J=0.7, 2.3 Hz), 7.50 (dt, 1H, J=1.4, 7.7 Hz), 7.44 (app dd, 1H, J=0.5, 2.3 Hz), 3.70 (s, 2H), 2.59 (s, 3H), 2.00 (s, 3H), 1.51 (s, 9H).

i) 11-{4-Amino-3'-[5-(tert-butoxycarbonylamino-imino-methyl)-2-methylsulfanyl-thiophene-3-sulfonyl]-6-methyl-biphenyl-2-ylcarbamoyl}-undecanoic acid methyl ester

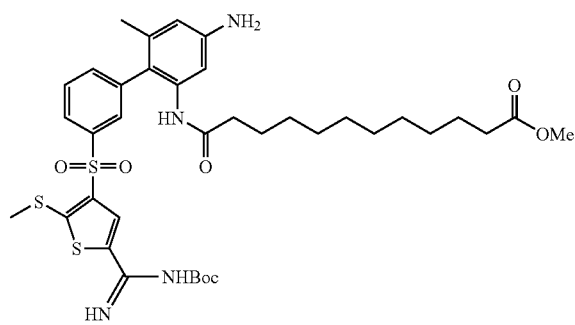

C$_{37}$H$_{50}$N$_4$O$_7$S$_3$
Exact Mass: 758.28
Mol. Wt: 759.01

Triethylamine (139 μL, 1 mmol) was added to a solution of {[4-(6'-amino-2'-methyl-4'-nitro-biphenyl-3-sulfonyl)-5-methylsulfanyl-thiophen-2-yl]-imino-methyl}-carbamic acid tert-butyl ester ((Example 1: step h) 118 mg, 0.21 mmol) in DCM (10 mL). 11-chlorocarbonyl-undecanoic acid methyl ester (73 mg, 0.26 mmol) was added dropwise over 5 min. After 30 minutes of stirring, the reaction was not complete. Additional portions of acid chloride (3×1 eq) were added in a similar manner, until the reaction was complete. Addition of EtOAc (40 mL) followed by aqueous workup with NaHCO$_3$ (2×20 mL) and brine (30 mL) yielded the crude amide (206 mg) as a glass. The residue was dissolved in EtOH (5 mL) and 4M aq NH$_4$Cl (1 mL) was added. Iron powder (165 mg, 3 mmol) was added and the reaction was heated at 75° C. for 1 h. The cooled mixture was filtered through a 0.22 um filter and solids washed with 5 mL portions of MeOH and EtOAc. Additional EtOAc (80 mL) was added and the organic solution was washed with citric acid (2×20 mL), NaHCO$_3$ (2×30 mL), water (30 mL), and brine (50 mL). Drying and concentration of the solution yielded the title compound (165 mg) which was used without further purification. ESI-MS (m/z): Calcd. for C$_{37}$H$_{50}$N$_4$O$_7$S$_3$ (M+H): 759.3; found: 759.4.

j) 11-{3'-[5-(tert-Butoxycarbonylamino-imino-methyl)-2-methylsulfanyl-thiophene-3-sulfonyl]-4-(N,N-bis-(tert-butoxycarbonylamino))guanidino-6-methyl-biphenyl-2-ylcarbamoyl}-undecanoic acid

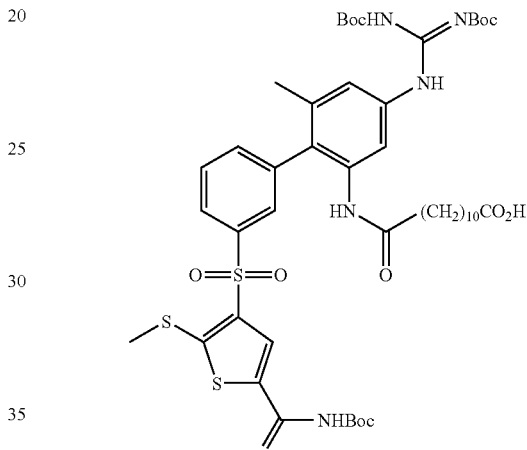

Sodium hydroxide (1M, 1 mL) was added to a solution of 11-{4-amino-3'-[5-(tert-butoxycarbonylamino-imino-methyl)-2-methylsulfanyl-thiophene-3-sulfonyl]-6-methyl-biphenyl-2-ylcarbamoyl}-undecanoic acid methyl ester ((Example 1: step i) 122 mg, 0.16 mmol) in MeOH (10 mL). The solution was stirred for 18 h at rt, the solution was quenched with AcOH (500 μL), and the solvent was removed in vacuo. The residue was dissolved in MeOH (10 mL), AcOH (500 μL), and N,N-bis(tert-butoxycarbonyl)-S-methyl-isothiourea (145 mg, 0.5 mmol) was added. The solution was stirred at 40° C. for 16 h and the solvent removed in vacuo. The residue was partitioned between EtOAc (50 mL) and water (20 mL) and the organic layer was washed with brine (20 mL). Drying and concentration of the solution yielded a residue which was chromatographed on SiO$_2$ (6:4 Hex/EtOAc, then 25:75:5 Hex/EtOAc/MeOH). The residue was further purified by RP-HPLC (C-18 column, CH$_3$CN/H$_2$O) to yield 115 mg of product). $^1$H-NMR (CD$_3$OD): δ 8.16 (s, 1H), 8.01(ddd, 1H, J=1.2, 1.9, 7.9 Hz), 7.87 (t, 1H, J=1.6 Hz), 7.65 (t, 1H, J=7.9 Hz), 7.53 (m, 1H), 7.50 (dt, 1H, J=1.4, 7.7 Hz), 7.39 (m, 1H), 2.66 (s, 3H), 2.29 (t, 2H, J=7.4 Hz), 2.05 (s, 3H), 1.93 (m, 2H), 1.61 (m, 2H), 1.53 (s, 18H), 1.49 (s, 9H), 1.0-1.40 (m, 12H), 0.94 (m, 2H).

k) mPEG$_{20K}$ Amide of 11-[3'-(5-Carbamimidoyl-2-methylsulfanyl-thiophene-3-sulfonyl)-4-guanidino-6-methyl-biphenyl-2-ylcarbamoyl]-undecanoic acid bis-trifluoroacetate

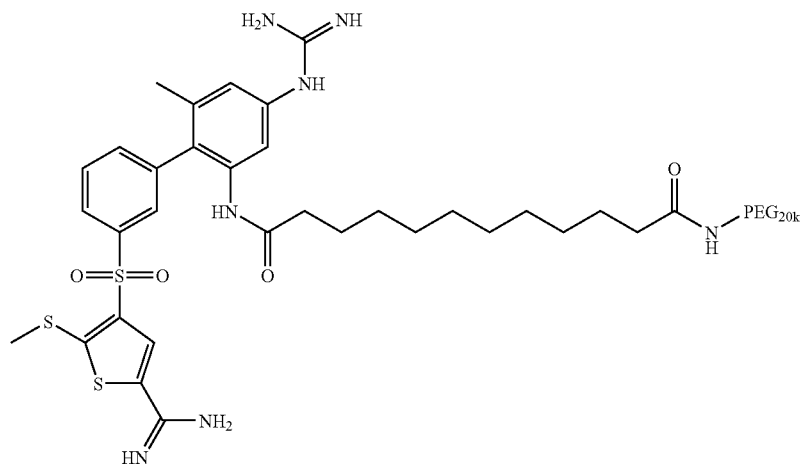

Diisopropylcarbodiimide (0.2M in DCM, 15 µL) was added dropwise to a solution of 11-{3'-[5-(tert-butoxycarbonylamino-imino-methyl)-2-methylsulfanyl-thiophene-3-sulfonyl]-4-(N,N-bis-(tert-Butoxycarbonylamino))guanidino-6-methyl-biphenyl-2-ylcarbamoyl}-undecanoic acid ((Example 1: step j) 30 mg, 0.03 mmol) and N,N-dimethylaminopyridine (4.6 mg, 0.038 mmol) in DCM (15 mL). The solution was stirred for 15 min at rt and mPEG$_{20K}$-NH$_2$ (327 mg, 0.015 mmol) was added. The solution was stirred for 18 h (ninhydrin negative after 4 h) at rt. DCM (10 mL) and MeOH (1 mL) were added followed by the slow addition of Et$_2$O (~100 mL). The solution was cooled to complete the precipitation and the solid was collected via filtration. A portion of the solid (127 mg) was dried and redissolved in 1:1 TFA/DCM. After stirring for 2 h, the solvent was removed in vacuo and dried under high vacuum. HPLC purification (C18 column, 10-55% CH$_3$CN in H$_2$O over 30 min) yielded 104 mg of pure PEGylated compound. $^1$H-NMR with PEG suppression at δ 3.62 (CDCl$_3$): δ 9.20 (s, 1H), 8.5-9.0 (H$_2$O peak), 8.37 (s, 1H), 8.22 (s, 1H), 8.07 (d, 1H, J=7.7 Hz), 7.77 (s, 1H), 7.65 (t, 1H, J=7.7 Hz), 7.53 (d, 1H, J=7.2 Hz), 7.41 (s, 1H), 7.05 (s, 1H), 7.00 (s, 3H), 3.82 (m, PEG satellite), 3.62 (m, PEG methylenes), 3.47 (m, PEG satellite), 3.39 (s, 3H, PEG-OMe terminus), 2.65 (s, 3H), 2.26 (t, 2H, J=7.2 Hz), 2.05 (s, 3H), 2.04 (m, 1H), 1.93 (m, 1H), 1.62 (m, 2H), 1.02-1.38 (m, 12H), 0.95 (m, 2H).

Example 2 mPEG$_{20K}$ Amide of 6-{3-[3'-(5-Carbamimidoyl-2-methylsulfanyl-thiophene-3-sulfonyl)-4-guanidino-6-methyl-biphenyl-2-yl]-ureido}-hexanoic acid bis-trifluoroacetate

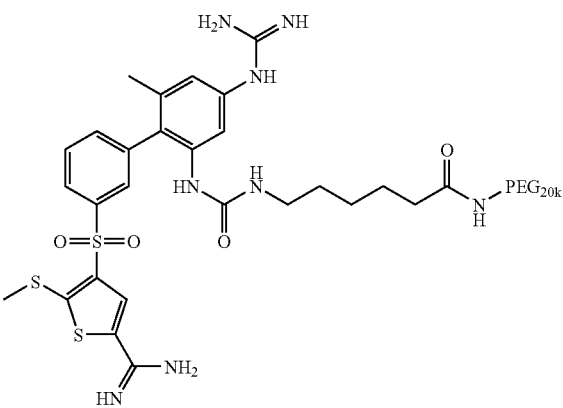

a) 4-Bromo-5-methyl-3-nitrobenzoic acid methyl ester

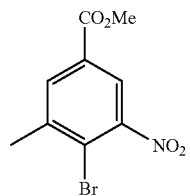

4-Bromo-3-methylbenzoic acid methyl ester (10.13 g, 44 mmol) was dissolved in a mixture of $H_2SO_4$ 120 mL and TFA (15 mL) at room temperature. The solution was cooled on an ice bath and $KNO_3$ (4.65 g, 46 mmol) was added portionwise over 30 min. the mixture was stirred at ambient temperature for 4 hours during which it warmed to rt. TLC analysis (after mini aqueous workup) showed total disappearance of starting material (30% EtOAc/Hex). The solution was poured onto ice and the aqueous slurry was extracted with EtOAc (3×150 mL). The organic layer was washed with 5% $Na_2CO_3$ (3 x 75 mL), $NaHCO_3$ (3×50 mL), water (2×100 mL), brine (100 mL), then was dried over sodium sulfate. Concentration of the solution yielded a yellowish solid/gel substance (11.6 g) which was one spot by TLC. $^1H$ NMR analysis shows two major products in ~2:1 ratio, corresponding to the o- and m-nitrobenzoate derivatives. The material was carried onto the next step without further purification.

b) 4-Bromo-5-methyl-3-nitrobenzoic acid

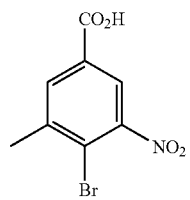

4-Bromo-5-methyl-3-nitrobenzoic acid methyl ester (Example 2: step a (11.6 g, 42.3 mmol)) was dissolved in MeOH (400 mL) at rt and 2N NaOH (43 mL) was added dropwise over 30 min via addition funnel. The solution was stirred for 12 h during which, precipitates appeared, and starting material disappeared (TLC shows only baseline spot in 30% EtOAc). The pH was adjusted to ~2 with conc HCl and the methanol was removed in vacuo. EtOAc (300 mL) was added to the aqueous slurry and the layers were separated. The aqueous layer was extracted with EtOAc (2×50 mL) and then discarded. TLC analysis of the combined organic extracts showed two products (40% EtOAc in Hexanes, 4% AcOH). The combined organic extracts were washed with a 3:1 solution of 0.5N $NaH_2PO_4$/0.5N NaOAc (~30×50 mL portions) until removal of the o-nitrobenzoic acid (lower spot on TLC, 40% EtOAc in Hex, 4% AcOH) was complete. The organic layer was then washed with brine and dried over sodium sulfate. Concentration of the solution yielded 5.4 g (47%) of a white solid. $^1H$ NMR ($CD_3OD$) δ 8.10 (m, 2H), 2.54 (s, 3H).

c) 4-Bromo-3-methyl-5-nitro-phenyl)-carbamic acid 2-trimethylsilanyl-ethyl ester

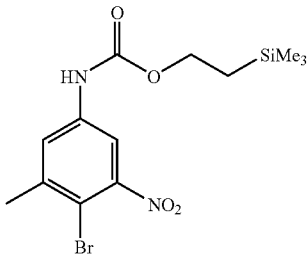

Diphenylphosphorylazide (4.31 mL, 20 mmol) was added to a stirred solution of 2-bromo-3-methyl-5-nitro-benzoic acid (Example 2: step b (5.2 g, 20 mmol)) and diisopropylethylamine (3.66 mL, 21 mmol) in 1,4-dioxane (80 mL) at rt. After 30 minutes at rt, the reaction was heated to 90° C. for 5 min. Trimethylsilylethanol (5.73 mL, 40 mmol) was added and the solution was stirred for 16 h at 95° C. The solvents were removed in vacuo and the residue was partitioned between EtOAc (100 mL) and water (30 mL). The organic layer was further washed with aqueous citric acid (3×30 mL), $NaHCO_3$, (2×30 mL) and brine (50 mL). Purification by column chromatography (9:1 Hex/EtOAc) yielded the title compound (4.1 g) as a yellow solid. $^1H$ NMR ($CDCl_3$): δ 7.73 (d, 1H, J=2.4 Hz), 7.41 (br d, 1H, J=1.7 Hz), 7.01 (s, 1H), 4.24 (m, 2H), 2.43 (s, 3H), 1.02 (m, 2H), 0.04 (s, 9H).

d) (3-Amino-4-bromo-5-methyl-phenyl)-carbamic acid 2-trimethylsilanyl-ethyl ester

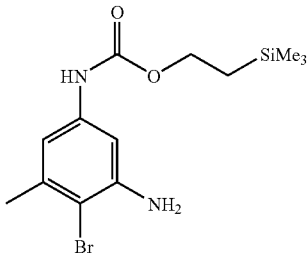

Iron powder (6.1 g, 109 mmol) was added to a suspension of (4-bromo-3-methyl-5-nitro-phenyl)-carbamic acid 2-trimethylsilanyl-ethyl ester (Example 2: step c (4.1 g, 10.9 mmol)) and $NH_4Cl$ (5.84 g, 109 mmol) in EtOH (27 mL) and water (54 mL). The reaction was heated at 85° C. for 14 h. The cooled mixture was filtered through celite and the solids were washed with 1:1 EtOAc/MeOH (200 mL). The filtrate was concentrated in vacuo and the residue was partitioned between EtOAc (100 mL) and $H_2O$ (30 mL). The organic solution was washed with water (30 mL), and brine (50 mL). Drying and concentration of the solution yielded the aniline (3.24 g, 86%) as a brown solid which was used without further purification. $^1H$ NMR ($CDCl_3$): δ 6.96 (s, 1H), 6.54 (s, 1H), 6.39 (s, 1H), 4.26 (m, 2H), 4.16 (s, 2H), 2.35 (s, 3H), 1.06 (m, 2H), 0.08 (s, 9H).

e) [3-Amino-5-methyl-4-(4,4,5,5-tetramethyl-[1,3,2]dioxaborolan-2-yl)-phenyl]-carbamic acid 2-trimethylsilanyl-ethyl ester

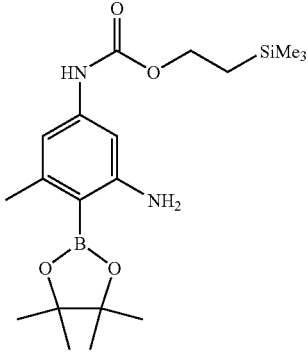

Palladium acetate (106 mg, 0.47 mmol), 2-(dicyclohexylphosphino)biphenyl (658 mg, 1.88 mmol), (3-amino-4-bromo-5-methyl-phenyl)-carbamic acid 2-trimethylsilanyl-ethyl ester ((Example 2: step d) 3.24 g, 9.38 mmol) were combined in a flask and placed under an argon atmosphere. p-Dioxane (40 mL) was added, followed by triethylamine (5.23 mL, 38 mmol) and pinacolborane (4.08 mL, 28 mmol). The solution was stirred at 80° C. for 1 h during which a ppt appeared. The solvent was removed in vacuo and the residue was partitioned between EtOAc (100 mL) and aq. NH$_4$Cl (50 mL). The organic layer was further washed with NH$_4$Cl (2×30 mL), NaHCO$_3$ (30 mL), and brine (50 mL). The organic layer was dried (MgSO$_4$), concentrated in vacuo, and the residue was purified by SiO$_2$ column chromatography (8:2 Hex/EtOAc) to afford the product (2.44 g, 66%) as a brown solid. $^1$H NMR (CDCl$_3$): δ 6.77 (s, 1H), 6.38 (s, 1H), 6.28 (d, 1H, J=1.9 Hz), 4.91 (s, 2H), 4.23 (m, 2H), 2.42 (s, 3H), 1.32 (s, 12H), 1.03 (m, 2H), 0.05 (s, 9H).

f) {6-Amino-3'-[5-(tert-butoxycarbonylamino-imino-methyl)-2-methylsulfanyl-thiophene-3-sulfonyl]-2-methyl-biphenyl-4-yl}-carbamic acid 2-trimethylsilanyl-ethyl ester

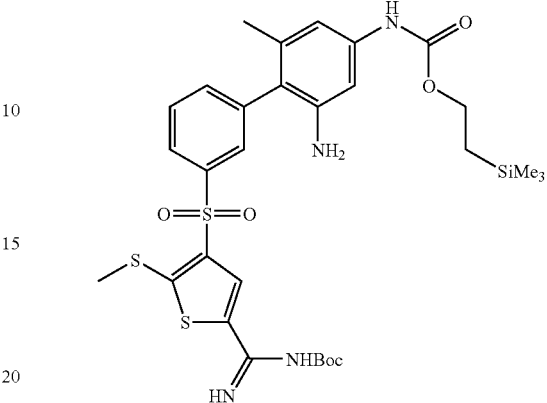

A flask with a stirbar was charged with [3-amino-5-methyl-4-(4,4,5,5-tetramethyl-[1,3,2]dioxaborolan-2-yl)-phenyl]-carbamic acid 2-trimethylsilanyl-ethyl ester (Example 2: step e (2.34 g, 5.96 mmol)), {[4-(3-bromo-benzenesulfonyl)-5-methylsulfanyl-thiophen-2-yl]-imino-methyl}-carbamic acid tert-butyl ester ((U.S. provisional application 60/383130 (2.93 g, 5.96 mmol), aqueous Na$_2$CO$_3$ (2M, 11.9 mL, 23.8 mmol), ethanol (12 mL) and toluene (24 mL). The solution was sparged with argon for 10 min and Pd(PPh$_3$)$_4$ (689 mg, 0.6 mmol) was added. The biphasic solution was vigorously stirred under inert atmosphere at 80° C. for 16 h, then was cooled to rt. EtOAc (80 mL) and water (20 mL) were added and the layers were separated. The organic layer was washed with saturated NaHCO$_3$ (2×20 mL), brine (20 mL) and was dried over sodium sulfate. Removal of the solvents in vacuo followed by column chromatography (85:15 DCM/EtOAc) of the residue yielded the title compound (2.24 g, 55%) as a light brown solid. $^1$H-NMR (CDCl$_3$): δ 7.98 (ddd, 1H, J=1.3, 1.9, 7.8 Hz), 7.89 (m, 2H), 7.61 (t, 1H, J=7.7 Hz), 7.5 (dt, 1H, J=1.3, 7.7 Hz), 6.88 (s, 1H), 6.55 (d, 1H, J=1.7 Hz), 6.47 (s, 1H), 4.26 (m, 2H), 3.42 (s, 2H), 2.56 (s, 3H), 1.9 (s, 3H), 1.52 (s, 9H), 1.06 (m, 2H), 0.08 (s, 9H).

g) 6-{3-[3'-[5-(tert-Butoxycarbonylamino-imino-methyl)-2-methylsulfanyl-thiophene-3-sulfonyl]-6-methyl-4-(2-trimethylsilanyl-ethoxycarbonylamino)-biphenyl-2-yl]-ureido}-hexanoic acid ethyl ester

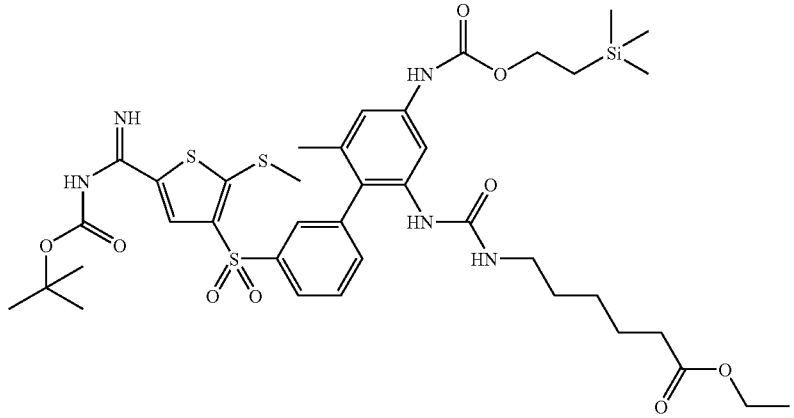

A solution of {2-amino-3'-[5-(imino-methoxycarbonylamino-methyl)-2-methylsulfanyl-thiophene-3-sulfonyl]-6-methyl-biphenyl-4-yl}-carbamic acid 2-trimethylsilanyl-ethyl ester ((Example 2: step f) 0.020 g, 0.030 mmol) in dry $CH_2Cl_2$ (3 mL) was treated with 6-isocyanato-hexanoic acid ethyl ester (5.30 μL, 0.030 mmol) and stirred at room temperature 40 min. The reaction mixture was diluted with $CH_2Cl_2$ and washed with water (1×15 mL). The organic layer was dried over $MgSO_4$ and concentrated in vacuo to afford the product 6-{3-[3'-[5-(tert-butoxycarbonylamino-imino-methyl)-2-methylsulfanyl-thiophene-3-sulfonyl]-6-methyl-4-(2-trimethylsilanyl-ethoxycarbonylamino)-biphenyl-2-yl]-ureido}-hexanoic acid ethyl ester (0.025 g, 98%) as an off-white solid. $^1$H NMR ($CD_3OD$): δ 8.22 (s, 1H), 8.06 (d, 1H, J=8.0 Hz), 7.92 (t, 1H, J=1.6 Hz), 7.72 (t, 1H, J=8.0 Hz), 7.65 (d, 1H, J=1.6 Hz), 7.56 (d, 1H, J=7.6 Hz), 7.28 (s, 1H), 4.29 (m, 2H), 3.06-3.00 (m, 2H), 2.70 (s, 3H), 2.33 (t, 2H, J=7.2 Hz), 2.01 (s, 3H), 1.60 (quint, 2H, J=7.2 Hz), 1.54 (s, 9H), 1.40-1.36 (m, 2H), 1.12 (m, 2H), 1.28 (t, 3H, J=7.2 Hz), 0.09 (s, 9H). ESI-MS (m/z): Calcd. for $C_{39}H_{55}N_5O_9S_3Si$ (M+H): 862.3; found 861.9.

h) 6-{3-[3-[5-(tert-Butoxycarbonylamino-imino-methyl)-2-methylsulfanyl-thiophene-3-sulfonyl]-6-methyl-4-(2-trimethylsilanyl-ethoxycarbonylamino)-biphenyl-2-yl]-ureido}-hexanoic acid

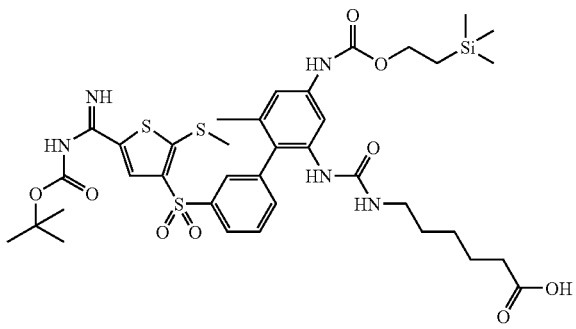

A solution of 6-{3-[3'-[5-(tert-butoxycarbonylamino-imino-methyl)-2-methylsulfanyl-thiophene-3-sulfonyl]-6-methyl-4-(2-trimethylsilanyl-ethoxycarbonylamino)-biphenyl-2-yl]-ureido}-hexanoic acid ethyl ester ((Example 2: step g) 0.437 g, 0.507 mmol) in THF:water (2:1, 15 mL) was treated with solid LiOH (0.097 g, 4.06 mmol) and stirred at room temperature 18.5 h. The THF was removed in vacuo, and the remaining aqueous solution was acidified to pH 5 with glacial acetic acid. The solution was extracted with $CH_2Cl_2$ (3×50 mL). The combined organic layers were dried over $MgSO_4$ and concentrated in vacuo to afford the product 6-{3-[3'-[5-(tert-butoxycarbonylamino-imino-methyl)-2-methylsulfanyl-thiophene-3-sulfonyl]-6-methyl-4-(2-trimethylsilanyl-ethoxycarbonylamino)-biphenyl-2-yl]-ureido}-hexanoic acid (0.4222 g, 99%) as an off-white solid. ESI-MS (m/z): Calcd. for $C_{37}H_{51}N_5O_9S_3Si$ (M+H): 834.3; found: 834.2.

i) 6-(3-{3'-[5-(tert-Butoxycarbonylamino-imino-methyl)-2-methylsulfanyl-thiophene-3-sulfonyl]-4-(N,N-bis-(tert-butoxycarbonylamino))guanidino-6-methyl-biphenyl-2-yl}-ureido)-hexanoic acid

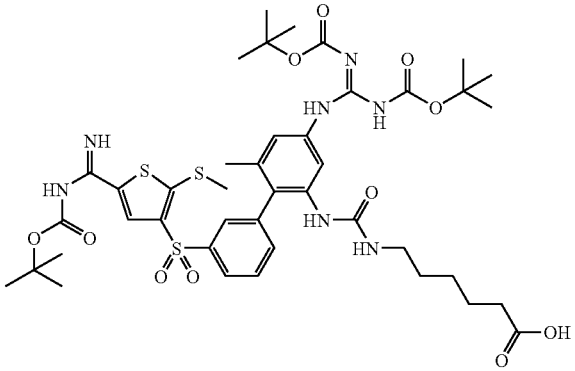

A solution of 6-{3-[3'-[5-(tert-butoxycarbonylamino-imino-methyl)-2-methylsulfanyl-thiophene-3-sulfonyl]-6-methyl-4-(2-trimethylsilanyl-ethoxycarbonylamino)-biphenyl-2-yl]-ureido}-hexanoic acid ((Example 2: step h) 0.422 g, 0.506 mmol) in dry THF (20 mL) was treated with tetrabutylammonium fluoride (1 M in THF, 3.39 mL, 3.39 mmol) and stirred at 40° C. 4 h. Solvents were evaporated in vacuo. The residue was taken up in $CH_2Cl_2$ and washed with water (4×50 mL). The organic layer was dried over $MgSO_4$ and concentrated in vacuo. Silica gel chromatography (4% MeOH in $CH_2Cl_2$) afforded the product 6-(3-{4-amino-3'-[5-(tert-butoxycarbonylamino-imino-methyl)-2-methylsulfanyl-thiophene-3-sulfonyl]-6-methyl-biphenyl-2-yl}-ureido)-hexanoic acid (0.200 g, 57%) as an off-white solid. The material was combined with 1,3-bis(tert-butoxycarbonyl)-2-methyl-2-thiopseudourea (0.252 g, 0.870 mmol) and acetic acid (0.5. mL) in MeOH (10 mL) and was stirred at 40° C. for 2 h. The solvent was removed in vacuo. Silica gel chromatography (4% MeOH in $CH_2Cl_2$ then 10% MeOH in $CH_2Cl_2$) afforded the title compound (0.215 g, 80%) as a white solid. $^1$H-NMR ($CD_3OD$): δ 8.22 (s, 1H), 8.06 (m, 1H), 7.89 (m, 1H), 7.72 (m, 1H), 7.69 (m, 1H), 7.53 (m, 1H), 7.32 (m, 1H), 3.01 (m, 2H), 2.66 (s, 3H), 2.27 (t, 2H, 7.4 Hz), 1.97 (s, 3H), 1.57 (m, 2H), 1.54 (s, 18H), 1.51 (s, 9H), 1.37 (m, 2H), 1.27 (m, 2H).

j) mPEG$_{20K}$ Amide of 6-{3-[3'-(5-Carbamimidoyl-2-methylsulfanyl-thiophene-3-sulfonyl)-4-guanidino-6-methyl-biphenyl-2-yl]-ureido}-hexanoic acid bis-trifluoroacetate

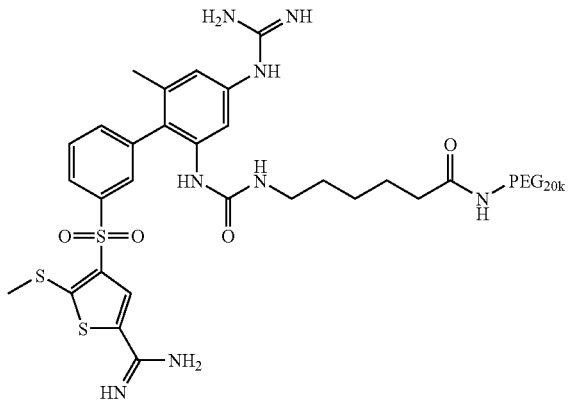

Diisopropylcarbodiimide (0.2M in DCM, 1.125 mL) was added dropwise to a solution of 6-(3-{3'-[5-(tert-Butoxycarbonylamino-imino-methyl)-2-methylsulfanyl-thiophene-3-sulfonyl]-4-(N,N'-bis-tert-butoxycarbonyl)-guanidino-6-methyl-biphenyl-2-yl}-ureido)-hexanoic acid (Example 2: step i (210 mg, 0.23 mmol)) and N,N-dimethylaminopyridine (32 mg, 0.26 mmol) in DCM (23 mL) at 0° C. The solution was stirred for 30 min at 0° C. and mPEG$_{20K}$-NH$_2$ (3.25 g, 0.15 mmol) was added. The solution was warmed to rt and was stirred for 6 h (ninhydrin negative on TLC) at rt. DCM (10 mL) was added followed by the slow addition of Et$_2$O to induce a slow precipitation. An additional small portion of ether was added to insure complete precipitation, and the solid was collected via filtration and washed with DCM/Et$_2$O to yield ~3.3 g of crude PEGylated compound. The solid mass was redissolved in 20% MeOH/DCM and Et$_2$O was added slowly to induce precipitation. The solid was collected via filtration and the solid cake was dried under high vacuum. Analysis of the "crude" material by HPLC showed purity ~98%, and was devoid of small-molecule starting material impurities (according to HPLC analysis of the filtrate). The dried PEGylated compound was redissolved in DCM (8 mL) and H$_2$O (0.1 mL) was added followed by TFA (8 mL). After stirring for 1.5 h MeOH was added (4 mL) followed by slow addition of Et$_2$O to induce gradual precipitation. A portion of the material was subjected to HPLC purification (C18 column, 10-55% CH$_3$CN in H$_2$O (0.1% TFA) over 30 min) giving 120 mg of PEGylated compound. The two batches of PEG (HPLC purified vs. precipitation only) were identical $^1$H-NMR analysis and analytical HPLC showed <0.5% difference in purity between the two. The purity of the precipitated PEGylated compound was determined to be >99.2% (HPLC, λ=214, 254), where no single impurity comprised more than 0.3% of the total area. $^1$H-NMR (CDCl$_3$/CD$_3$OD) (with PEG suppression at δ 3.62): δ 8.24 (s, 1H), 8.03 (ddd, 1H, J=1.2, 1.9, 7.9 Hz), 7.82 (t, 1H, J=1.2 Hz), 7.69 (t, 1H, J=7.7 Hz), 7.58 (d, 1H, J=1.9 Hz) 7.49 (dt, 1H, J=1.3, 7.9 Hz), 6.88 (d, 1H, J=1.9 Hz), 4.22 (s, DOH), 3.81 (m, PEG satellite), 3.62 (m, PEG methylenes), 3.45 (m, PEG satellite), 3.36 (s, 3H, PEG-OMe terminus), 3.03 (t, 1H, J=6.7 Hz) 2.67 (s, 3H), 2.15 (t, 2H, J=7.4 Hz), 1.97 (s, 3H), 1.55 (m, 2H), 1.37 (m, 2H), 1.22 (m, 2H).

Example 3 mPEG$_{20K}$ Amide of 11-[3'-(5-carbamimidoyl-2-methylsulfanyl-thiophene-3-sulfonyl)-6-methyl-biphenyl-2-ylcarbamoyl]-undecanoic acid trifluoroacetate

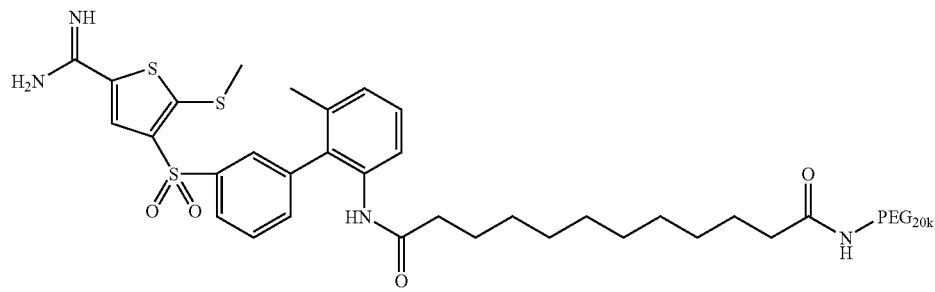

a) 11-{3'-[5-(tert-Butoxyarbonylamino-imino-methyl)-2-methylsulfanyl-thiophene-3-sulfonyl]-6-methyl-biphenyl-2-ylcarbamoyl}-undecanoic acid ethyl ester

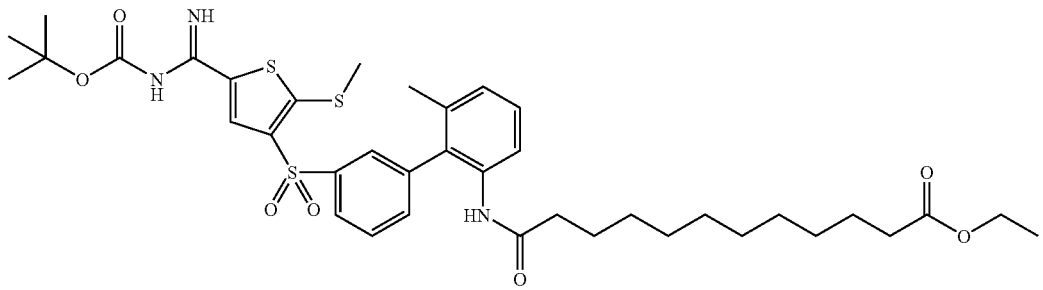

A solution of 11-chlorocarbonyl-undecanoic acid ethyl ester (0.08 g, 0.29 mmol) in dichloromethane (1 mL) was added dropwise to a solution {[4-(2'-amino-6'-methyl-biphenyl-3-sulfonyl)-5-methylsulfanyl-thiophen-2-yl]-imino-methyl}-carbamic acid tert-butyl ester (U.S. provisional application 60/383130 (0.10 g, 0.19 mmol)) and triethylamine (0.04 mL, 0.29 mmol) in dichloromethane (5 mL) at room temperature and stirred for 1 hour. The reaction mixture was then evaporated and the crude mixture was purified via column chromatography (hexane:ethyl acetate (2:1)) to give 0.060 g of 11-{3'-[5-(tert-butoxycarbonylamino-imino-methyl)-2-methylsulfanyl-thiophene-3-sulfonyl]-6-methyl-biphenyl-2-ylcarbamoyl}-undecanoic acid ethyl ester. $^1$H NMR (CDCl$_3$): δ: 7.99 (d, 1H, J=8.4 Hz), 7.95 (s, 1H), 7.86 (s, 1H), 7.67 (d, 1H, J=7.2 Hz), 7.61 (t, 1H, J=7.2 Hz), 7.44 (d, 1H, J=8.0 Hz), 7.33 (t, 1H, J=7.2 Hz), 7.16 (d, 1H, J=7.6 Hz), 6.69 (s, 1H), 6.60-6.40 (bs, 1H), 4.12 (q, 2H, J=6.4 Hz), 2.60 (s, 3H), 2.31 (t, 2H, J=7.6 Hz), 2.05-1.93 (m, 5H), 1.62 (m, 4H), 1.52 (s, 9H), 1.32-1.03 (m, 15H). Mass spectrum (LCMS, ESI) calculated for C$_{38}$H$_{51}$N$_3$O$_7$S$_3$ 757.29 (M+1); found 757.92.

b) 11-{3'-[5-(tert-Butoxycarbonylamino-imino-methyl)-2-methylsulfanyl-thiophene-3-sulfonyl]-6-methyl-biphenyl-2-ylcarbamoyl}-undecanoic acid nol (1 mL) at room temperature for several hours. The reaction mixture was then evaporated and 1N HCl was added dropwise until the pH was 1. The product was extracted with ethyl acetate, dried over sodium sulfate and evaporated in vacuo to give 0.05 g of 11-{3'-[5-(tert-butoxycarbonylamino-imino-methyl)-2-methylsulfanyl-thiophene-3-sulfonyl]-6-methyl-biphenyl-2-ylcarbamoyl}-undecanoic acid. $^1$H NMR (CDCl$_3$): δ 7.99 (d, 1H, J=8.4 Hz), 7.95 (s, 1H), 7.89 (s, 1H), 7.68 (d, 1H, J=8.4 Hz), 7.62 (t, 1H, J=7.6 Hz), 7.45 (d, 1H, J=8.0 Hz), 7.33 (t, 1H, J=6.8 Hz), 7.16 (d, 1H, J=6.8 Hz), 6.71 (s, 1H), 2.60 (s, 3H), 2.37 (t, 2H, J=6.8 Hz), 2.03 (s, 3H), 2.05-1.94 (m, 2H), 1.64 (m, 4H), 1.53 (s, 9H), 1.32-1.04 (m, 12H). Mass spectrum (LCMS, ESI) calculated for C$_{36}$H$_{47}$N$_3$O$_7$S$_3$ 729.26 (M+1); found 729.90.

c) mPEG20K Amide of 11-{3'-[5-(tert-Butoxycarbonylamino-imino-methyl)-2-methylsulfanyl-thiophene-3-sulfonyl]-6-methyl-biphenyl-2-ylcarbamoyl}-undecanoic acid

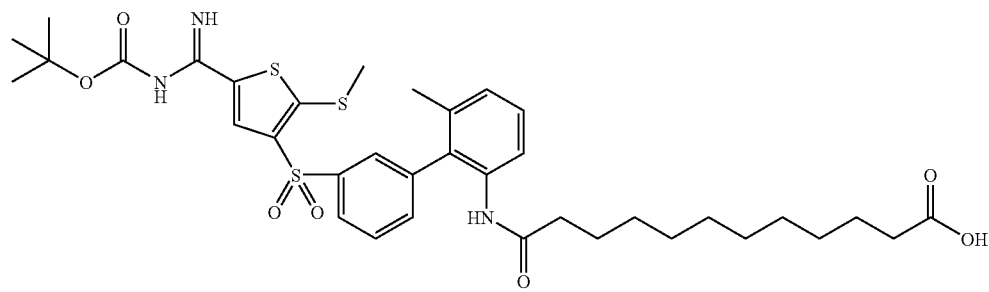

A 1 M solution of sodium hydroxide (0.24 mL) was added dropwise to a solution of 11-{3'-[5-(tert-butoxycarbonylamino-imino-methyl)-2-methylsulfanyl-thiophene-3-sulfonyl]-6-methyl-biphenyl-2-ylcarbamoyl}-undecanoic acid ethyl ester (Example 3: step a (0.06 g, 0.08 mmol)) in metha-

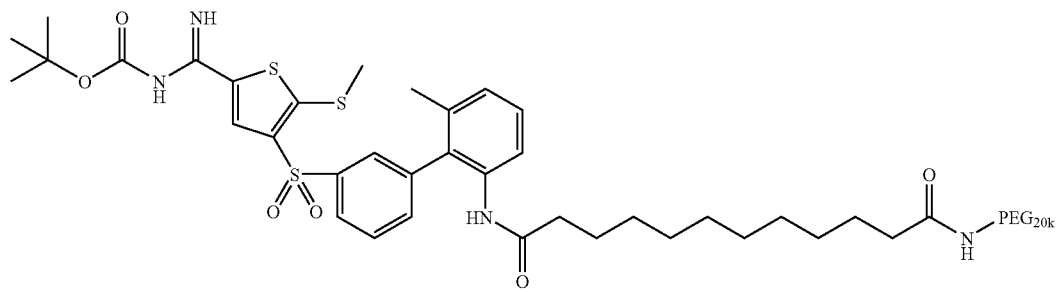

Diisopropylcarbodiimide (0.005 g, 0.0411 mmol) was added dropwise to a solution of 11-{3'-[5-(tert-butoxycarbonylamino-imino-methyl)-2-methylsulfanyl-thiophene-3-sulfonyl]-6-methyl-biphenyl-2-ylcarbamoyl}-undecanoic acid ((Example 3: step b) 0.030 g, 0.0411 mmol) and dimethylaminopyridine (0.008 g, 0.0616 mmol) in dichloromethane (4.0 mL) at room temperature and stirred for 10 minutes. mPEG$_{20K}$-NH$_2$ (0.412 g, 0.0206 mmol) was dissolved in a minimal amount of dichloromethane and was added dropwise to the reaction and allowed to stir overnight. The reaction mixture was then evaporated and the product was recrystallized twice from isopropanol, followed by reverse phase HPLC purification (acetonitrile/water (0.1% TFA) to give 0.370 g of PEGylated product. $^1$H NMR (CDCl$_3$): δ 8.13 (s, 1H), 7.97 (m, 2H), 7.71 (d, 1H, J=7.2 Hz), 7.62 (t, 1H, J=8.0 Hz), 7.46 (d, 1H, J=7.6 Hz), 7.31 (t, 1H, J=7.6 Hz), 7.13 (d, 1H, J=7.2 Hz), 6.98 (s, 1H), 6.25 (s, 1H), 2.59 (s, 3H), 2.30 (m, 2H), 2.02 (s, 3H), 2.07-1.97 (m, 2H), 1.64 (m, 4H), 1.53 (s, 9H), 1.36-1.06 (m, 12H).

d) mPEG$_{20K}$ Amide of 11-[3'-(5-carbamimidoyl-2-methylsulfanyl-thiophene-3-sulfonyl)-6-methyl-biphenyl-2-ylcarbamoyl]-undecanoic acid trifluoroacetate fonyl]-6-methyl-biphenyl-2-ylcarbamoyl}-undecanoic acid (Example 3: step c (0.370 g, 0.018 mmol)) in dichloromethane (3.0 mL) and stirred for 1 hour. The reaction was then evaporated and purified via reverse phase HPLC to give 0.200 g of PEGylated product as a trifluoroacetate salt. $^1$H NMR (with PEG suppression at δ 3.62) (CDCl$_3$): δ 10.1 (s, 2H), 8.65 (s, 1H), 8.20 (s, 1H), 7.93 (d, 1H, J=8.0 Hz), 7.89 (s, 1H), 7.55 (t, 1H, J=7.6 Hz), 7.47 (d, 1H, J=8.0 Hz), 7.42 (d, 1H, J=8.0 Hz), 7.25 (t, 1H, J=7.6 Hz), 7.10 (d, 1H, J=7.6 Hz), 6.36 (s, 1H), 2.58 (s, 3H), 2.12 (m, 2H), 1.99 (s, 3H), 1.98-1.92 (m, 2H), 1.55 (m, 4H), 1.26-0.95 (m, 12H).

Example 4 mPEG$_{20K}$ Amide of 4-(5-{3-[3'-(5-carbamimidoyl-2-methylsulfanyl-thiophene-3-sulfonyl)-4-guanidino-6-methyl-biphenyl-2-yl]-ureido}-pentyloxy)-benzoic acid bis-trifluoroacetate

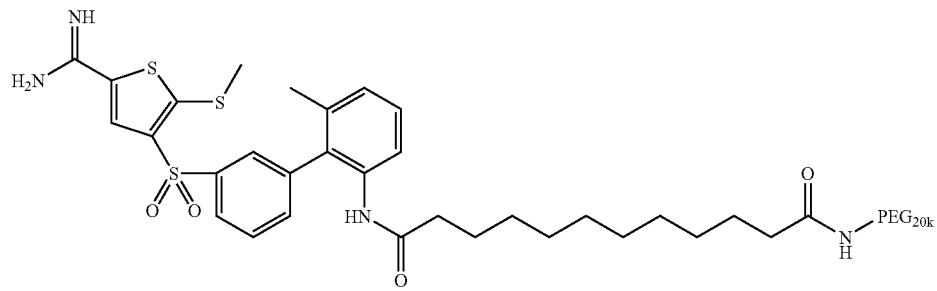

Trifluoroacetic acid (3.0 mL) was added dropwise to a solution of mPEG$_{20K}$ amide of 11-{3'-[5-(tert-butoxycarbonylamino-imino-methyl)-2-methylsulfanyl-thiophene-3-sul-

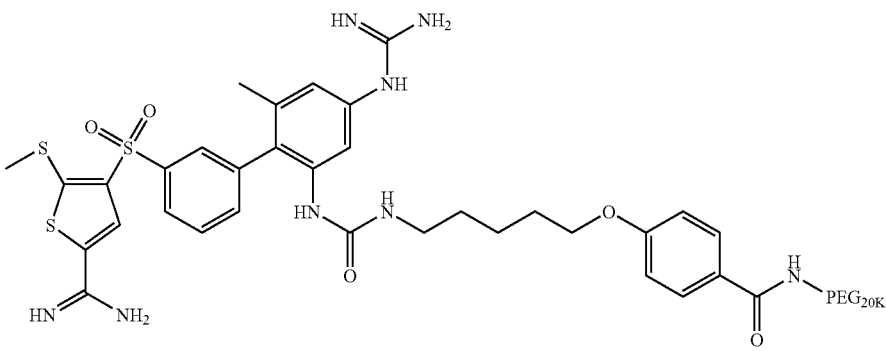

a) 4-[5-(1,3-Dioxo-1,3-dihydro-isoindol-2-yl)-pentyloxy]-benzoic acid methyl ester

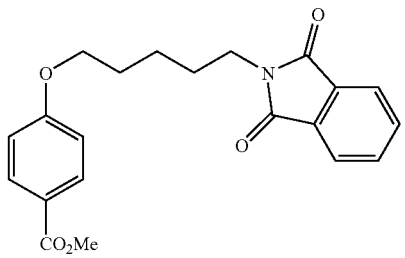

A mixture of 4-hydroxy-benzoic acid methyl ester (3.01 g, 19.8 mmol), 2-(5-bromo-pentyl)-isoindole-1,3-dione (3.9 g, 13.2 mmol), and K$_2$CO$_3$ (1.82 g, 13.2 mmol) in acetone (150 mL) was heated to reflux for 24 h. The reaction mixture was cooled to rt and the solvents were removed in vacuo. The crude was diluted in EtOAc and washed with 1N NaOH and brine. The organic layer was dried over sodium sulfate. The solvents were removed in vacuo. The crude was recrystallized from EtOAc to afford the title compound as a white solid (4 g, 83%). $^1$H-NMR (CDCl$_3$): δ 7.95-7.98 (m, 2H), 7.83-7.86 (m, 2H), 7.70-7.73 (m, 2H), 6.86-6.89 (m, 2H), 4.00 (t, 2H, J=6.22 Hz), 3.88 (s, 3H), 3.73 (t, 2H, J=7.29 Hz), 1.82-1.89 (m, 2H), 1.73-1.81 (m, 2H), 1.50-1.57 (m, 2H).

b) 4-(5-Amino-pentyloxy)-benzoic acid methyl ester

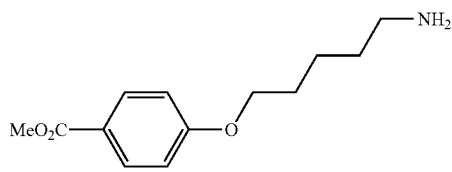

A suspension of 4-[5-(1,3-dioxo-1,3-dihydro-isoindol-2-yl)-pentyloxy]-benzoic acid methyl ester (1 g, 2.72 mmol, Example 4: step a) and hydrazine (98.4 µL, 3.13 mmol) in MeOH:H$_2$O (10 mL, 4:1) was heated to 65° C. for 2 h. Additional hydrazine was added (171 µL, 5.44 mmol) to the reaction mixture at rt. The reaction mixture was heated to 70° C. for 2 h then stirred overnight at rt. Potassium carbonate (30 mL, 1N aqueous) and methylene chloride (200 mL) were added to the reaction. The organic layer was dried over magnesium sulfate. The solvents were removed in vacuo to afford the title compound as a white solid (500 mg, 77%). $^1$H-NMR (CDCl$_3$): δ 7.95-8.00 (m, 2H), 6.88-6.92 (m, 2H), 4.02 (t, 2H, J=6.43 Hz), 3.88 (s, 3H), 2.71-2.76 (m, 2H), 1.79-1.86 (m, 2H), 1.49-1.56 (m, 4H).

c) 4-(5-{3-[3'-[5-(tert-Butoxycarbonylamino-imino-methyl)-2-methylsulfanyl-thiophene-3-sulfonyl]-6-methyl-4-(2-trimethylsilanyl-ethoxycarbonylamino)-biphenyl-2-yl]-ureido}-pentyloxy)-benzoic acid methyl ester

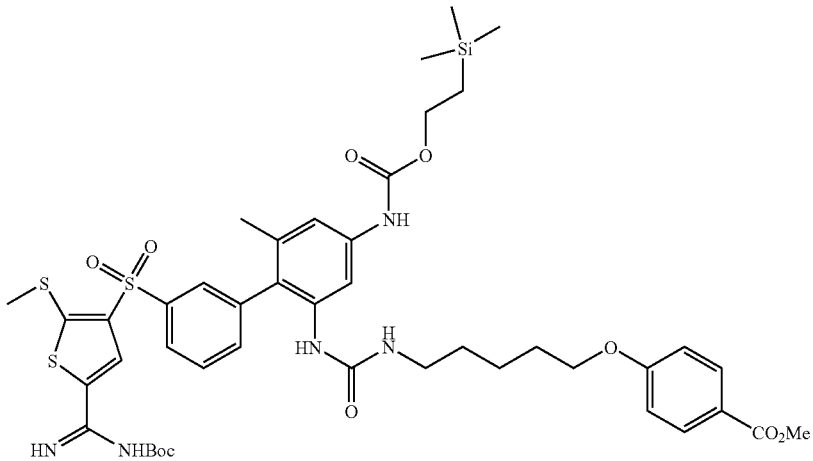

4-Nitrophenyl chloroformate (99.2 mg, 0.49 mmol) was added to a solution of {2-amino-3'-[5-(tert-butoxycarbonylamino-imino-methyl)-2-methylsulfanyl-thiophene-3-sulfonyl]-6-methyl-biphenyl-4-yl}-carbamic acid 2-trimethylsilanyl-ethyl ester (303 mg, 0.45 mmol, Example 2: step f) and pyridine (39.8 µL, 0.49 mmol) in methylene chloride (5 mL) at rt. The reaction mixture was stirred for 2 h at rt. 4-(5-amino-pentyloxy)-benzoic acid methyl ester (117 mg, 0.49 mmol, Example 4: step b) and triethylamine were added to the reaction mixture and stirred for 2 h at rt. The reaction mixture was diluted in EtOAc, washed with water and brine, and dried over magnesium sulfate. Removal of solvents in vacuo was followed by flash chromatography (50-60% EtOAc/hexanes) to afford the title compound as a yellow solid (280 mg, 66.5%). ESI-MS (m/z): Calcd. for C$_{44}$H$_{57}$N$_5$O$_{10}$S$_3$Si: 940.3 (M+1); found: 939.9.

d) 4-(5-{3-[3'-[5-(tert-Butoxycarbonylamino-imino-methyl)-2-methylsulfanyl-thiophene-3-sulfonyl]-6-methyl-4-(2-trimethylsilanyl-ethoxycarbonylamino)-biphenyl-2-yl]-ureido}-pentyloxy)-benzoic acid

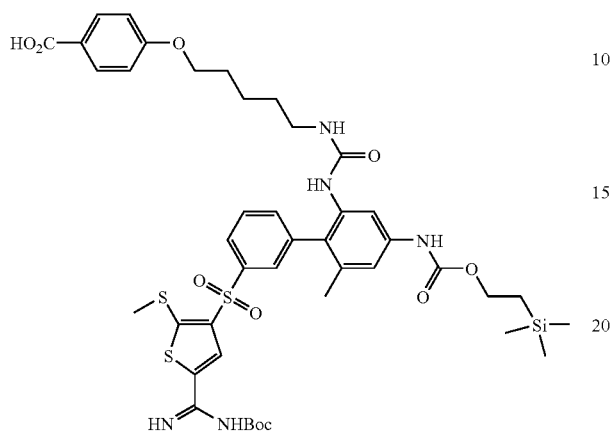

Lithium hydroxide (45.8 mg, 2.08 mmol) was added to a solution of 4-(5-{3-[3'-[5-(tert-butoxycarbonylamino-imino-methyl)-2-methylsulfanyl-thiophene-3-sulfonyl]-6-methyl-4-(2-trimethylsilanyl-ethoxycarbonylamino)-biphenyl-2-yl]-ureido}-pentyloxy)-benzoic acid methyl ester ((Example 4: step c) 280 mg, 0.298 mmol) in 1,4-dioxane/water (2:1, 10 mL) over 2 days at rt. The solvents were removed in vacuo. The residue was diluted in water, acidified to pH ~5 with acetic acid, and extracted with EtOAc. The organic layer was washed with brine and dried over magnesium sulfate. The solvents were removed in vacuo to afford the title compound as a yellow solid (276 mg, 100%). $^1$H-NMR (CDCl$_3$/CD$_3$OD): δ 7.93-7.99 (m, 3H), 7.83-7.86 (m, 2H), 7.52-7.59 (m, 2H), 7.15-7.20 (m, 2H), 6.85-6.89 (m, 2H), 4.21-4.26 (m, 2H), 3.99 (t, 2H, J=6.43 Hz), 3.13-3.24 (m, 2H), 2.61 (s, 3H), 2.02 (s, 3H), 1.75-1.83 (m, 2H), 1.43-1.56 (m, 13H), 1.02-1.08 (m, 2H), 0.07 (s, 9H).

e) 4-[5-(3-{4-Amino-3'-[5-(tert-butoxycarbonyl-amino-imino-methyl)-2-methylsulfanyl-thiophene-3-sulfonyl]-6-methyl-biphenyl-2-yl}-ureido)-pentyloxy]-benzoic acid

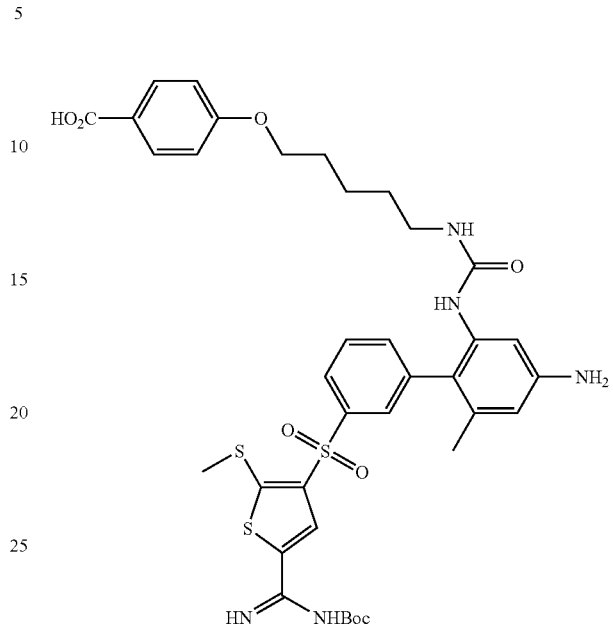

Tetrabutylammonium fluoride solution (2.38 mL, 1M in THF) was added to a solution of 4-(5-{3-[3'-[5-(tert-butoxycarbonylamino-imino-methyl)-2-methylsulfanyl-thiophene-3-sulfonyl]-6-methyl-4-(2-trimethylsilanyl-ethoxycarbonylamino)-biphenyl-2-yl]-ureido}-pentyloxy)-benzoic acid ((Example 4: step d) 276 mg, 0.298 mmol), in THF (10 mL) over 2 days at 35° C. The solvents were removed in vacuo. The residue was diluted in EtOAc, washed with water and brine, and dried over magnesium sulfate. The solvents were removed in vacuo to afford the title compound as a brown solid (300 mg, 100%). ESI-MS (m/z): Calcd. for C$_{37}$H$_{44}$N$_5$O$_8$S$_3$: 782.2 (M+1); found: 781.8.

f) 4-(5-{3-[3'-[5-(tert-Butoxycarbonylamino-imino-methyl)-2-methylsulfanyl-thiophene-3-sulfonyl]-4-(N',N''-bis(tertbutoxycarbonyl)-guanidino)-6-methyl-biphenyl-2-yl]-ureido}-pentyloxy)-benzoic acid

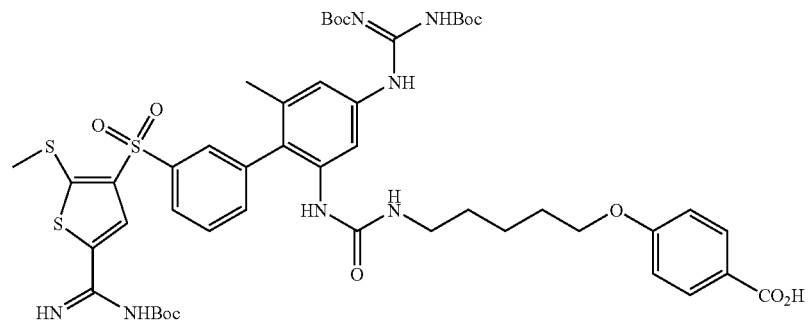

1,3-Bis(tert-butoxycarbonyl)-2-methyl-2-thiopseudourea (433 mg, 1.49 mmol) was added to a solution of 4-[5-(3-{4-amino-3'-[5-(tert-butoxycarbonylamino-imino-methyl)-2-methylsulfanyl-thiophene-3-sulfonyl]-6-methyl-biphenyl-2-yl}-ureido)-pentyloxy]-benzoic acid (233 mg, 0.298 mmol, Example 4: step e) in 5% AcOH/MeOH (10 mL) over 2 days at 35° C. The solvents were removed in vacuo and the residue was purified by flash chromatography (1-6% MeOH/methylene chloride) to afford the title compound as a yellow solid (70 mg, 23%). ESI-MS (m/z): Calcd. for $C_{48}H_{61}N_7O_{12}S_3$: 1024.4 (M+1); found: 1024.0.

g) mPEG$_{20K}$ Amide of 4-(5-{3-[3'-[5-(tert-butoxycarbonylamino-imino-methyl)-2-methylsulfanyl-thiophene-3-sulfonyl]-4-(N',N"-bis(tertbutoxycarbonyl)-guanidino)-6-methyl-biphenyl-2-yl]-ureido}-pentyloxy)-benzoic acid mPEG$_{20K}$-NH$_2$ (673 mg, 32 µmol) in DCM (2 mL, anhydrous. Analogous purification by precipitation with Et$_2$O afford the title compound as a white solid (650 mg, 92%). $^1$H-NMR with PEG suppression at δ 3.62 (CDCl$_3$): δ 8.03-7.97 (m, 2H), 7.84-7.76 (m, 3H), 7.64-7.54 (m, 1H), 7.46-7.39 (m, 1H), 7.33-7.31 (m, 1H), 7.10-7.02 (m, 2H), 6.87-6.83 (m, 2H), 4.02-3.96 (m, 2H), 3.25-3.19 (m, 2H), 2.63 (s, 3H), 2.03 (s, 3H), 1.82-1.75 (m, 2H), 1.56 (s, 9H), 1.52 (s, 9H), 1.49 (s, 9H), 1.48-1.45 (m, 4H).

h) mPEG$_{20K}$ Amide of 4-(5-{3-[3'-(5-carbamimidoyl-2-methylsulfanyl-thiophene-3-sulfonyl)-4-guanidino-6-methyl-biphenyl-2-yl]-ureido}-pentyloxy)-benzoic acid bis-trifluoroacetate

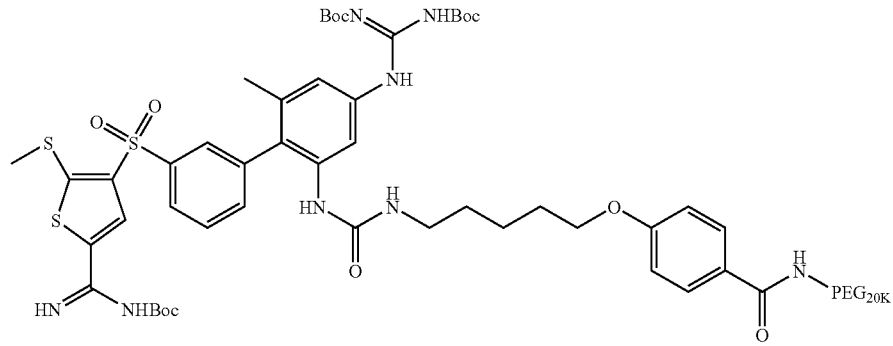

The coupling procedure in Example 2: step j was followed using 4-(5-{3-[3'-[5-(tert-butoxycarbonylamino-imino-methyl)-2-methylsulfanyl-thiophene-3-sulfonyl]-4-(N',N"-bis(tert-butoxycarbonyl)-guanidino)-6-methyl-biphenyl-2-yl]-ureido}-pentyloxy)-benzoic acid (Example 4: step f (42.7 mg, 41.7 µmol)), diisopropylcarbodiimide (5.26 mg, 41.7 µmol), 4-(dimethylamino)pyridine (9.8 mg, 41.7 µmol), and

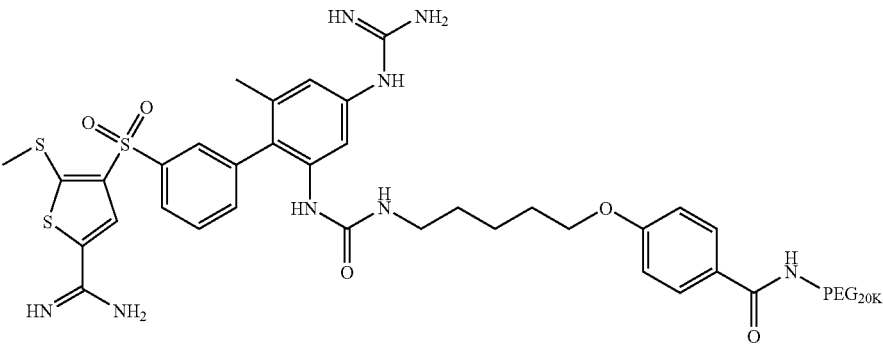

mPEG$_{20K}$ Amide of 4-(5-{3-[3'-[5-(tert-butoxycarbonylamino-imino-methyl)-2-methylsulfanyl-thiophene-3-sulfonyl]-4-(N',N''-bis(tertbutoxycarbonyl)-guanidino)-6-methyl-biphenyl-2-yl]-ureido}-pentyloxy)-benzoic acid (Example 4: step g (650 mg, 29.5 µmol)) was treated with TFA in DCM as in Example 2: step j. Analogous purification by precipitation with Et$_2$O and RP-HPLC afforded the title compound as a white solid (268 mg, 41.3%). $^1$H-NMR with PEG suppression at δ 3.59 (CDCl$_3$/CD$_3$OD): 8.29-8.26 (m, 1H), 8.05-8.00 (m, 1H), 7.85-7.82 (m, 1H), 7.78-7.74 (m, 2H), 7.71-7.65 (m, 1H), 7.59-7.55 (m, 1H), 7.52-7.47 (m, 1H), 6.92-6.87 (m, 3H), 4.03-3.97 (m, 2H), 3.13-3.07 (m, 2H), 2.67 (s, 3H), 1.97 (s, 3H), 1.82-1.75 (m, 2H), 1.51-1.42 (m, 4H).

Example 5 mPEG$_{20K}$ 2'-urea of 4-(2'-amino-4'-guanidino-6'-methyl-biphenyl-3-sulfonyl)-5-methylsulfanyl-thiophene-2-carboxamidine bis-trifluoroacetate

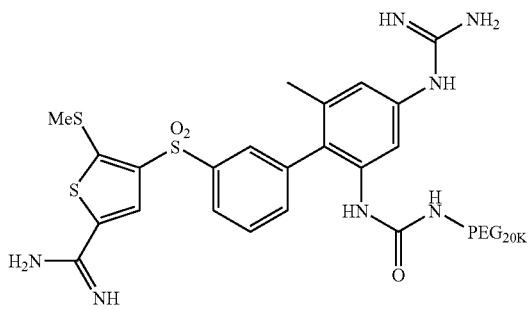

a) {[4-(2',4'-Diamino-6'-methyl-biphenyl-3-sulfonyl)-5-methylsulfanyl-thiophen-2-yl]-imino-methyl}-carbamic acid tert-butyl ester

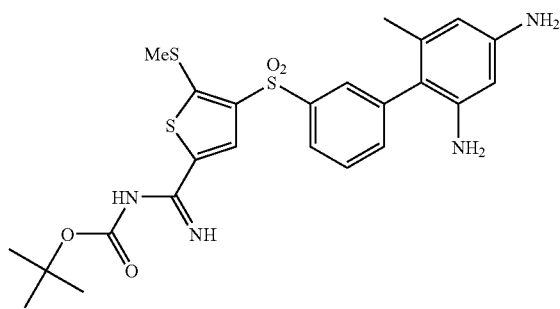

{2-Amino-3'-[5-(tert-butoxycarbonylamino-imino-methyl)-2-methylsulfanyl-thiophene-3-sulfonyl]-6-methyl-biphenyl-4-yl}-carbamic acid 2-trimethylsilanyl-ethyl ester (Example 2: step f (1 g, 1.48 mmol)) was dissolved into THF (25 mL). To this was added TBAF (1M, 1.62 mL, 1.62 mmol) and the reaction was warmed to 40° C. with stirring for 3 hours. Additional TBAF (1.48 mL, 1.48 mmol) was added and the reaction was stirred at rt overnight. The solvents were removed in vacuo, the residue was dissolved into EtOAc and washed with water several times (5 washes). The combined organic layers were dried (MgSO$_4$) and the solvents were removed in vacuo resulting in the title compound as a yellow solid (800 mg, 100%). $^1$H-NMR (CDCl$_3$): δ: 8.03 (s, 1H), 7.95-7.93 (m, 1H), 7.89-7.88 (m, 1H), 7.59-7.53 (m, 2H), 6.08 (m, 1H), 5.99 (m, 1H), 2.55 (s, 3H), 1.85 (s, 3H), 1.52 (s, 9H).

b) 4-{4'-[N',N''-bis(tert-butoxycarbonyl)]-}-{[4-(2'-amino-6'-methyl-biphenyl-3-sulfonyl)-5-methylsulfanyl-thiophen-2-yl]-imino-methyl}-carbamic acid tert-butyl ester

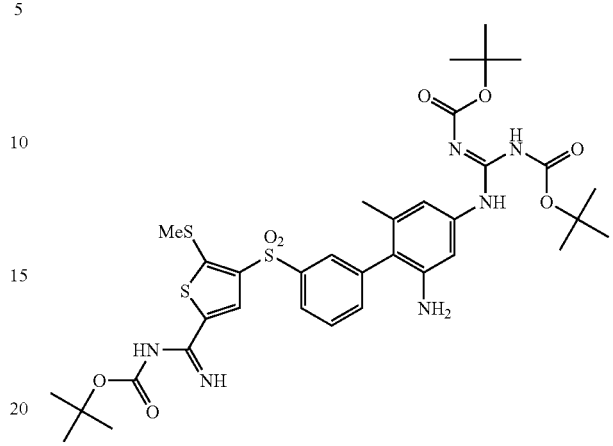

{[4-(2',4'-Diamino-6'-methyl-biphenyl-3-sulfonyl)-5-methylsulfanyl-thiophen-2yl]-imino-methyl}-carbamic acid tert-butyl ester ((Example 5: step a) 342 mg, 0.64 mmol) was dissolved into MeOH (4 mL) and acetic acid (200 µL). To this was added 1,3-bis(tert-butoxycarbonyl)-2-methyl-2-thiopseudourea (203 mg, 0.70 mmol) slowly as a suspension in MeOH and the reaction was stirred at rt overnight. The solvents were removed in vacuo followed by SiO$_2$ flash column chromatography purification (40% EtOAc in hexanes) that yielded the title compound (235 mg, 47%) as a white solid. ESI-MS (m/z): Calcd. for C$_{35}$H$_{46}$N$_6$O$_8$S$_3$: 775.3 (M+1); found: 774.8.

c) mPEG$_{20K}$ 2'-urea of 4-{4'-[N',N''-bis(tert-butoxycarbonyl)]-}-{[4-(2'-amino-6'-methyl-biphenyl-3-sulfonyl)-5-methylsulfanyl-thiophen-2-yl]-imino-methyl}-carbamic acid tert-butyl ester

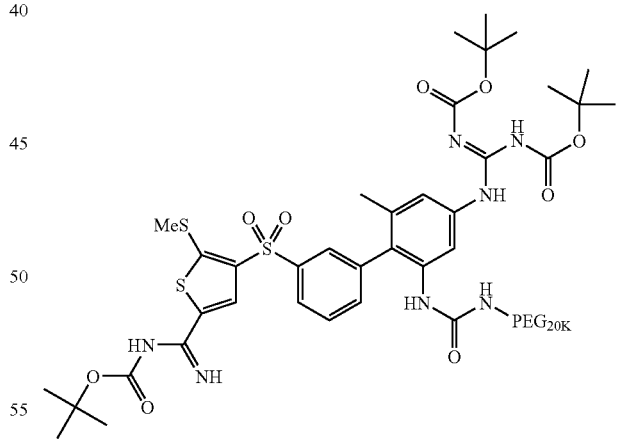

4-{4'-[N',N''-bis(tert-butoxycarbonyl)]-}-{[4-(2'-amino-6'-methyl-biphenyl-3-sulfonyl)-5-methylsulfanyl-thiophen-2-yl]-imino-methyl}-carbamic acid tert-butyl ester (Example 5: step b (67 mg, 0.09 mmol)) and pyridine (7.2 µL, 0.09 mmol) were dissolved into DCM (1.5 mL). The reaction was cooled to 0° C. followed by the addition of diisopropylethylamine (16 µL, 0.18 mmol) and p-nitrophenylchloroformate (15.7 mg, 0.08 mmol) and the reaction was stirred at 0° C. for 30 minutes. To this was added mPEG$_{20K}$-NH$_2$ (250 mg, 0.0125 mmol). The reaction was stirred at rt for 2 hours. To this was added diisopropylethylamine (32 µL, 0.36 mmol)

and DMAP (catalytic amount) and the reaction was stirred at rt overnight. The solvents were removed in vacuo and the residue was dissolved into DCM/MeOH. Ether (4× volume) was added slowly to the DCM/MeOH solution to precipitate the PEGylated compound. $^1$H-NMR (with PEG suppression at δ 3.61) (CDCl$_3$/CD$_3$OD): δ: 8.11 (s, 1H), 8.02-8.01 (m, 1H), 7.85(s, 1H), 7.68-7.62 (m, 2H), 7.45 (s, 1H), 2.63 (s, 3H), 1.96 (s, 1H), 1.55, (s, 9H), 1.49 (s, 9H), 1.43 (s, 9H).

d) mPEG$_{20K}$ 2'-urea of 4-(2'-amino-4'-guanidino-6'-methyl-biphenyl-3-sulfonyl)-5-methylsulfanyl-thiophene-2-carboxamidine bis-trifluoroacetate

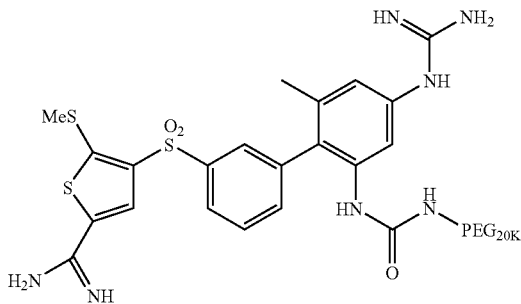

mPEG$_{20K}$ 2'-urea of 4-{4'-[N',N"-bis(tert-butoxycarbonyl)]-}-{[4-(2'-amino-6'-methyl-biphenyl-3-sulfonyl)-5-methylsulfanyl-thiophen-2-yl]-imino-methyl}-carbamic acid tert-butyl ester (Example 5: step c) was dissolved into DCM (5 mL) and TFA (5 mL) and the reaction was stirred at rt for 1 hour. The solvents were removed in vacuo then the residue was dissolved into DCM/MeOH and ether was added to precipitate the product that was collected by filtration. Purification by RP-HPLC (10-100% CH$_3$CN/H$_2$O, X=245 nm, 40 minutes) yielded the title compound as a white solid (190 mg, overall yield for step c and d 76%). $^1$H-NMR (with PEG suppression at δ 3.60) (CDCl$_3$/CD$_3$OD): δ: 8.27 (s, 1H), 8.06-8.03 (m, 1H), 7.85(s, 1H), 7.71 (t, 1H, J=7.91 Hz, J=7.67 Hz), 7.58 (s, 1H), 7.53-7.50 (m, 2H), 2.69 (s, 3H), 1.98 (s, 1H).

Example 6

Route a mPEG$_{20K}$ Amide of 3-{[3'-(5-Carbamimidoyl-2-methylsulfanyl-thiophene-3-sulfonyl)-4-guanidino-6-methyl-biphenyl-2-ylcarbamoyl]-methylsulfanyl}-propionic acid bis-trifluoracetate

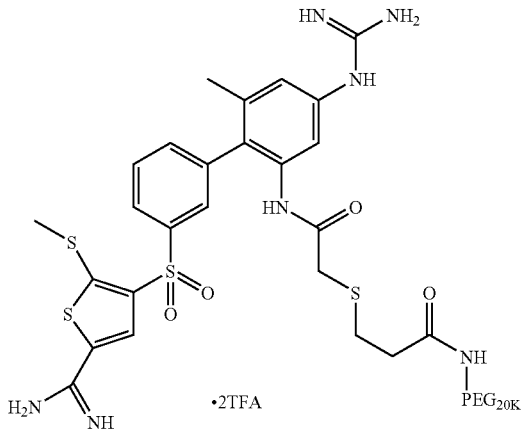

a) 3-tert-Butoxycarbonylmethylsulfanyl-propionic acid methyl ester

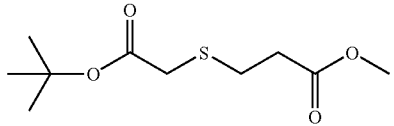

3-Mercapto-propionic acid methyl ester (3.4 mL, 30.7 mmol) was added to a solution of bromo-acetic acid tert-butyl ester (1.5 mL, 10.2 mmol) and Et$_3$N (3.4 mL, 30.7 mmol) in THF. The reaction was stirred for 3 h at rt then concentrated and the residue was partitioned between EtOAc and 1 N NaOH. The organic layer was washed 2× with 1N NaOH to remove all excess free thiol (monitored with Ellman's reagent). The organic layer was dried (MgSO$_4$) and concentrated to give the desired product as a clear oil (2.1 g, 88%). $^1$H NMR (CDCl$_3$) δ 3.45 (s, 3H), 2.91 (s, 2H), 2.66 (t, 2H, J=7.2 Hz), 2.42 (t, 2H, J=7.2 Hz), 1.23 (s, 9H).

b) 3-Carboxymethylsulfanyl-propionic acid methyl ester

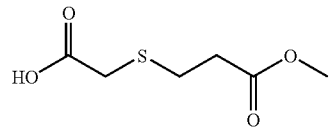

3-tert-Butoxycarbonylmethylsulfanyl-propionic acid methyl ester (2.1 g, as prepared in Example 6, Route a, step a) was treated with 50% TFA in DCM for 4 h. The mixture was concentrated in vacuo to provide the product as a solid that was used without further purification. $^1$H NMR (CDCl$_3$) δ 3.73 (s, 3H), 3.31 (s, 2H), 2.95 (t, 2H, J=7.2 Hz), 2.74 (t, 2H, J=7.2 Hz).

c) 3-{[3'-[5-(tert-Butoxycarbonylamino-imino-methyl)-2-methylsulfanyl-thiophene-3-sulfonyl]-6-methyl-4-(2-trimethylsilanyl-ethoxycarbonylamino)-biphenyl-2-ylcarbamoyl]-methylsulfanyl}-propionic acid

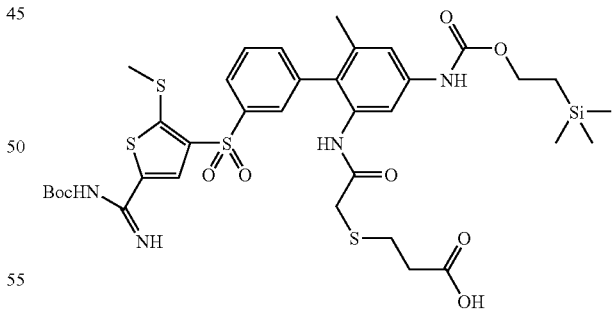

A solution of 3-Carboxymethylsulfanyl-propionic acid methyl ester (192 mg, 1.1 mmol, as prepared in Example 6, step b) in CH$_2$Cl$_2$ (10 mL) was treated with N,N-dimethylaminopyridine (232 mg, 1.9 mmol) and diisopropylcarbodiimide (172 μL, 1.1 mmol) stirred at room temperature 10 min. To the reaction mixture {6-amino-3'-[5-(tert-butoxycarbonylamino-imino-methyl)-2-methylsulfanyl-thiophene-3-sulfonyl]-2-methyl-biphenyl-4-yl}-carbamic acid 2-trimethylsilanyl-ethyl ester (248 mg, 0.37 mmol, as prepared in Example 2, step f) was added and the resulting mixture was stirred at rt for 6 h. The reaction mixture was diluted with DCM and then extracted with saturated NaHCO₃. The organic layer was washed with brine, dried (MgSO4), and concentrated to provide 250 mg of an oil as the crude 3-{[3'-[5-(tert-butoxycarbonylamino-imino-methyl)-2-methylsulfanyl-thiophene-3-sulfonyl]-6-methyl-4-(2-trimethylsilanyl-ethoxycarbonylamino)-biphenyl-2-ylcarbamoyl]-methylsulfanyl}-propionic acid methyl ester. ESI-MS (m/z): Calcd. for $C_{36}H_{48}N_4O_9S_4Si$: 837.21 (M+H); found: 836.9, 737.1. LC-MS showed this crude material to be ~90 pure and was used without further purification. Thus, this oil was dissolved in MeOH (10 mL) and a 1 N NaOH (10 mL) was added slowly with vigorous stirring. The mixture became cloudy and was warmed up to 50° C. After ~4 h, the reaction was complete by TLC. The reaction was acidified with AcOH and then concentrated in vacuo. The residue was partitioned between DCM and H₂O and the organic layer was washed with brine, dried (MgSO₄), and concentrated once more. The residue was chromatographed on SiO₂ (flash chromatography, elution: 100% DCM to 10% MeOH in DCM) to provide 160 mg of the title compound as tan semisolid. ESI-MS (m/z): Calcd. for $C_{35}H_{46}N_4O_9S_4Si$: 823.2 (M+H); found: 822.9, 723.2.

d) 3-({4-Amino-3'-[5-(tert-butoxycarbonylamino-imino-methyl)-2-methylsulfanyl-thiophene-3-sulfonyl]-6-methyl-biphenyl-2-ylcarbamoyl}-methylsulfanyl)-propionic acid

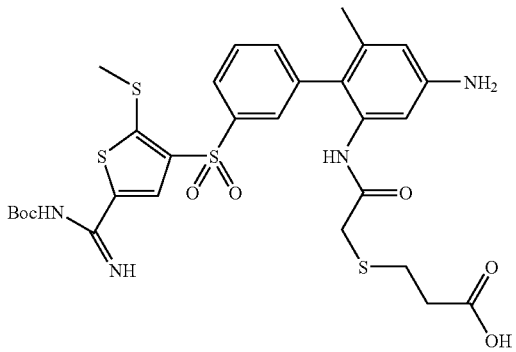

A solution of 3-{[3'-[5-(tert-butoxycarbonylamino-imino-methyl)-2-methylsulfanyl-thiophene-3-sulfonyl]-6-methyl-4-(2-trimethylsilanyl-ethoxycarbonylamino)-biphenyl-2-ylcarbamoyl]-methylsulfanyl}-propionic acid (0.650 g, 0.790 mmol, as prepared in Example 6, Route a, step c) in THF (60 mL) was treated with tetrabutyl ammonium fluoride (1 M in THF, 3.20 mL, 3.16 mmol) and warmed to 40° C. for 4.5 h. The solvents were removed in vacuo and the residue was taken up in EtOAc and washed with water (4×75 mL). The combined organic layers were dried over MgSO₄ and concentrated in vacuo to afford the product 3-({4-amino-3'-[5-(tert-butoxycarbonylamino-imino-methyl)-2-methylsulfanyl-thiophene-3-sulfonyl]-6-methyl-biphenyl-2-ylcarbamoyl}-methylsulfanyl)-propionic acid (0.340 g, 63%) as a white glassy solid. ESI-MS (m/z): Calcd. for $C_{29}H_{34}N_4O_7S_4$: 679.13 (M+1) found 678.80.

e) 3-({3'-[5-(tert-Butoxycarbonylamino-imino-methyl)-2-methylsulfanyl-thiophene-3-sulfonyl]-4-(N,N'-bis-tert-butoxycarbonyl)-guanidino-6-methyl-biphenyl-2-ylcarbamoyl}-methylsulfanyl)-propionic acid

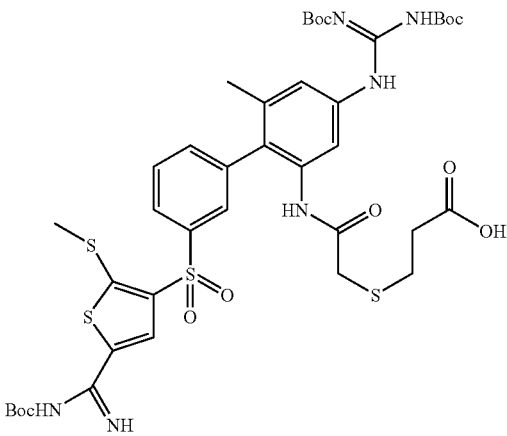

A solution of 3-({4-amino-3'-[5-(tert-butoxycarbonylamino-imino-methyl)-2-methylsulfanyl-thiophene-3-sulfonyl]-6-methyl-biphenyl-2-ylcarbamoyl}-methylsulfanyl)-propionic acid (0.340 g, 0.501 mmol, as prepared in Example 6, Route a, step d) in MeOH with 5% AcOH (15 mL) was treated with 1,3-bis(tert-butoxycarbonyl)-2-methyl-2-thiopseudourea and warmed to 40° C. for 4 h. Solvents were removed in vacuo. Silica gel chromatography (2-4% MeOH in CH₂Cl₂ raised in 0.5% increments) afforded the title compound (0.194 g, 42%) as a white glassy solid. ¹H NMR (CDCl₃): 8.385 (s, 1H), 8.031 (d, 1H, J=7.6 Hz), 8.008 (s, 1H), 7.887 (s, 1H), 7.624 (t, 1H, J=8.0 Hz), 7.430 (d, 1H, J=7.2 Hz), 7.340 (s, 1H), 3.008 (dd, 2H, J=50 Hz, J=17.2 Hz), 2.599 (s, 3H), 2.538 (d, 1H, J=8.4 Hz), 2.483 (s, 1H), 2.548 (s, 2H), 2.006 (s, 3H), 1.549 (s, 9H), 1.514 (s, 9H), 1.492 (s, 9H).

f) mPEG$_{20K}$ Amide of 3-({3'-[5-(tert-Butoxycarbonylamino-imino-methyl)-2-methylsulfanyl-thiophene-3-sulfonyl]-4-(N'-bis-tert-butoxycarbonyl)-guanidino-6-methyl-biphenyl-2-ylcarbamoyl}-methylsulfanyl)-propionic acid

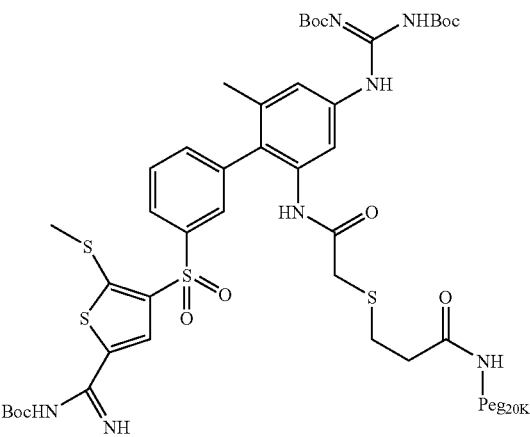

A solution of 3-({3'-[5-(tert-butoxycarbonylamino-imino-methyl)-2-methylsulfanyl-thiophene-3-sulfonyl]-4-(N,N'-bis-tert-butoxycarbonyl)-guanidino-6-methyl-biphenyl-2-ylcarbamoyl}-methylsulfanyl)-propionic acid (0.120 g, 0.130 mmol, as prepared in Example 6, Route a, step e) in CH$_2$Cl$_2$ (5 mL) was treated with N,N-dimethylaminopyridine (30.6 mg, 0.251 mmol) and diisopropylcarbodiimide (DIC, 20.4 μL, 0.130 mmol) stirred at room temperature 10 min. mPEG20K-NH$_2$ (2.104 g, 0.100 mmol, Rapp Polymere GMBH, Tübingen, Germany) was added as a solid and the mixture stirred at room temperature 18 h. The sample was checked for absence of any remaining mPEG$_{20K}$-NH$_2$ with ninhydrin stain. The solvents were removed in vacuo. The residue was transferred to a large Erlenmeyer flask with a minimal amount of 10% MeOH in CH$_2$Cl$_2$ (10 mL), and anhydrous diethyl ether was added slowly until the solution became cloudy and the product began to precipitate. The suspension was stirred for 20 min and then cooled to 4° C. for 30 min to ensure complete precipitation. The solids were filtered and dried in a vacuum dessicator. The title compound (2.08 g, 98%) was obtained as a white solid. $^1$H NMR (CDCl$_3$, 1 drop CD$_3$OD): δ 8.203 (s, 1H), 8.040 (d, 1H, J=7.6 Hz), 8.030 (s, 1H), 7.816 (t, 1H, J=1.6 Hz), 7.660 (t, 1H, J=7.6 Hz), 7.540 (d, 1H, J=1.6 Hz), 7.458 (d, 1H, J=8.0 Hz), 3.080 (dd, 2H, J=28 Hz, J=11 Hz), 2.617 (s, 3H), 2.287 (m, 4H), 1.996 (s, 3H), 1.548 (s, 9H), 1.518 (s, 9H), 1.502 (s, 9H).

g) mPEG$_{20K}$ Amide of 3-{[3'-(5-Carbamimidoyl-2-methylsulfanyl-thiophene-3-sulfonyl)-4-guanidino-6-methyl-biphenyl-2-ylcarbamoyl]-methylsulfanyl}-propionic acid bis-trifluoroacetate

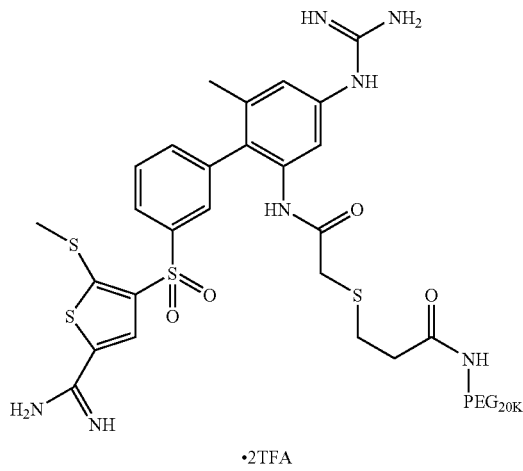

•2TFA

A solution of mPEG$_{20K}$ amide of 3-({3'-[5-(tert-Butoxycarbonylamino-imino-methyl)-2-methylsulfanyl-thiophene-3-sulfonyl]-4-(N,N'-bis-tert-butoxycarbonyl)-guanidino-6-methyl-biphenyl-2-ylcarbamoyl}-methylsulfanyl)-propionic acid (2.06 g, 0.001 mmol, as prepared in Example 6, Route a, step f) in CH$_2$Cl$_2$ (20 mL) was cooled to 0° C. and treated with trifluoroacetic acid (10.00 mL). The solution was allowed to warm to room temperature and was stirred for 4.5 h. The solvents were evaporated in vacuo. The residue was transferred to a large Erlenmeyer flask with a minimum amount of 10% MeOH in CH$_2$Cl$_2$ (13 mL). Diethyl ether was added until the solution turned cloudy and a precipitate began to form (~110 mL of Et$_2$O). The mixture was stirred at room temperature for 10 min then cooled to 4° C. for 30 min to ensure complete precipitation. The solids were filtered and dried in a vacuum dessicator. Preparatory HPLC (20-60% acetonitrile in 1% TFA/water over 40 min) afforded the product (1.60 g, 77%) as a white solid. $^1$H NMR (CDCl$_3$, 1 drop CD$_3$OD): δ 8.241 (s, 1H), 8.102 (d, 1H, J=8.8 Hz), 7.836 (t, 1H, J=1.6 Hz), 7.684 (t, 1H, J=8.0 Hz), 7.566 (s, 1H), 7.502 (d, 1H, J=8.0 Hz), 7.090 (s, 1H), 3.078 (dd, 2H, J=28, 11 Hz), 2.687 (s, 3H), 2.244 (m, 4H), 2.048 (s, 3H).

Route b mPEG$_{20K}$ Amide of 3-{[3'-(5-Carbamimidoyl-2-methylsulfanyl-thiophene-3-sulfonyl)-4-guanidino-6-methyl-biphenyl-2-ylcarbamoyl]-methylsufanyl}-propionic acid bis-trifluoroacetate

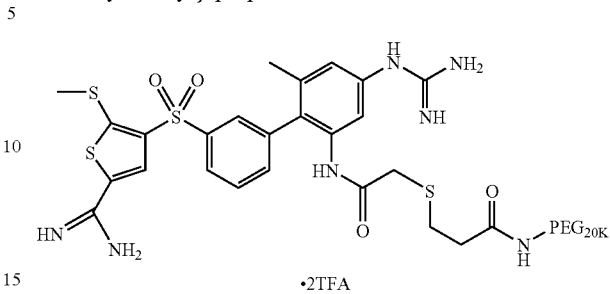

•2TFA a) ({4-[6'-(2-Hydroxy-acetylamino)-2'-methyl-4'-nitro-biphenyl-3-sulfonyl]-5-methylsulfanyl-thiophen-2-yl}-imino-methyl)-carbamic acid tert-butyl ester

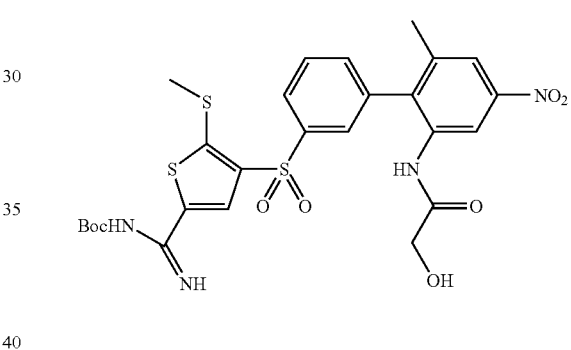

To a solution of {[4-(6'-amino-2'-methyl-4'-nitro-biphenyl-3-sulfonyl)-5-methylsulfanyl-thiophen-2-yl]-imino-methyl}-carbamic acid tert-butyl ester (216 mg, 0.384 mmol, as prepared in Example 1, step h) in DCM (2 mL) was added DIEA (212 μL, 1.15 mmol) and acetoxyacetyl chloride (54 mL, 0.5 mmol). The solution was stirred at rt for 3 hr. The reaction mixture was diluted with EtOAc and washed with saturated NaHCO$_3$, water, and brine. The organic layer was dried over MgSO$_4$, filtered, and concentrated in vacuo to provide 256 mg of a crude oil that was used without further purification. ESI-MS (m/z): Calcd. for C$_{28}$H$_{30}$N$_4$O$_9$S$_3$: 663.1 (M+H); found: 662.7, 563.0 (M-Boc). To a solution of the crude intermediate obtained above in MeOH (2.5 mL) was added 1 N NaOH (2.5 mL) and the mixture was stirred at rt for 45 min at which time TLC was consistent with complete hydrolysis of the acetyl group. The reaction mixture was neutralized with acetic acid, concentrated in vacuo, and the residue partitioned between EtOAc and saturated NaHCO$_3$. The organic layer was washed with water and brine, dried over MgSO$_4$, filtered, and concentrated in vacuo to give 220 mg (92%, crude yield over two steps) of the title compound which was used without further purification. ESI-MS (m/z): Calcd. for C$_{26}$H$_{28}$N$_4$O$_8$S$_3$: 621.1 (M+H); found: 620:7, 521.0 (M-Boc).

b) ({4-[4'-(N,N'-Bis-tert-butoxycarbonyl)-guanidino-6'-(2-hydroxy-acetylamino)-2'-methyl-biphenyl-3-sulfonyl]-5-methylsulfanyl-thiophen-2-yl}-imino-methyl)-carbamic acid tert-butyl ester

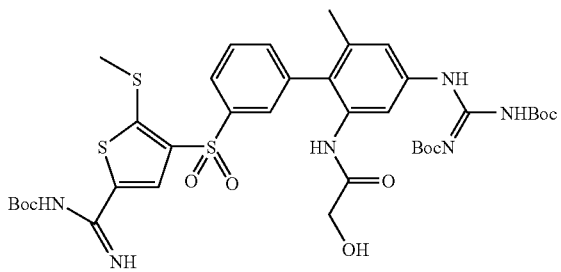

To a solution of ({4-[6'-(2-hydroxy-acetylamino)-2'-methyl-4'-nitro-biphenyl-3-sulfonyl]-5-methylsulfanyl-thiophen-2-yl}-imino-methyl)-carbamic acid tert-butyl ester (220 mg, 0.354 mmol, as prepared in Example 6, Route b, step a) in EtOH (2.2 mL) was added a solution of $NH_4Cl$ (1.1 mL, 3.2 M, 3.54 mmol). The mixture was stirred vigorously at 50° C. for 30 min. Iron powder (100 mg, 1.77 mmol) was added and the mixture was heated to 80° C. for 3.5 h. The reaction mixture was filtered (0.2 μ, Wheaton syringe filter) and the filtrate was concentrated to a solid that was partitioned between EtOAc and 1 N $Na_2CO_3$. The organic layer was washed with another portion of $Na_2CO_3$, dried ($MgSO_4$), filtered, and concentrated to give the crude desired product. Purification using PTLC (4×1500 μ plate, 5% MeOH in DCM) provided 58 mg of the desired aniline. ESI-MS (m/z): Calcd. for $C_{26}H_{30}N_4O_6S_3$: 591.1 (M+H); found: 591.0, 491.0 (M-Boc). To a solution of this aniline (55 mg, 0.09 mmol) in MeOH/AcOH (10:1, 5 mL), N,N'-bis(tert-butoxycarbonyl)-S-methylisothiourea (78 mg, 0.27 mmol, Aldrich Chemical Company) was added. The reaction mixture was warmed to 40° C. and stirred for 3 h. The mixture was concentrated in vacuo to a solid that was purified on PTLC (2×1000 μ plate, 1:1 EtOAc/hexanes) to give 45 mg (60%) of the title compound as a clear oil. $^1$H-NMR ($CDCl_3$; 400 MHz): δ 11.60 (s, 1H), 10.27 (s, 1H), 8.20 (m, 2H), 8.04 (d, 1H, J=6.7 Hz), 7.90 (br s, 1H), 7.64 (t, 1H, J=7.8 Hz), 7.40-7.45 (m, 2H), 4.42 (br s, 1H), 3.84 and 3.99 (AB quartet, 2H, J=15.4 Hz), 2.55 (s, 3H), 1.93 (s, 3H), 1.57 (s, 9H), 1.53 (s, 9H), 1.48 (s, 9H). ESI-MS (m/z): Calcd. for $C_{37}H_{48}N_6O_{10}S_3$: 833.2 (M+H); found: 832.8, 732.8, 632.9, 533.1.

c) Methanesulfonic acid {3'-[5-(tert-butoxycarbonylamino-imino-methyl)-2-methylsulfanyl-thiophene-3-sulfonyl]-4-(N,N'-bis-tert-butoxycarbonyl)-guanidino-6-methyl-biphenyl-2-ylcarbamoyl}-methyl ester

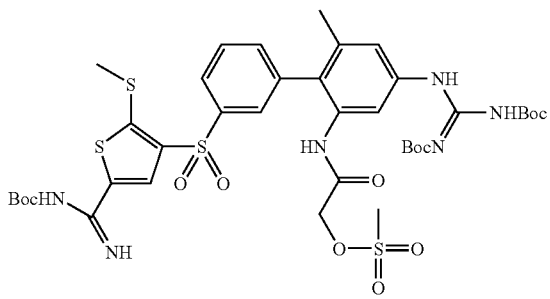

To a solution of ({4-[4'-(N,N'-bis-tert-butoxycarbonyl)-guanidino-6'-(2-hydroxy-acetylamino)-2'-methyl-biphenyl-3-sulfonyl]-5-methylsulfanyl-thiophen-2-yl}-imino-methyl)-carbamic acid tert-butyl ester (40 mg, 48 μmmol, as prepared in Example 6, Route b, step b) and diisopropyl ethylamine (100 μL, 192 μmol) in DCM (1 mL) at 0° C. was added methanesulfonyl chloride (10 μL, 130 μmol). The solution was stirred at 0° C. for 30 min and then allowed to warm up and stirred at rt for 5 h. The reaction mixture was concentrated in vacuo and the residue was chromatographed (PTLC, 1:1 EtOAc/hexanes, 1000 μ $SiO_2$ plate) to afford 40 mg (97%) of the desired title compound as a glassy solid. ESI-MS (m/z): Calcd. for $C_{38}H_{50}N_6O_{12}S_4$: 911.2 (M+H); found: 910.7, 810.8, 710.8, 611.1.

d) mPEG$_{20K}$ Amide of 3-{[3'-(5-Carbamimidoyl-2-methylsulfanyl-thiophene-3-sulfonyl)-4-guanidino-6-methyl-biphenyl-2-ylcarbamoyl]-methylsulfanyl}-propionic acid bis-trifluoroacetate

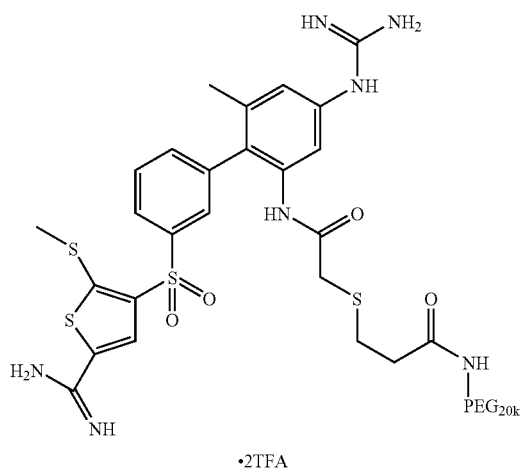

To a solution of methanesulfonic acid {3'-[5-(tert-butoxycarbonylamino-imino-methyl)-2-methylsulfanyl-thiophene-3-sulfonyl]-4-(N,N'-bis-tert-butoxycarbonyl)-guanidino-6-methyl-biphenyl-2-ylcarbamoyl}-methyl ester (21 mg, 0.023 mmol, as prepared in Example 6, Route b, step c) and diisopropyl ethylamine (100 μL, 192 μmol) in DCM (1.5 mL) was added mPEG$_{20K}$-NHC(O)(CH$_2$)$_2$—SH (350 mg, 16.7 μmol, Rapp Polymere GMBH, Tübingen, Germany). The resulting solution was stirred at rt and reaction progress was monitored on TLC using Ellman's reagent (DTNB). After all free thiol was consumed (~2 h), the reaction mixture was diluted with MeOH (3 mL) and then precipitated by slowly adding diethyl ether. Once the reaction mixture became cloudy, it was allowed to stand at 4° C. to induce complete precipitation. The solid was collected on a Buchner funnel and dried by suction. The solid was transferred to a reaction vessel and treated with 1:1 TFA/DCM for 2 h. The reaction mixture was concentrated in vacuo and the crude product was redissolved in water and purified using C-18 RP-HPLC (λ=214, 254; gradient: 20-60% $CH_3CN$ in $H_2O$ (0.1% TFA) over 30 minutes to afford the title compound (220 mg, 63%) as a white solid. $^1$H NMR (CDCl$_3$ with PEG suppression at δ 3.62): δ 8.24 (s, 1H), 8.10 (d, 1H, J=8.8 Hz), 7.84 (t, 1H, J=1.6 Hz), 7.68 (t, 1H, J=8.0 Hz), 7.57 (s, 1H), 7.50 (d, 1H, J=8.0 Hz), 7.09 (s, 1H), 3.62 (m, PEG CH$_2$), 3.36 (s, 3H, PEG-OCH$_3$) 3.08 (dd, 2H, J=28, 11 Hz), 2.69 (s, 3H), 2.24 (m, 4H), 2.05 (s, 3H).

Example 7 mPEG$_{30K}$ Amide of 6-[3'-(5-Carbamimidoyl-2-methylsulfanyl-thiophene-3-sulfonyl)-4-guanidino-6-methyl-biphenyl-2-ylcarbamoyl]-hexanoic acid bis-trifluoroacetate

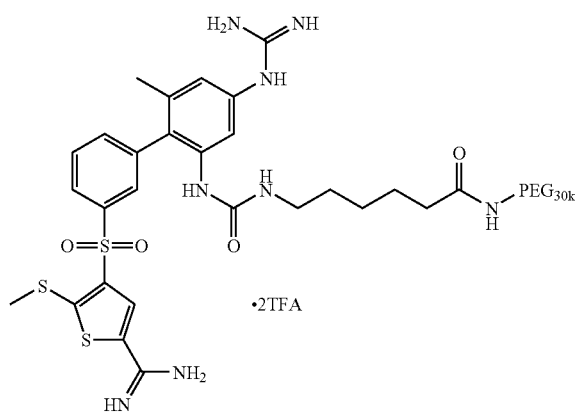

The title compound was synthesized using a similar procedure as described for Example 2, step j. Thus, diisopropylcarbodiimide (6.2 μL, 0.0399 mmol) was added to a solution of 6-(3-{3'-[5-(tert-butoxycarbonylamino-imino-methyl)-2-methylsulfanyl-thiophene-3-sulfonyl]-4-(N,N'-bis-tert-butoxycarbonyl)-guanidino-6-methyl-biphenyl-2-yl}-ureido)-hexanoic acid (40 mg, 0.0426 mmol, as prepared in Example 2, step i) and N,N-dimethylaminopyridine (9.1 mg, 0.074 mmol) in DCM (2.5 mL). The solution was stirred for 10 min and then mPEG$_{30K}$-NH$_2$ (800 mg, 0.0266 mmol, NOF Corporation, Japan) was added. The reaction was stirred at rt for 6 h (ninhydrin negative on TLC). DCM (10 mL) was added followed by the slow addition of Et$_2$O to induce a slow precipitation. An additional small portion of ether was added to insure complete precipitation, and the solid was collected by filtration and washed with DCM/Et$_2$O to yield ~700 mg of crude PEGylated compound. The precipitation was repeated. Analysis of the crude material by HPLC showed purity to be ~98%. The dried PEGylated compound was treated with TFA (50% in DCM, 6 mL). After stirring for 2 h, MeOH was added (4 mL) followed by slow addition of Et$_2$O to induce gradual precipitation. The solid was collected and the precipitation was repeated as described above. The solid was collected by filtration and dried in vacuo to provide the pure title compound as a white solid (640 mg). Analytical RP-HPLC (C18 column, 10-80% CH$_3$CN in H$_2$O (0.1% TFA, λ=214,254) over 10 min) indicated a purity >99%. $^1$H-NMR (CD$_3$OD) (with PEG suppression at δ 3.62): δ 8.45 (s, 1H), 8.11 (m, 1H), 7.93 (t, 1H, J=1.5 Hz), 7.83 (t, 1H, J=7.8 Hz), 7.73 (m, 1H) 7.61 (dt, 1H, J=1.2, 7.6 Hz), 7.04 (m, 1H), 3.62 (m, PEG methylenes), 3.28 (t, 2H, J=6.9 Hz, PEG-CH$_2$N), 3.10 (t, 2H, J=7.7 Hz), 2.76 (s, 3H), 2.19 (t, 2H, J=7.4 Hz), 2.03 (s, 3H), 1.62 (m, 2H), 1.45 (m, 1.32 (m, 2H).

Example 8

Conjugation with a bisubstituted-PEG$_{20K}$-(NH$_2$)$_2$ of 6-[3'(5-Carbamimidoyl-2-methylsulfanyl-thiophene-3-sulfonyl)-4-guanidino-6-methyl-biphenyl-2-ylcarbamoyl]-hexanoic acid tetra-trifluoroacetate

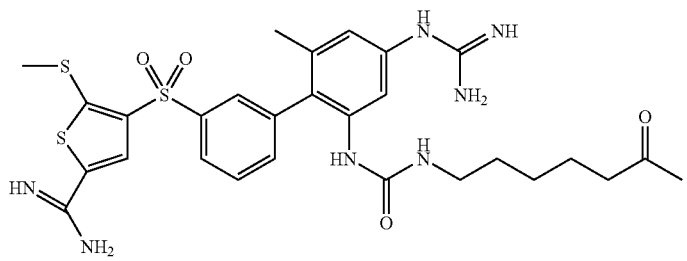

4 × TFA

-continued

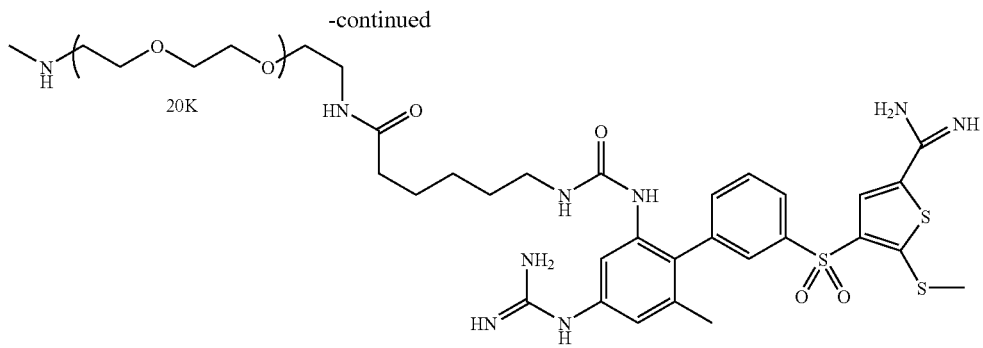

The title compound was synthesized using an identical procedure as that used in Example 7. Thus, reaction of diisopropylcarbodiimide (5.6 μL, 0.036 mmol), 6-(3-{3'-[5-(tert-butoxycarbonylamino-imino-methyl)-2-methylsulfanyl-thiophene-3-sulfonyl]-4-(N,N'-bis-tert-butoxycaronyl)-guanidino-6-methyl-biphenyl-2-yl}-ureido)-hexanoic acid (34 mg, 0.0365 mmol, as prepared in Example 2, step i), N,N-dimethylaminopyridine (8 mg, 0.066 mmol), and $PEG_{20K}$-$(NH_2)_2$ (255 mg, 0.0122 mmol, Rapp Polymere GMBH, Tübingen, Germany) in DCM (1 mL) followed by TFA treatment and same work up and purification as in Example 7 provided ~200 mg of the title compound as a white solid. $^1$H-NMR ($CD_3OD$) (with PEG suppression at δ 3.6): δ 8.45 (s, 1H), 8.12 (m, 1H), 7.92 (t, 1H, J=1.5 Hz), 7.83 (t, 1H, J=7.73 (m, 1H) 7.61 (dt, 1H, J=1.2, 7.6 Hz), 7.035 (m, 1H), 3.62 (m, PEG methylenes), 3.36 (t, 2H, J=5.5 Hz, PEG-$CH_2N$), 3.10 (t, 1H, J=6.7 Hz), 2.76 (s, 3H), 2.22 (t, 2H, J=7.3 Hz), 2.02 (s, 3H), 1.62 (m, 2H), 1.45 (m, 2H), 1.32 (m, 2H).

Example 9 mPEG$_{20K}$ Amide of 3-{[3'-(5-Carbamimidoyl-2-methylsulfanyl-thiophene-3-sulfonyl)-2-methyl-biphenyl-4-ylcarbamoyl]-methylsulfanyl}-propionic acid Trifluoroacetate To a solution of ({4-[4'-(2-bromo-acetylamino)-2'-methyl-biphenyl-3-sulfonyl]-5-methylsulfanyl-thiophen-2-yl}-imino-methyl)-carbamic acid tert-butyl ester (45 mg, 0.07 mmol, as prepared in Example 234, step a, WO-03099805) and $Et_3N$ (15 μL) in DCM (5 mL), was added mPEG$_{20K}$-$NHCO(CH_2)_2SH$ (1.13 g, 0.056 mmol, Rapp Polymere, GMBH, Tübingen, Germany). The reaction was stirred at rt for 1 h under Ar. Reaction completion was monitored using Ellman's reagent. The reaction mixture was concentrated in vacuo and the remaining residue was triturated with $Et_2O$ then treated with TFA (25% in DCM) for 40 min. Removal of the TFA/DCM and purification of the residue on RP-HPLC (C18 column, 20-60% $CH_3CN$ in $H_2O$ (0.1% TFA, λ=214, 254) over 30 min provided the pure title compound as the TFA salt. Analytical RP-HPLC (C18 column, 10-80% $CH_3CN$ in $H_2O$ (0.1% TFA, λ=214, 254) over 10 min) gave a single peak. $^1$H-NMR ($CD_3OD$) (with PEG suppression at δ 3.62): δ 8.38 (s, 1H), 8.03-8.06 (m, 1H), 7.97 (m, 1H), 7.71 (m, 2H), 7.56-7.61 (m, 2H), 7.21 (d, 1H, J=9.1 Hz), 3.62 (m, PEG methylenes), 3.37-3.4 (m, 5H), 3.36 (s, 3H, PEG-OMe), 2.97 (t, 2H, J=7.2 Hz), 2.75 (s, 3H), 2.60 (t, 2H, J=7.2 Hz), 2.26 (s, 3H).

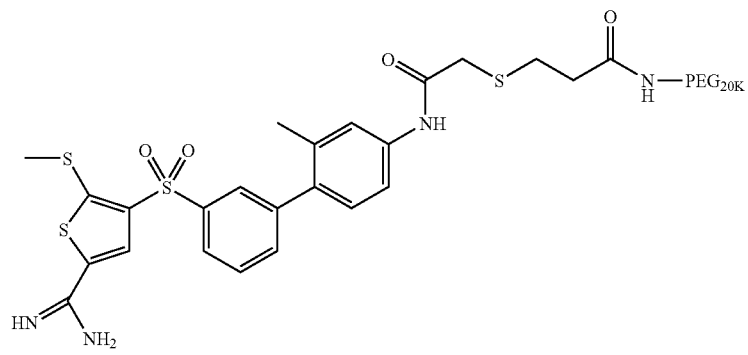

·TFA

Example 10

Tetravalent (4-Arm) PEG 2'-urea conjugate of 4-(2'-amino-4'-guanidino-6'-methyl-biphenyl-3-sulfonyl)-5-methylsulfanyl-thiophene-2-carboxamidine (octa)-trifluoroacetate (Pentaerythritol core)

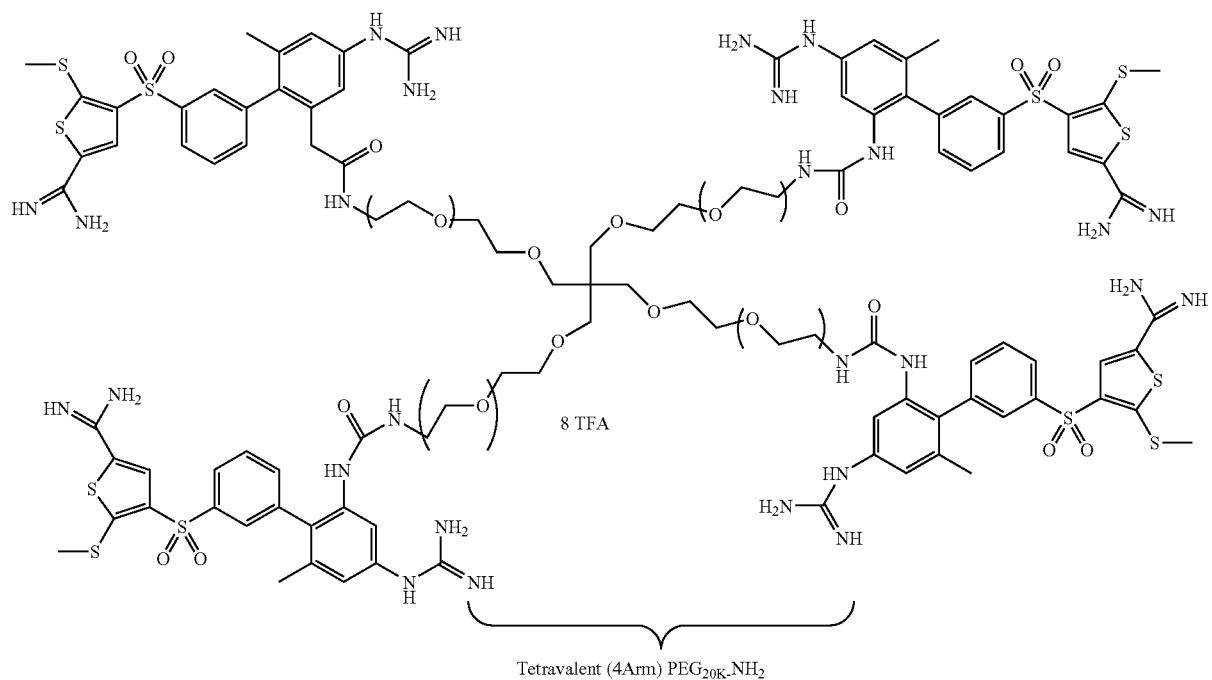

The title compound was synthesized using a similar procedure as described in Example 5, step c and d. 4-{4'-[N',N''-bis(tert-butoxycarbonyl)]-}-{[4-(2'-amino-6'-methyl-biphenyl-3-sulfonyl)-5-methylsulfanyl-thiophen-2-yl]-iminomethyl}-carbamic acid tert-butyl ester (Example 5: step b (155 mg, 0.2 mmol)) and pyridine (19 μL, 0.02 mmol) were dissolved into DCM (1.5 mL). The reaction was cooled to 0° C. followed by the addition of diisopropylethylamine (16 μL, 0.18 mmol) and p-nitrophenylchloroformate (35 mg, 0.17 mmol) and the reaction was stirred at 0° C. then rt for 30 minutes. To this was added tetravalent 4-arm $PEG_2OK-NH_2$ (500 mg, 0.025 mmol) and diisopropylethylamine (300 μL). The reaction was stirred at rt for 14 h. The solvents were removed in vacuo and the residue was dissolved into DCM. Ether (4× volume) was added slowly to the DCM/MeOH solution to precipitate the PEGylated compound. The solid was collected and the precipitation was repeated 2 more times. The solid was treated with TFA (50% in DCM, 5 mL) for 1 h at rt. The solvents were removed in vacuo and the residue was dissolved in MeOH/DCM and precipitated with $Et_2O$ 3 times. The collected solid was purified on RP-HPLC HPLC (C 18 column, 20-60% $CH_3CN$ in $H_2O$ (0.1% TFA, λ=214, 254) over 30 min to provide 400 mg of the title compound as a tan solid. $^1$H-NMR (with PEG suppression at δ 3.62) ($CD_3OD$): δ: 8.44 (s, 1H), 8.12 (d, 1H, J=7.2 Hz), 7.92 (br s, 1H), 7.82 (t, 1H, J=7.8 Hz), 7.71 (s, 1H), 7.61 (d, 1H, J=7.7 Hz), 7.04 (s, 1H), 3.62 (m, PEG methylenes), 3.27 (t, 2H, J=4.7 Hz), 2.76 (s, 3H), 2.02 (s, 1H).

Example 11

HOOC-PEG$_{5K}$ 2'-urea of 4-(2'-amino-4'-guanidino-6'-methyl-biphenyl-3-sulfonyl)-5-methylsulfanyl-thiophene-2-carboxamidine bis-trifluoroacetate

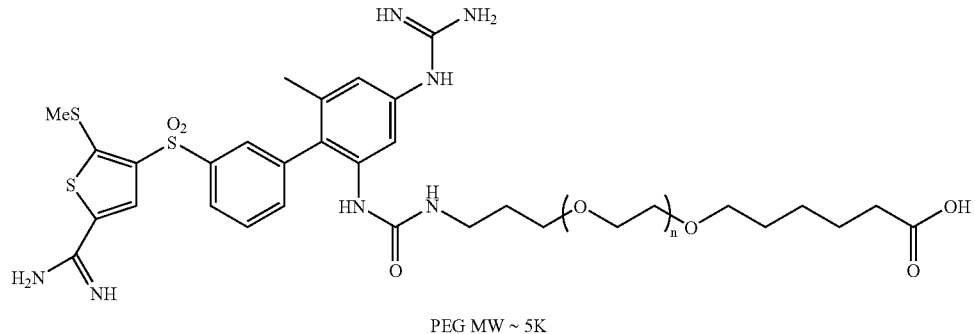

PEG MW ~ 5K

The title compound was synthesized as described in Example 10 using the following amounts: 4-{4'-[N',N''-bis(tert-butoxycarbonyl)]-}-{[4-(2'-amino-6'-methyl-biphenyl-3-sulfonyl)-5-methylsulfanyl-thiophen-2-yl]-imino-methyl}-carbamic acid tert-butyl ester (Example 5: step b (30 mg, 0.039 mmol)), pyridine (24 µL, 0.3 mmol), p-nitrophenylchloroformate (7.3 mg, 0.036 mmol), diisopropylethylamine (200 µL), and H$_2$N—PEG$_{5k}$-COOH (100 mg, 0.02 mmol, NOF, Japan) in DCM (1 mL). Similar work up and purification (precipitation and RP-HPLC) furnished 35 mg of the pure Boc-protected intermediate. Treatment with TFA followed by MeOH/DCM/Et$_2$O precipitations as described previously furnished the title compound as a white solid. $^1$H-NMR (with PEG suppression at δ 3.62) (CD$_3$OD): δ: 8.43 (s, 1H), 8.09-8.14 (m, 1H), 7.92 (t, 1H, J=1.6 Hz), 7.82 (t, 1H, J=7.8 Hz), 7.60-7.66 (m, 2H), 7.06 (d, 1H, J=1.6 Hz), 3.62 (m, PEG methylenes), 3.18 (t, 2H, J=6.8 Hz), 2.76 (s, 3H), 2.31 (t, 2H, J=7.4 Hz), 2.04 (s, 1H), 1.56-1.68 (m, 6H), 1.37-1.46 (m, 2H).

Example 12

Bivalent 45K PEG conjugate of 4-(2'-amino-4'-guanidino-6'-methyl-biphenyl-3-sulfonyl)-5-methyl-sulfanyl-thiophene-2-carboxamidine tetra-trifluoroacetate

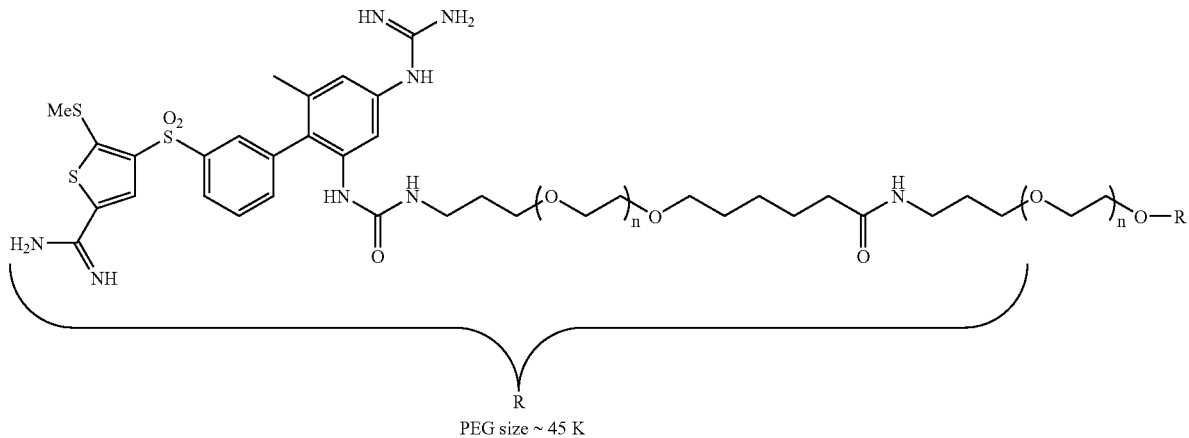

PEG size ~ 45 K

To a solution of the tris-Boc-protected HOOC-PEG$_{5K}$ 2'-urea of 4-(2'-amino-4'-guanidino-6'-methyl-biphenyl-3-sulfonyl)-5-methylsulfanyl-thiophene-2-carboxamidine (33 mg, 0.0065 mmol, as prepared in Example 11) and DMAP (3 mg, 0.018 mmol) in DCM (1 mL) was added diisopropylcarbodiimide (10 μL of 10% solution in DCM, 0.0064 mmol). The reaction was stirred for 10 min at rt, then PEG$_{35K}$-(NH$_2$)$_2$ (81 mg, 0.0023 mmol, NOF, Japan) was added in one portion. The reaction was allowed to stir at rt overnight. The solvents were removed in vacuo and the residue was precipitated from DCM/Et$_2$O as described in Example 7. The collected solid was purified on RP-HPLC using an isocratic gradient (35% CH$_3$CN/H$_2$O (0.1% TFA) over 30 min) to remove excess HOOC-PEG$_{5K}$-small molecule conjugate (early fraction) from the product (late fraction). The late fraction was treated with TFA (50% in DCM, 2 mL) for 4 h and the reaction mixture was concentrated in vacuo. The residue was chromatographed once again on RP-HPLC to provide the pure title compound as demonstrated by analytical RP-HPLC and $^1$H-NMR. $^1$H-NMR (with PEG suppression at δ 3.62) (CD$_3$OD): δ: 8.42 (s, 1H), 8.09-8.11 (m, 1H), 7.91 (t, 1H, J=1.7 Hz), 7.81 (t, 1H, J=7.8 Hz), 7.71 (s, 1H), 7.60-7.62 (m, 1H), 7.04 (d, 1H, J=1.6 Hz), 3.62 (m, PEG methylenes), 3.25 (t, 2H, J=6.8 Hz), 3.17 (t, 4 H, J=6.0 Hz), 2.75 (s, 3H), 2.18 (t, 2 H, J=7.5 Hz), 2.02 (s, 1H), 1.90-1.98 (m, 2H), 1.72-1.79 (m, 2H), 1.56-1.67 (m, 6H).

Example 13

Tetravalent PEG 2'-urea conjugate of 4-(2'-amino-4'-guanidino-6'-methyl-biphenyl-3-sulfonyl)-5-methyl-sulfanyl-thiophene-2-carboxamidine (octa)-trifluoro-acetate (Terminally branched with Lysine).

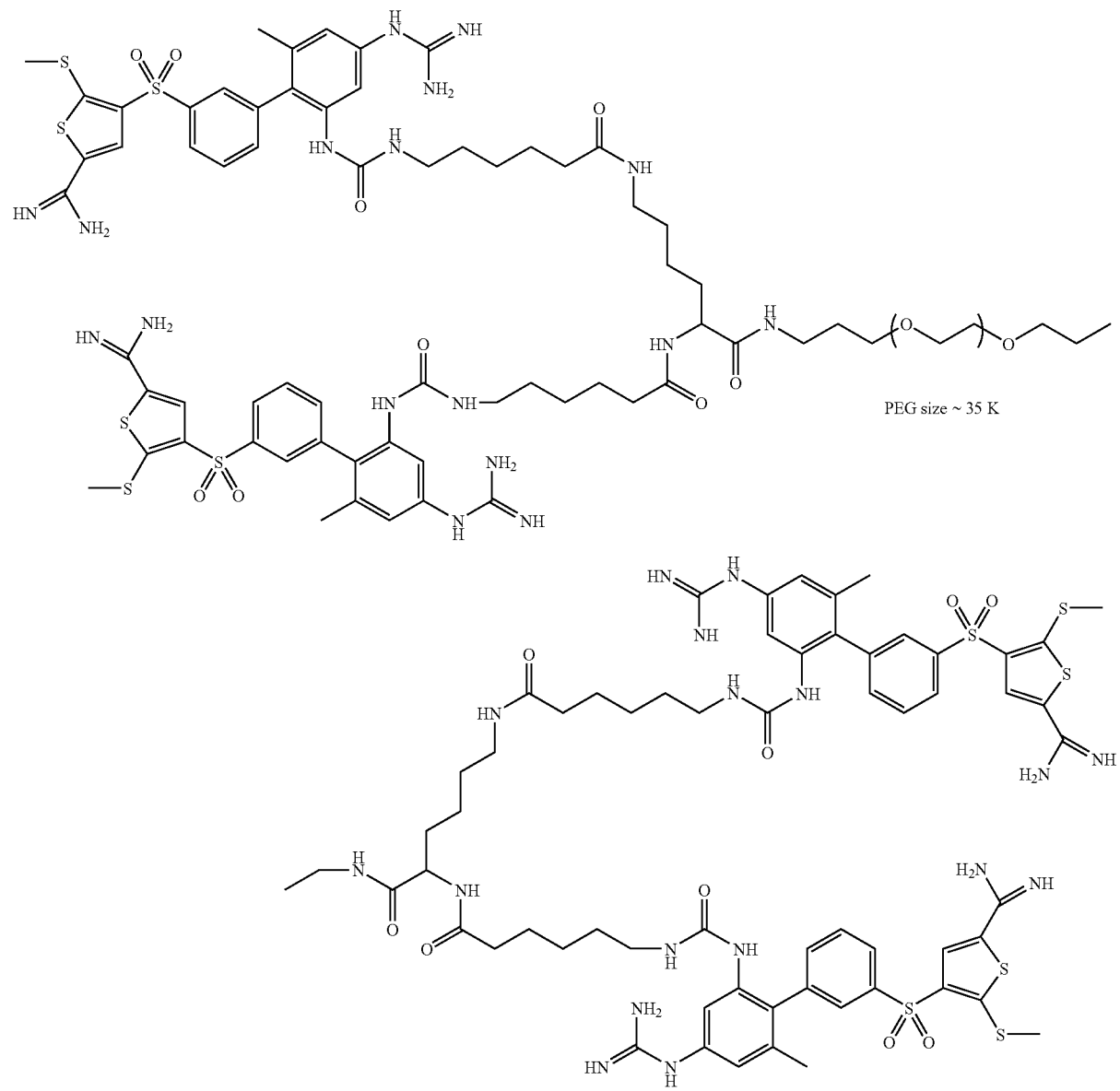

To a solution of PEG$_{35K}$-(NH$_2$)$_2$ (1 g, 28.6 mmol, NOF, Japan) and DMAP (0.035 mg, 0.286 mmol) in DCM (3.5 mL) at rt was added Boc-N-Lys(Boc)-N-hydroxy succinimide ester (102 mg, 0.229 mmol, Novabiochem). The viscous reaction mixture was stirred vigorously for 24 h then diluted with DCM and Et$_2$O was added slowly to cloudiness. The mixture was allowed to stand at 4° C. until precipitation was complete. The solid was collected by filtration and the process was repeated 3 more times. A white solid was collected and treated with TFA (50% in DCM) for 4 h at rt. The reaction mixture was concentrated to dryness and the residue was neutralized by adding excess DIEA and evaporating in vacuo to a give the desired intermediate as a solid. Following the same procedure described in Example 7, a portion of the recovered solid (300 mg, 0.0086 mmol) was reacted with 6-(3-{3'-[5-(tert-butoxycarbonylamino-imino-methyl)-2-methylsulfanyl-thiophene-3-sulfonyl]-4-(N,N'-bis-tert-butoxycarbonyl)-guanidino-6-methyl-biphenyl-2-yl}-ureido)-hexanoic acid (64 mg, 0.0686 mmol, as prepared in Example 2, step i), diisopropylcarbodiimide (10.6 µL, 0.068 mmol), and N,N-dimethylaminopyridine (16 mg, 0.129 mmol) in DCM (2 mL). The reaction mixture was concentrated and the residue was dissolved in a DCM/MeOH mixture and precipitated with Et$_2$O (3×). The filtered solid was treated with TFA (50% in DCM) for 6 h at rt. The volatiles were removed in vacuo and the residue was precipitated twice from MeOH/DCM/Et$_2$O to provide the pure title compound as a white solid as ascertained by analytical RP-HPLC and $^1$H-NMR. $^1$H-NMR (with PEG suppression at δ 3.62) (CD$_3$OD): δ: 8.44 (s, 1H), 8.09-8.11 (m, 1H), 7.92 (s, 1H), 7.82 (t, 1H, J=7.8 Hz), 7.73 (m, 1H), 7.60 (d, 1H, J=8.0 Hz), 7.03 (s, 1H), 3.62 (m, PEG methylenes), 3.05-3.12 (t, 2H, J=6.8 Hz), 2.75 (s, 3H), 2.19 (t, 2 H, J=7.7 Hz), 2.01 (s, 1H), 1.70-1.90 (m, 2H) 1.24-164 (m, 10H).

Example 14

PEG$_{40K}$ Amide of 6-[3'-(5-Carbamimidoyl-2-methyl-sulfanyl-thiophene-3-sulfonyl)-4-guanidino-6-methyl-biphenyl-2-ylcarbamoyl]-hexanoic acid bis-trifluoroacetate

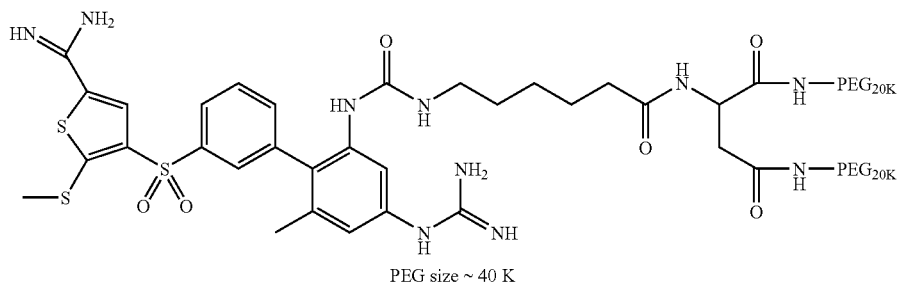

PEG size ~ 40 K

The title compound was synthesized using the same procedure described in Example 7 by reacting 6-(3-{3'-[5-(tert-butoxycarbonylamino-imino-methyl)-2-methylsulfanyl-thiophene-3-sulfonyl]-4-(N,N'-bis-tert-butoxycarbonyl)-guanidino-6-methyl-biphenyl-2-yl}-ureido)-hexanoic acid (25 mg, 0.027 mmol, as prepared in Example 2, step i), diisopropylcarbodiimide (4.3 µL, 0.027 mmol), N,N-dimethylaminopyridine (6.4 mg, 0.05 mmol), and Y-PEG$_{40K}$-NH$_2$ (700 mg, 0.0175 mmol, Sunbio, South Korea) in DCM (3 mL). Similar work up, precipitation, TFA treatment, and final precipitation provided the title compound as a white solid. $^1$H-NMR (CD$_3$OD) (with PEG suppression at δ 3.62): δ 8.45 (s, 1H), 8.11 (m, 1H), 7.91 (s, 1H), 7.66-7.84 (m, 2H), 7.61 (d, 1H, J=7.7 Hz), 7.04 (s, 1H), 3.62 (m, PEG methylenes), 2.77 (s, 3H), 2.60 (m, 2H), 2.25 (t, 2H, J=6.7 Hz), 2.01 (s, 3H), 1.60 (m, 2H), 1.42 (m, 2H), 1.25-1.35 (m, 2H).

Example 15

In Vitro Inhibition of C1s

Reagents: All buffer salts were obtained from Sigma Chemical Company (St. Louis, Mo.), and were of the highest purity available. DTNB was purchased from Pierce (Rockford, Ill.). Z-Gly-Arg-S-Bzl was purchased from Enzyme Systems Products (Livermore, Calif.). Activated human C1s was purchased from Calbiochem (La Jolla, Calif.).

K$_i$ Determinations: All assays are based on the ability of the test compound to inhibit the C1s-catalyzed hydrolysis of the substrate Z-Gly-Arg-S-Bzl, which is observed via a secondary reaction with 5,5'-dithio-bis(2-nitrobenzoic acid) (DTNB). In a typical K$_i$ determination, substrate is prepared in DMSO, and diluted into an assay buffer consisting of 50 mM HEPES, 200 mM NaCl, pH 7.5, 0.05% n-octyl-β-D-glucopyranoside. Substrate solutions were prepared at a concentration of 45 µM (K$_m$=78 µM) with DTNB at a concentration of 200 µM in assay buffer. Test compounds are prepared as a 10 µM final concentration in assay buffer. Dilutions of test compounds are prepared in assay buffer yielding at least 7 final concentrations encompassing a 700-fold concentration range. Purified activated C1s was diluted into assay buffer for a working concentration of 50 nM.

In a typical K$_i$ determination, into each well of a 96-well plate is pipetted 280 µL of substrate solution, 10 µL of test compound solution, and the plate allowed to thermally equilibrate at 37° C. for 10 minutes. Reactions were initiated by the addition of a 10 µL aliquot of the enzyme, and the absorbance increase at 405 nm is continuously recorded for 15 minutes in a Molecular Devices plate reader. Final reagent concentrations were: [C1s]=1.7 nM, [Z-Gly-Arg-S-Bzl]=45 µM, [DTNB]=200 µM. The ratio of the velocity (rate of change in absorbance as a function of time) for a sample containing no test compound is divided by the velocity of a sample containing test compound, and is plotted as a function of test compound concentration. The data are fit to a linear regression, and the value of the slope of the line calculated. The inverse of the slope is the experimentally determined apparent K$_i$ value (K$_i$ app). The K$_i$ app is corrected for true K$_i$ from the relationship between the substrate concentration [S] and the substrate Km, where K$_i$=K$_i$ app×(1/(1+[S]/Km)).

Example 16

In Vitro Inhibition of MASP-2

Reagents: All buffer salts were obtained from Sigma Chemical Company (St. Louis, Mo.), and were of the highest purity available. DTNB was purchased from Pierce (Rockford, Ill.). Z-Gly-Arg-S-Bzl was purchased from Enzyme Systems Products (Livermore, Calif.). Autoactivated 2-chain human MASP-2 (His-tag, Cys300-Phe686) was produced in-house from a Baculovirus expression system in insect cells.

$K_i$ Determinations: All assays are based on the ability of the test compound to inhibit the MASP-2-catalyzed hydrolysis of the substrate Z-Gly-Arg-S-Bzl, which is observed via a secondary reaction with 5,5'-dithio-bis(2-nitrobenzoic acid) (DTNB). In a typical $K_i$ determination, substrate is prepared in DMSO, and diluted into an assay buffer consisting of 50 mM HEPES, 200 mM NaCl, pH 7.5, 0.05% n-octyl-β-D-glucopyranoside. Substrate solutions were prepared at a concentration of 45 μM ($K_m$=8.6 μM) with DTNB at a concentration of 200 μM in assay buffer. Test compounds are prepared as a 10 μM final concentration in assay buffer. Dilutions of test compounds are prepared in assay buffer yielding at least 7 final concentrations encompassing a 700-fold concentration range. Purified activated MASP-2 was diluted into assay buffer for a working concentration of 30 nM.

In a typical $K_i$ determination, into each well of a 96-well plate is pipetted 280 μL of substrate solution, 10 μL of test compound solution, and the plate allowed to thermally equilibrate at 37° C. for 10 minutes. Reactions were initiated by the addition of a 10 μL aliquot of the enzyme, and the absorbance increase at 405 nm is continuously recorded for 15 minutes in a Molecular Devices plate reader. Final reagent concentrations were: [MASP-2]=1.0 mM, [Z-Gly-Arg-S-Bzl]=45 μM, [DTNB]=200 μM. The ratio of the velocity (rate of change in absorbance as a function of time) for a sample containing no test compound is divided by the velocity of a sample containing test compound, and is plotted as a function of test compound concentration. The data are fit to a linear regression, and the value of the slope of the line calculated. The inverse of the slope is the experimentally determined apparent $K_i$ value ($K_i$ app). The $K_i$ app is corrected for true $K_i$ from the relationship between the substrate concentration [S] and the substrate Km, where $K_i = K_i$ app×(1/(1+[S]/Km)).

Example 17

Complement Inhibition Data

The following compounds produced by the individual examples listed in TABLE 1 had their $K_i$ values determined according to the methods described in Examples 15 and 16.

TABLE 1

| Example | hC1s Ki corr. (μM) | MASP-2 Ki corr. (μM) |
| --- | --- | --- |
| 2 | 0.076 | 0.31 |
| 5 | 0.082 | 0.22 |
| 6 | 0.085 | — |
| 8 | 0.029 | — |
| 13 | 0.018 | — |

The examples have $K_i$ values in the range of 0.018 to 0.4 micromolar (μM) for C1s subcomponenet. Table 1 shows $K_i$ values for the inhibition of C1s and MASP-2 for a representative set of examples. The results indicate that the compounds of the present invention are inhibitors of complement.

The disclosures of each patent, patent application, and publication cited or described in this document are hereby incorporated herein by reference, in their entireties.

It is believed the chemical formulas and names used herein correctly and accurately reflect the underlying chemical compounds. However, the nature and value of the present invention does not depend upon the theoretical correctness of these formulae, in whole or in part. Thus it is understood that the formulas used herein, as well as the chemical names attributed to the correspondingly indicated compounds, are not intended to limit the invention in any way, including restricting it to any specific tautomeric form or to any specific optical; or geometric isomer, except where such stereochemistry is clearly defined.

Various modifications of the invention, in addition to those described herein, will be apparent to those skilled in the art from the foregoing description. Such modifications are also intended to fall within the scope of the appended claims.

What is claimed:

1. The compound of having the following formula;

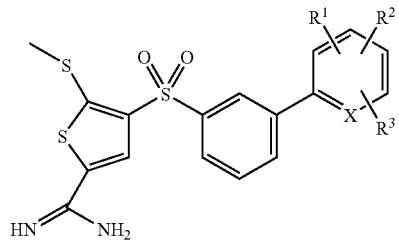

wherein X is C or N; $R^1$ is —NH(C=O)NH-PEG-OCH$_3$ or —NH(C=O)NH(CH$_2$)$_n$(C=O)NH-PEG-OCH$_3$; $R^2$ is ureido or guanidino; $R^3$ is C$_{1-4}$ alkyl; and PEG is a polyethylene glycol having a molecular weight of 20-40 K; and the pharmaceutically acceptable salts thereof.

2. The compound of claim 1 which is

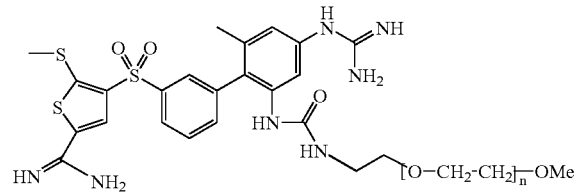

wherein n is from about 17 to about 1400, and pharmaceutically acceptable salts and esters thereof.

3. The compound of claim 2 which is mPEG$_{20K}$ 2'-urea of 4-(2'-amino-4'-guanidino-6'-methyl-biphenyl-3-sulfonyl)-5-methylsulfanyl-thiophene-2-carboxamidine.

4. The compound of claim 2 which is the bis-trifluoroacetate salt.

5. The compound of claim 2 which is the bis-hydrochloride salt

6. The compound of claim 2 which is PEG$_{40K}$ Amide of 6-[3'-(5-Carbamimidoyl-2-methylsulfanyl-thiophene-3-sulfonyl)-4-guanidino-6-methyl-biphenyl-2ylcarbamoyl]-hexanoic acid bis-trifluoroacetate, or bis hydrochloride salt, or pharmaceutically acceptable salts and esters thereof, having the following formula:

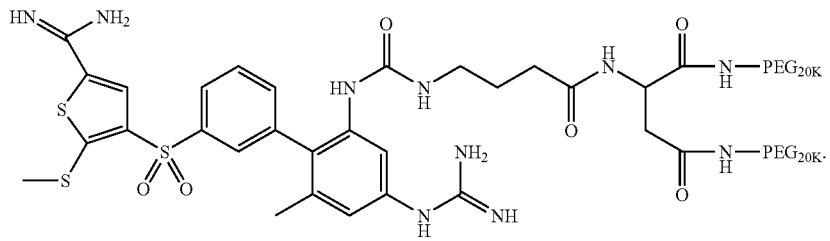

PEG size~ 40 K

7. The compound of claim 1 which is

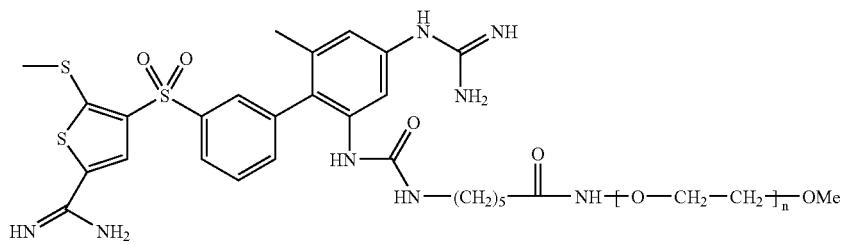

wherein n is is from about 17 to about 1400.

8. The compound of claim 1 which is mPEG$_{20-30K}$ amide of 6-[3'-(5-carbamimidoyl-2-methylsulfanyl-thiophene-3-sulfonyl)-4-guanidino-6-methyl-biphenyl-2-ylcarbamoyl]-hexanoic acid, having the following formula:

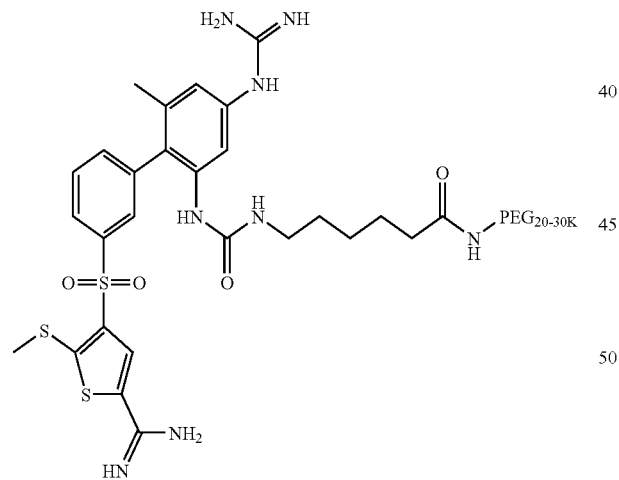

and pharmaceutically acceptable salts and esters thereof.

9. The compound of claim 8 in which the PEG is 20K.

10. The compound of claim 8 which is the bis-trifluoroacetate salt.

11. The compound of claim 8 which is the bis-hydrochloride salt.

* * * * *